United States Patent
Bluestone et al.

(10) Patent No.: US 6,491,916 B1
(45) Date of Patent: Dec. 10, 2002

(54) METHODS AND MATERIALS FOR MODULATION OF THE IMMUNOSUPPRESIVE ACTIVITY AND TOXICITY OF MONOCLONAL ANTIBODIES

(75) Inventors: Jeffrey A. Bluestone, San Francisco, CA (US); Robert A. Zivin, Skillman; Linda K. Jolliffe, Hillsborough, both of NJ (US)

(73) Assignees: Tolerance Therapeutics, Inc., Chicago, IL (US); Ortho Pharmaceutical Corporation, New Brunswick, NJ (US)

( * ) Notice: Subject to any disclaimer, the term of this patent is extended or adjusted under 35 U.S.C. 154(b) by 0 days.

(21) Appl. No.: 08/557,050

(22) PCT Filed: Jun. 1, 1994

(86) PCT No.: PCT/US94/06198

§ 371 (c)(1),
(2), (4) Date: Oct. 9, 1998

(87) PCT Pub. No.: WO94/28027

PCT Pub. Date: Dec. 8, 1994

Related U.S. Application Data

(63) Continuation-in-part of application No. 08/070,116, filed on Jun. 1, 1994, now Pat. No. 5,885,573.

(51) Int. Cl.[7] ................ A61K 39/395; C07K 16/28; C07K 16/18

(52) U.S. Cl. ............... 424/133.1; 424/800; 424/801; 424/144.1; 424/154.1; 424/173.1; 530/388.22; 530/388.75; 530/387.3; 530/867

(58) Field of Search ................ 424/133.1, 800, 424/801, 144.1, 154.1, 173.1; 530/387.3, 867, 388.22, 388.75

(56) References Cited

U.S. PATENT DOCUMENTS

| | | |
|---|---|---|
| 4,079,126 A | 3/1978 | Homma et al. |
| 4,221,794 A | 9/1980 | Simon et al. |
| 4,361,549 A | 11/1982 | Kung et al. |
| 4,515,893 A | 5/1985 | Kung et al. |
| 4,658,019 A | 4/1987 | Kung et al. |
| 4,695,624 A | 9/1987 | Marburg et al. |
| 4,830,852 A | 5/1989 | Marburg et al. |
| 4,882,317 A | 11/1989 | Marburg et al. |
| 4,882,424 A | 11/1989 | Schlossman et al. |
| 5,078,998 A | 1/1992 | Bevan et al. |
| 5,585,089 A | 12/1996 | Queen et al. ............ 424/133.1 |
| 5,624,821 A | 4/1997 | Winter et al. |

FOREIGN PATENT DOCUMENTS

| | | |
|---|---|---|
| EP | 0440373 | 1/1991 |
| EP | 0613944 | 9/1994 |
| WO | 90/05541 | 5/1990 |
| WO | 91/01143 | 2/1991 |
| WO | 91/04053 | 4/1991 |
| WO | 91/09966 | 7/1991 |
| WO | 91/09968 | 7/1991 |
| WO | 92/00092 | 1/1992 |
| WO | 92/15671 | 9/1992 |
| WO | 93/00431 | 1/1993 |
| WO | 93/19767 | 10/1993 |
| WO | 93/25712 | 12/1993 |
| WO | 94/23760 | 1/1994 |
| WO | 94/28912 | 12/1994 |
| WO | WO 95/03408 | 2/1995 |

OTHER PUBLICATIONS

Cole et al., "Human IgG2 variants of chimeric anti–CD3 are nonmitogenic to T cells," *J. Immunol.*, 159:3613–3621, 1997.

Adair et al., "Humanization of the Murine Anti–Human CD3 Monoclonal Antibody OKT3," *Hum. Antibodies Hybridomas*, 5(1):41–47, 1994.

Alegre et al., "A Non–Activating "Humanized" Anti–CD3 Monoclonal Antibody Retains Immunosuppressive Properties In Vivo," *Transplantation*, 57(11):1537–1543, 1994.

Alegre et al., "In vitro and in vivo Properties of "Humanized" Anti–CD3 Monoclonal Antibodies with Different Affinities for Fc Receptor," *8th International Congress of Immunology*, 23–28, Aug. 1992.

Alegre et al., "Effect of a Single Amino Acid Mutation in the Fc Portion of a "Humanized" OKT3 on T Cell Responses In Vitro," *J. Am. Soc. Nephol.*, 2(3): 1991.

Alegre et al., "Effect of a Single Amino Acid Mutation on the Activating and Immunosuppressive Properties of a "Humanized" OKT3 Monoclonal Antibody," *The Journal of Immunology*, 148(11):3461–3468, 1992.

Alegre et al., "Cytokine Release Syndrome Induced by the 145–2C11 Anti–CD3 Monoclonal Antibody in Mice: Prevention by High Doses of Methylprednisolone," *The Journal of Immunology*, 146(4):1184–1191, 1991.

Archer et al., "Inverse Relationship Between Immune Interferon Induction and Mitogen Effects on the Maturation of the Primary Antibody Response," *Immunopharmacology*, 3:71–81, 1981.

Aruffo, A. and Seed, B., "Molecular Cloning of a CD28 cDNA by a High–Efficiency COS Cell Expression System," *Proc. Natl. Acad. Sci. USA*, 84:8573–8577, 1987.

Azuma, M., et al., "B70 Antigen is a Second Ligand for CTLA–4 and CD28", *Nature*, 366:76–79, 1993.

Azuma et al., "Involvement of CD28 in MHC–Unrestricted Cytotoxicity Mediated by a Human Natural Killer Leukemia Cell Line," *The Journal of Immunology*, 149:1115–1123, 1992.

(List continued on next page.)

*Primary Examiner*—Ronald B. Schwadron
(74) *Attorney, Agent, or Firm*—Fulbright & Jaworski L.L.P.

(57) ABSTRACT

The binding specificity of the murine OKT3 has been transferred into a human antibody framework in order to reduce its immunogenicity. These "humanized" anti-CD3 monoclonal antibodies retain, in vitro, all the properties of native anti-CD3 antibodies, including T cell activation which has been correlated, in vivo, with the severe side-effects observed in transplant recipients after the first administration of the mAb.

5 Claims, 22 Drawing Sheets

OTHER PUBLICATIONS

Beyers et al., "Activation of T Lymphocytes via Monoclonal Antibodies Against Rat Cell Surface Antigens with Particular Reference to CD2 Antigen," *Immunological Reviews*, (111):59–77, 1989.

Bierer and Burakoff, "T–Lymphocyte Activation: The Biology and Function of CD2 and CD4," *Immunological Reviews*, (111):267–293, 1989.

Bluestone, J., Hirsch, R., and Ellenhorn J., "In Vivo Administration of Monoclonal Anti–T Cell Antibodies Can Activate Immune Responses and Prevent Malignant Progressive Tumor Growth." Presented at U.S. Japan Cooperative Program in Cancer Research, Honolulu, Hawaii (Jan. 1989).

Bolt et al., "The Generation of a Humanized, Non–mitogenic CD3 Monoclonal Antibody Which Retains in vitro Immunosuppressive Properties," *Eur. J. Immunol.*, 23:403–411, 1993.

Boussiotis, V., et al., "Activated Human B Lymphocytes Express Three CTLA–4 Counterreceptors That Costimulate T–cell activation", *Proc. Natl. Acad. Sci, USA*, 90:11059–11063, 1993.

Boussiotis et al., "B7 But Not Intercellular Adhesion Molecule–1 Costimulation Prevents the Induction of Human Alloantigen–Specific Tolerance," *J. Exp. Med.*, 178:1753–1763, 1993.

Bruce et al., "Enhanced humoral response to HIV–peptidic antigen with coadministration of low–dose anti–CD3 monoclonal antibody in mice," abstract for the Joint Meeting of the American Society for Biochemistry and Molecular Biology and the American Association of Immunologists, New Orleans, LA, Jun. 4–7, 1990, *FASEB*, 4(7):A2015, 1990.

Burton, "Immunoglobin G: Functional Sites," *Molecular Immunology*, 22(3):161–206, 1985.

Carayanniotis and Barber, "Adjuvant–free IgG Responses Induced with Antigen Coupled to Antibodies Against Class II MHC," *Nature*, 327:59–61, 1987.

Chang et al., "Does OKT3 Monoclonal Antibody React with an Antigen–Recognition Structure on Human T Cells?" *Proc. Natl. Acad. Sci. USA*, 78(3):1805–1808, 1981.

Chatenoud et al., "Systemic Reaction to the Anti–T–Cell Monoclonal Antibody OKT3 in Relation to Serum Levels of Tumor Necrosis Factor and Interferon–a," *The New England Journal of Medicine*, 320(21):1420–1421, 1989.

Chen et al., "Costimulation of T Cells for Tumor Immunity," *Immunology Today*, 14(10):483–486, 1993.

Cosimi et al., "Prolonged Survival of Nonhuman Primate Renal Allograft Recipients Treated Only with Anti–CD4 Monoclonal Antibody," *Surgery*, 108(2):406–414, 1990.

Danbolt et al., "Purification and Reconstitution of the Sodium– and Potassium–Coupled Glutamate Transport Glycoprotein from Rat Brain," *Biochemistry*, 29:6734–6740, 1990.

DeVries et al., "Interplay between the TCR/CD3 Complex and CD4 or CD8 in the Activation of Cytotoxic T Lymphocytes," *Immunological Reviews*, 109:119–141, 1989.

Duncan et al., "Localization of the binding site for the human high–affinity Fc receptors on IgG," *Nature*, 332:563–564, 1988.

Emmrich et al., "Cross–linking of the T cell Receptor Complex with the Subset–Specific Differentiation Antigen Stimulates Interleukin 2 Receptor Expression in Human CD4 and CD8 T Cells," *Eur. J. Immunol.*, 17:529–534, 1987.

Flens et al., "Efficient Expansion of Tumor–Infiltrating Lymphocytes from Solid Tumors by Stimulation with Combined CD3 and CD28 Monoclonal Antibodies," *Cancer Immunol. Immunother.*, 37:323–328, 1993.

Fraser, J.D., et al., "Regulation of Interleukin–2 Gene Enhancer Activity by the T Cell Accessory Molecule CD28", *Science*, pp. 313–316, Jan. 18, 1991.

Freedman, A.S., et al., "Selective Induction of B7/BB–1 on Interferon–g Stimulated Monocytes: A Potential Mechanism for Amplification of T Cell Activation Through the CD28 Pathway", *Cellular Immunology*, 137:429–437, 1991.

Freeman, G.J., et al., "Uncovering of Functional Alternative CTLA–4 Counter–Receptor in B7–Deficient Mice", *Science*, 262:907–909, 1993.

Freeman, G.J., et al., "Murine B7–2, an Alternative CTLA4 Counter–receptor That Costimulates T Cell Proliferation and Interleukin 2 Production", *The Journal of Experimental Medicine*, 178:2185–2192, 1993.

Freeman, G.J., et al., "Cloning of B7–2: A CTLA–4 Counter–Receptor That Costimulates Human T Cell Proliferation", *Science*, 262:909–911, 1993.

Gabizon et al., "Effect of Liposome Composition and Other Factors on the Targeting of Liposomes to Experimental Tumors: Biodistribution and Imaging Studies," *Cancer Research*, 50:6371–6378, 1990.

Geppert et al., "Accessory Cell Independent Proliferation of Human T4 Cells Stimulated by Immobilized Monoclonal Antibodies to CD3," *J. Immunol.*, 1987, 138(6):1660–1666.

Gergely and Sarmay, "The two binding–site models of human IgG binding Fcg receptors," *The FASEB Journal*, 4:3275–3283, 1990.

Gimmi, C.D., et al., "B–cell Surface Antigen B7 Provides a Costimulatory Signal That Induces T Cells to Proliferate and Secrete Interleukin 2", *Proc. Natl. Acad, Sci, USA*, 88:6575–6579, 1991.

Gross, J.A., et al., "Identification and Distribution of The Costimulatory Receptor CD28 in the Mouse", *The Journal of Immunology*, 149:380–388, 1992.

Guerder, S., et al., "Costimulator B7–1 Confers Antigen–Presenting–Cell Function to Parenchymal Tissue and In Conjunction with Tumor Necrosis Factor a Leads to Autoimmunity in Transgenic Mice", *Proc. Natl. Acad. Sci. USA*, 91:5138–5142, 1994.

Harding and Allison, "CD28–B7 Interactions Allow the Induction of CD8$^+$ Cytotoxic T Lymphocytes in the Absence of Exogenous Help," *J. Exp. Med.*, 177:1791–1796, 1993.

Harding, F.A., et al., "CD28–Mediated Signalling Co–Stimulates Murine T Cells and Prevents Induction of Anergy in T–cell Clones", *Nature*, 356:607–609, 1992.

Harlow and Lane, "Storing and Purifying Antibodies," *Antibodies A Laboratory Manual*, 284–287, 1988.

Harper, K., et al., "CTLA–4 and CD28 Activated Lymphocyte Molecules Are Closely related in Both Mouse and Human as to Sequence, Message Expression, Gene Structure, and Chromosomal Location", *The Journal of Immunology*, 147:1037–1044, 1991.

Harris et al., "Therapeutic Antibodies—the Coming of Age," *Tibtech*, 1993, 11:42–44, Feb. 1993.

Havran et al., "Expression and Function of the CD3–Antigen Receptor on Murine CD4$^+$8$^+$ Thymocytes," *Nature*, 330(12):170–173, 1987.

Heath, W.R., et al., "Autoimmune Diabetes as a Consequence of Locally Produced Interleukin–2", *Nature*, 359:547–549, 1992.

Janeway, "The T Cell Receptor as a Multicomponent Signalling Machine: CD4/CD8 Coreceptors and CD45 in T Cell Activation," *Annu. Rev. Immunol.,* 10:645–74, 1992.

Jefferis et al., "Molecular Definition of Interaction Sites on Human IgG for Fc Receptors (huFcgR)," *Molecular Immunology,* 27(12):1237–1240, 1990.

Jenkins, M.K., et al., "Induction and Maintenance of Anergy in Mature T Cells", *Advances in Experimental Medicine and Biology,* 292:167–176, 1991.

Jenkins, M.K., et al., "CD28 Delivers a Costimulatory Signal Involved in Antigen–specific IL–2 Production by Human T Cells", *The Journal of Immunology,* 147:2461–2466, 1991.

Jolliffe, Linda K., "Humanized Antibodies: Enhancing Therapeutic Utility Through Antibody Engineering," *Intern. Rev. Immunol.,* 10:241–250, 1993.

June, C.H., et al., "The B7 and CD28 Receptor Families", *Immunol. Today,* 15(7):321–331, 1994.

Lenschow, D.J., et al., "Expression and Functional Significance of an additional Ligand for CTLA–4", *Proc. Natl. Acad. Sci. USA,* 90:11054–11058, 1993.

Lenschow, D.J., et al., "Long–Term Survival of Xenogeneic Pancreatic Islet Grafts Induced by CTLA4Ig", *Science,* 257:789–792, 1992.

Li et al., "Costimulation of Tumor–Reactive $CD4^+$ and $CD8^+$ T Lymphocytes by B7, a Natural Ligand for CD38, Can Be Used to Treat Established Mouse Melanoma," *The Journal of Immunology,* 421–428, Jul. 1994.

Lin et al., "Long–Term Acceptance of Major Histocompatibility Complex Mismatched Cardiac Allografts Induced by CTLA4Ig Plus Donor–specific Transfusion," *J. Exp. Med.,* 178:1801–1806, Nov. 1993.

Lindsten, T., et al., "Characterization of CTLA–4 Structure and Expression on Human T Cells", *The Journal of Immunology,* 151:3489–3499, 1993.

Lindsten, T., et al., "Regulation of Lymphokine Messenger RNA Stability by a Surface–Mediated T Cell Activation Pathway", *Science,* 244:339–343, 1989.

Linsley, P.S., et al., "CTLA–4 Is a Second Receptor for the B Cell Activation Antigen B7", *J. Exp. Med.,* 174:561–569, 1991.

Liu and Linsley, "Costimulation of T–cell Growth", Current Opinion in Immunology, 4:265–270, 1992.

Male et al., *Advanced Immunology,* pp. 11.8–11.9, Gower Medical Publishing, London, England, H. Hadjidimitriadou, ed., 1987.

Mannik, M. and Person R., "New antigenic determinants revealed on human IgG by binding two immunoblotting membranes," *Journal of Immunological Methods,* 144:265–267, 1991.

Newell et al., "Death of Mature T Cells by Separate Ligation fo CD4 and the T–Cell Receptor for Antigen," *Nature,* 347:286–289, 1990.

Newell et al., "In vivo TCR–mediated and T cell activation results in immunopotentiation and tumor regression," abstract for the Joint Meeting of the American Society for Biochemistry and Molecular Biology and the American Association of Immunologists, New Orleans, LA, Jun. 4–7, 1990, *FASEB,* 4(7):A2022, 1990.

Nickoloff, B.J., et al., "Discordant Expression of CD28 Ligands, BB–1 and B7 on Keratinocytes in Vitro and Psoriatic Cells in Vivo", *American Journal of Pathology,* 142(4):1029–1040, 1993.

Ortho Multicenter Transplant Study Group, "A Randomized Clinical Trial of OKT3 Monoclonal Antibody for Acute Rejection of Gadaveric Renal Transplants," *The New England Journal of Medicine,* 313(6):337–342, 1985.

Partridge et al., "The Use of Anti–IgG Monoclonal Antibodies in Mapping the Monocyte Receptor Site in IgG," *Molecular Immunology,* 23(12):1365–1372, 1986.

Parlevliet et al., "Anti–CD3 Murine Monoclonal Isotype Switch Variants Tested for Toxicity and Immunologic Monitoring in Four Chimpanzees," *Brief Communications,* 50(5):889–892, 1990.

Razi–Wolf, et al., "Expression and Function of the Murine B7 Antigen, the Major Costimulatory Molecule Expressed by Peritoneal Exudate Cells", *Proc. Natl. Acad. Sci. USA,* 89:4210–4214, 1992.

Reiser, et al., "Murine B7 Antigen Provides an Efficient Costimulatory Signal for Activation of Murine T Lymphocytes via the T–Cell Receptor/CD3 Complex", *Proc. Natl. Acad. Sci. USA,* 89:271–275, 1992.

Richards et al., "Phase IB Evaluation of OKT3," 82nd Annual Meeting of the American Association for Cancer Research, Houston, Texas, USA, May 15–18, 1991.

Robbins and Bergdoll, "Production of rabbit antisera to the staphylococcal enterotoxins," *Immunology,* 78(5):4028, abstract No. 35589, 1984.

Roitt et al., *Immunology,* p. 9.9, Gower Medical Publishing, London, England, van den Berghe, ed., 1989.

Rudd, "CD4, CD8 and the TCR–CD3 Complex: a Novel Class of Protein–Tyrosine Kinase Receptor," *Immunology Today,* 11(11):400–406, 1990.

Rudd et al., "Molecular Interactions, T–Cell Subsets and a Role of the CD4/CD8:$p56^{lck}$ Complex in Human T–Cell Activation," *Immunological Reviews,* 111:225–266, 1989.

Schiff et al., "Lymphocyte killing of macrophages induced by OKT3 monoclonal antibody", FASEB, 70th Annual Meeting, St. Louis, Missouri, Apr. 13–18, 1986, p1100, No. 5499.

Schwartz, R.H., et al., "T–Cell Clonal Anergy", *Cold Spring Harbo Symposia on Quantitative Biology,* LIV:605–610, 1989.

Schwartz, R.H., "A Cell Culture Model for T Lymphocyte Clonal Anergy", *Science,* 248:1349–1356, 1990.

Seed, Brian, "An LFA–3 cDNA encodes a phospholipid–linked membrane protein homologous to its receptor CD2," *Nature,* 329:840–842, 1987.

Seed, B. and Aruffo, A., "Molecular cloning of the CD2 antigen, the T–cell erythrocyte receptor, by a rapid immunoselection procedure," *Proc. Natl. Acad. Sci. USA,* 84:3365–3369, 1987.

Sehon, "Carl Prausnitz Memorial Lecture, Suppression of Antibody Responses by Chemically Modified Antigens," *Int. Arch. Allergy Appl. Immunol.,* 94:11–20, 1991.

Shahinian, A., et al., "Differential T Cell Costimulatory Requirements in CD28–Deficient Mice", *Med. and Clin. Microbiol.,* 83(10):AB–590, abstract No. 98234, 1987.

Shinagawa et al., "Purification of Staphylococcal Toxic Shock Syndrome Toxin–1 (Enterotoxin F) and Preparation of Anti–Toxic Shock Syndrome Toxin–1 Serum," *J. Fac. Agriciwate Univ.,* 18(1):47–58, 1987.

Smith et al., "Inhibition of T Cell Activation by a Monoclonal Antibody Reactive Against the a3 Domain of Human MHC Class I Molecules," *The Journal of Immunology,* 1054–1067, Jul. 1994.

Thistlethwaite, Jr. et al., "OKT3 Treatment of Steroid–Resistant Renal Allograft Rejection," *Transplantation,* 43(2):176–184, 1987.

Urba et al., "Anti–CD3 monoclonal antibody treatment of patients with CD3–negative tumors," *Canc. Res.,* 52:2394–2401, May 1, 1992.

Waid et al., "Treatment of Acute Cellular Rejection with T10B9.1A–31 or OKT3 in Renal Allograft Recipients," *Transplantation,* 53(1):80–86, 1992.

Wedrychowski et al., "Immune Enhancers Composed of Polyvalent Binding Sites of Anti–CD3 Antibodies," *Bio/Technology,* 11:486–489, 1993.

Woodle et al., "Humanized OKT3 Antibodies: Successful Transfer of Immune Modulating Properties and Idiotype Expression," *The Journal of Immunology,* 148:2756–2763, May 1992.

White et al., "The Vβ–Specific Superantigen Staphylococcal Enterotoxin B: Stimulation fo Mature T Cells and Clonal Deletion in Neonatal Mice," *Cell,* 56:27–35, 1989.

Wu, Y., et al., "A Major Costimulatory Molecule on Antigen–Presenting Cells, CTLA4 Ligand A, is Distinct From B7", *J. Exp. Med.,* 178:1789–1793, 1993.

Xu et al., "Construction of a mouse–human chimeric light chain from murine monoclonal antibodies 33.28 against colorectal carcinoma–associated antigens," abstract No. 2109, FASEB 75th Annual Meeting, Atlanta, GA, Apr. 21–25, 1991.

Xu, D., "Humanization and Effector Function Modification of Orthoclone OKT®3," poster abstract for Lymphocytes and Antibodies FASEB Summer Res. Conference, dated Mar. 25, 1993.

Zivin, R.A., "Functional Analysis of Humanized OKT3 and OKT4A," Second Annual IBC International Conference on Antibody Engineering, Dec. 16–18, 1991, San Diego, CA.

Zivin, R.A., a talk presented by Linda Jolliffe, sponsored by Journal of Human Antibodies and Hybridomas, abstract for Second International Conference on Human Antibodies and Hybridomas, Mar. 24–26, 1992, Cambridge, England.

Zivin, R.A., "Monoclonal Antibodies in Transplantation," a talk presented by Linda Jolliffe at the Tokyo Symposium on Therapeutic Antibodies, Jan. 1993.

Zivin, R.A., "Fc Region Modified CDR–grafted OKT3: Effector Functions by Design," poster presentation for FASEB Summer Conference: Antibodies and Lymphocytes, Jun. 1993.

```
        1         10        20        30         40        50        60
Okt3v1  QIVLTQSPAIMSASPGEKVTMTCSASS-SVSYMNWYQQKSGTSPKRWIYDTSKLASGVPA
REI     DIQMTQSPSSLSASVGDRVTITCQASQDIIKYLNWYQQTPGKAPKLLIYEASNLQAGVPS
gLA     ............SA.S-SVS.M...............DT.K.AS...
gLC     ............SA.S-SVS.M...........RW..DT.K.AS...

70        80        90        100       108
Okt3v1  HFRGSGSGTSYSLTISGMEAEDAATYYCQQWSSNPFTFGSGTKLEINR  (SEQ ID NO:6)
REI     RFSGSGSGTDYTFTISSLQPEDIATYYCQQYQSLPYTFGQGTKLQITR  (SEQ ID NO:7)
gLA     ....................WS.N.F.............          (SEQ ID NO:8)
gLC     ....................WS.N.F.............          (SEQ ID NO:9)
```

FIG. 1A

```
         1            10           20          30            40           50       a     60
         QVQLQQSGAELARPGASVKMSCKASGYTFTRYTMHWVKQRPGQGLEWIGYINPSRGYTNYN
Okt3vh
KOL      QVQLVESGGGVVQPGRSLRLSCSSSGFIFSSYAMYWVRQAPGKGLEWVAIWDDGSDQHYA
gH       .............................YT.TR.T.H..........Y.NPSRGYTN.N
gHA      .........Q...................KA.YT.TR.T.H.......IGY.NPSRGYTN.N
gHG      .........Q...................KA.YT.TR.T.H.......IGY.NPSRGYTN.N 70           80  abc       90      100abcdefghi            110
Okt3vh   QKFKDKATLTTDKSSSTAYMQLSSLTSEDSAVYYCARYYDDHYCL-----DYWGQGTTLTVSS  (SEQ ID NO:10)
KOL      DSVKGRFTISRDNSKNTLFLQMDSLRPEDTGVYFCARDGGHGFCSSASCFGPDYWGQGTPVTVSS  (SEQ ID NO:11)
gH       QKF.D.........................YDDHY.L----.........  (SEQ ID NO:12)
gHA      QK..D...I.K.S.A.............A..Y..YDDHY.L----.......  (SEQ ID NO:13)
gHG      QK..D...........A...............YDDHY.L----.........  (SEQ ID NO:14)
```

FIG. 1B

```
         10          20          30          40          50          60          70
ATCCTGGCAA AGATTGTAAT ACGACTCACT ATAGGGCGAA TTCGCCGCCA CC ATG GAA TGG AGC TGG GTC
                                                          Met Glu Trp Ser Trp Val 80          90         100         110         120         130
TTT CTC TTC CTG TCA GTA ACT ACA GGT GTC CAC TCC CAG GTT CAG CTG GTG CAG TCT GGA
Phe Leu Phe Leu Ser Val Thr Thr Gly Val His Ser Gln Val Gln Leu Val Gln Ser Gly 140         150         160         170         180         190
GGA GGT GTC GTC CAG CCT GGA AGG TCC CTG AGA CTG TCT TGT AAG GCT TCT GGA TAC ACC TTC
Gly Gly Val Val Gln Pro Gly Arg Ser Leu Arg Leu Ser Cys Lys Ala Ser Gly Tyr Thr Phe 200         210         220         230         240         250
ACT AGA TAC ACA ATG CAC TGG GTC AGA CAG GCT CCT GGA AAG GGA CTC GAG TGG ATT GGA TAC
Thr Arg Tyr Thr Met His Trp Val Arg Gln Ala Pro Gly Lys Gly Leu Glu Trp Ile Gly Tyr 260         270         280         290         300         310         320
ATT AAT CCT AGC AGA GGT TAT ACT AAC TAC AAT CAG AAG GTG AAG GAC AGA TTC ACA ATT TCT
Ile Asn Pro Ser Arg Gly Tyr Thr Asn Tyr Asn Gln Lys Val Lys Asp Arg Phe Thr Ile Ser
```

FIG. 2A

```
                          330                     340                     350                     360                     370                     380
                     AGA GAC AAT TCT AAG AAT ACA GCC TTC CTG CAG ATG GAC TCA CTC AGA CCT GAG GAT ACC GGA
                     Arg Asp Asn Ser Lys Asn Thr Ala Phe Leu Gln Met Asp Ser Leu Arg Pro Glu Asp Thr Gly 390                     400                     410                     420                     430                     440
            GTC TAT TTT TGT GCT AGA TAT TAC GAT GAC CAC TAC TGT CTG GAC TAC TGG GGC CAA GGT ACC
            Val Tyr Phe Cys Ala Arg Tyr Tyr Asp Asp His Tyr Cys Leu Asp Tyr Trp Gly Gln Gly Thr 450                     460                     470                     480                     490                     500                     510
   CCG GTC ACC GTC AGC TCA GCT TCC ACC AAG GGC CCA TCC GTC TTC CCC CTG GCG CCC TGC TCC
   Pro Val Thr Val Ser Ser Ala Ser Thr Lys Gly Pro Ser Val Phe Pro Leu Ala Pro Cys Ser 520                     530                     540                     550                     560                     570
            AGG AGC ACC TCC GAG AGC ACA GCC GCC CTG GGC TGC CTG GTC AAG GAC TAC TTC CCC GAA CCG
            Arg Ser Thr Ser Glu Ser Thr Ala Ala Leu Gly Cys Leu Val Lys Asp Tyr Phe Pro Glu Pro 580                     590                     600                     610                     620                     630
   GTG ACG GTG TCG TGG AAC TCA GGC GCC CTG ACC AGC GGC GTG CAC ACC TTC CCG GCT GTC CTA
   Val Thr Val Ser Trp Asn Ser Gly Ala Leu Thr Ser Gly Val His Thr Phe Pro Ala Val Leu
```

FIG. 2B

```
640             650         660         670         680         690         700
CAG TCC TCA GGA CTC TAC TCC CTC AGC AGC GTG GTG ACC GTG CCC TCC AGC AGC TTG GGC ACG
Gln Ser Ser Gly Leu Tyr Ser Leu Ser Ser Val Val Thr Val Pro Ser Ser Ser Leu Gly Thr 710         720         730         740         750         760
AAG ACC TAC ACC TGC AAC GTA GAT CAC AAG CCC AGC AAC ACC AAG GTG GAC AAG AGA GTT
Lys Thr Tyr Thr Cys Asn Val Asp His Lys Pro Ser Asn Thr Lys Val Asp Lys Arg Val 770         780         790         800         810         820         830
GGTGAGAGGC CAGCACAGGG AGGGAGGGTG TCTGCTGGAA GCCAGGCTCA GCCCTCCTGC CTGGACGCAC 840         850         860         870         880         890         900
CCCGGCTGTG CAGCCCCAGC CCAGGGCAGC AAGGCATGCC CCATCTGTCT CCTCACCCGG AGGCCTCTGA 910         920         930         940         950         960         970
CCACCCCACT CATGCTCAGG GAGAGGGTCT TCTGGATTTT TCCACCAGGC TCCCGGCACC ACAGGCTGGA 980         990        1000        1010        1020        1030        1040
TGCCCCTACC CCAGGCCCTG CGCATACAGG GCAGGTGCTG CGCTCAGACC TGCCAAGAGC CATATCCGGG
```

FIG. 2C

```
     1050        1060       1070       1080       1090       1100       1110
AGGACCCTGC  CCCTGACCTA AGCCCACCCC AAAGGCCAAA CTCTCCACTC CCTCAGCTCA GACACCTTCT 1120        1130       1140       1150       1160       1170       1180
CTCCTCCCAG  ATCTGAGTAA CTCCCAATCT TCTCTCTGCA GAG TCC AAA TAT GGT CCC CCA TGC CCA TCA
                                            Glu Ser Lys Tyr Gly Pro Pro Cys Pro Ser 1190        1200       1210       1220       1230       1240
TGC CCA GGTAAGCCAA CCCAGGCCTC GCCCTCCAGC TCAAGGCGGG ACAGGTGCCC TAGAGTAGCC
Cys Pro 1250        1260       1270       1280       1290       1300       1310       1320
TGCATCCAGG  GACAGGCCCC AGCCGGGTGC TGACGCATCC ACCTCCATCT CTTCCTCAGC A CCT GAG TTC CTG GGG
                                                                 Pro Glu Phe Leu Gly 1330        1340       1350       1360       1370       1380
GGA CCA TCA GTC TTC CTG TTC CCC CCA AAA CCC AAG GAC ACT CTC ATG ATC TCC CGG ACC CCT
Gly Pro Ser Val Phe Leu Phe Pro Pro Lys Pro Lys Asp Thr Leu Met Ile Ser Arg Thr Pro
```

FIG. 2D

```
1390           1400            1410            1420            1430            1440
GAG GTC ACG TGC GTG GTG GAC GTG AGC CAG GAA GAC CCC GAG GTC CAG TTC AAC TGG TAC
Glu Val Thr Cys Val Val Asp Val Ser Gln Glu Asp Pro Glu Val Gln Phe Asn Trp Tyr 1450           1460            1470            1480            1490            1500            1510
GTG GAT GGC GTG GAG GTG CAT AAT GCC AAG ACA AAG CCG CGG GAG GAG CAG TTC AAC AGC ACG
Val Asp Gly Val Glu Val His Asn Ala Lys Thr Lys Pro Arg Glu Glu Gln Phe Asn Ser Thr 1520            1530            1540            1550            1560            1570
TAC CGT GTG GTC AGC GTC CTC ACC GTC CTG CAC CAG GAC TGG CTG AAC GGC AAG GAG TAC AAG
Tyr Arg Val Val Ser Val Leu Thr Val Leu His Gln Asp Trp Leu Asn Gly Lys Glu Tyr Lys 1580            1590            1600            1610            1620            1630
TGC AAG GTC TCC AAC AAA GGC CTC CCG TCC TCC ATC GAG AAA ACC ATC TCC AAA GCC AAA
Cys Lys Val Ser Asn Lys Gly Leu Pro Ser Ser Ile Glu Lys Thr Ile Ser Lys Ala Lys 1640           1650            1660            1670            1680            1690            1700            1710
GGTGGG ACCCACGGGG TGGGAGGGCC ACACGGACAG AGGCCAGCTC GGCCCACCCT CTGCCCTGGG AGTGACCGCT
```

FIG. 2E

```
1720           1730              1740          1750              1760              1770
GTGCCAACCT CTGTCCCTAC A GGG CAG CCC CGA GAG CCA CAG GTG TAC ACC CTG CCC CCA TCC CAG
                        Gly Gln Pro Arg Glu Pro Gln Val Tyr Thr Leu Pro Pro Ser Gln 1780           1790           1800           1810          1820          1830
GAG GAG ATG ACC AAG AAC CAG GTC AGC CTG ACC TGC CTG GTC AAA GGC TTC TAC CCC AGC GAC
Glu Glu Met Thr Lys Asn Gln Val Ser Leu Thr Cys Leu Val Lys Gly Phe Tyr Pro Ser Asp 1840           1850           1860           1870          1880          1890          1900
ATC GCC GTG GAG TGG GAG AGC AAT GGG CAG CCG GAG AAC AAC TAC AAG ACC ACG CCT CCC GTG
Ile Ala Val Glu Trp Glu Ser Asn Gly Gln Pro Glu Asn Asn Tyr Lys Thr Thr Pro Pro Val 1910           1920           1930           1940          1950          1960
CTG GAC TCC GAC GGC TCC TTC TTC CTC TAC AGC AGG CTA ACC GTG GAC AAG AGC AGG TGG CAG
Leu Asp Ser Asp Gly Ser Phe Phe Leu Tyr Ser Arg Leu Thr Val Asp Lys Ser Arg Trp Gln 1970           1980           1990           2000          2010          2020
GAG GGG AAT GTC TTC TCA TGC TCC GTG ATG CAT GAG GCT CTG CAC AAC CAC TAC ACA CAG AAG
Glu Gly Asn Val Phe Ser Cys Ser Val Met His Glu Ala Leu His Asn His Tyr Thr Gln Lys
```

FIG. 2F

```
2030      2040           2050            2060            2070            2080            2090
AGC CTC TCC CTG TCT CTG GGT AAA TGAGTGCCAG GGCCGGCAAG CCCCGCTCC CCGGGCTCTC
Ser Leu Ser Leu Ser Leu Gly Lys 2100       2110            2120            2130            2140            2150            2160
GGGGTCGCGC GAGGATGCTT GGCACGTACC CCGTCTACAT ACTTCCCAGG CACCCAGCAT GGAAATAAAG 2170       2180            2190            2200            2210            2220            2230
CACCCACCAC TGCCCTGGGC CCCTGTGAGA CTGTGATGGT TCTTTCCACG GGTCAGGCCG AGTCTGAGGC 2240       2250            2260            2270            2280            2290            2300
CTGAGTGACA TGAGGGAGGC AGAGCGGGTC CCACTGTCCC CACACTGGCC CAGGCGGTTGC AGTGTGTCCT 2310       2320            2330            2340            2350            2360            2370
GGGCCACCTA GGGTGGGGCT CAGCCAGGGG CTCCCTCGGC AGGGTGGGGC ATTTGCCAGC GTGGCCCTCC 2380       2390
CTCCAGCAGC AGGACTCTAG AGGATCC
```

FIG. 2G

| Isotype | 234 | 235 | 236 | 237 | 238 | 239 | |
|---|---|---|---|---|---|---|---|
| hIgG1 hIgG3 mIgG2a | Leu | Leu | Gly | Gly | Pro | Ser | (SEQ ID NO: 18) |
| hIgG4 | Phe | Leu | Gly | Gly | Pro | Ser | (SEQ ID NO: 19) |
| hIgG2 | Val | - - - | Ala | Gly | Pro | Ser | (SEQ ID NO: 20) |
| mIgG2b | Leu | Glu | Gly | Gly | Pro | Ser | (SEQ ID NO: 21) |
| hIgG1A/A | Ala | Ala | Gly | Gly | Pro | Ser | (SEQ ID NO: 22) |
| hIgG4A/A | Ala | Ala | Gly | Gly | Pro | Ser | (SEQ ID NO: 23) |

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
       (A) LENGTH: 2399 base pairs
       (B) TYPE: nucleic acid
       (C) STRANDEDNESS: single
       (D) TOPOLOGY: linear (ix) FEATURE:
       (A) NAME/KEY: CDS
       (B) LOCATION: 53..760

(ix) FEATURE:
       (A) NAME/KEY: CDS
       (B) LOCATION: 1151..1186

(ix) FEATURE:
       (A) NAME/KEY: CDS
       (B) LOCATION: 1308..1634

(ix) FEATURE:
       (A) NAME/KEY: CDS
       (B) LOCATION: 1732..2052

(xi) SEQUENCE DESCRIPTION: SEQ ID NO:1:

```
ATCCTGGCAA AGATTGTAAT ACGACTCACT ATAGGGCGAA TTCGCCGCCA CC ATG         55
                                                          Met
                                                            1

GAA TGG AGC TGG GTC TTT CTC TTC TTC CTG TCA GTA ACT ACA GGT GTC     103
Glu Trp Ser Trp Val Phe Leu Phe Phe Leu Ser Val Thr Thr Gly Val
              5                  10                  15

CAC TCC CAG GTT CAG CTG GTG CAG TCT GGA GGA GGA GTC GTC CAG CCT     151
His Ser Gln Val Gln Leu Val Gln Ser Gly Gly Gly Val Val Gln Pro
         20                  25                  30

GGA AGG TCC CTG AGA CTG TCT TGT AAG GCT TCT GGA TAC ACC TTC ACT     199
Gly Arg Ser Leu Arg Leu Ser Cys Lys Ala Ser Gly Tyr Thr Phe Thr
     35                  40                  45

AGA TAC ACA ATG CAC TGG GTC AGA CAG GCT CCT GGA AAG GGA CTC GAG     247
Arg Tyr Thr Met His Trp Val Arg Gln Ala Pro Gly Lys Gly Leu Glu
 50                  55                  60                  65

TGG ATT GGA TAC ATT AAT CCT AGC AGA GGT TAT ACT AAC TAC AAT CAG     295
Trp Ile Gly Tyr Ile Asn Pro Ser Arg Gly Tyr Thr Asn Tyr Asn Gln
                 70                  75                  80

AAG GTG AAG GAC AGA TTC ACA ATT TCT AGA GAC AAT TCT AAG AAT ACA     343
Lys Val Lys Asp Arg Phe Thr Ile Ser Arg Asp Asn Ser Lys Asn Thr
             85                  90                  95

GCC TTC CTG CAG ATG GAC TCA CTC AGA CCT GAG GAT ACC GGA GTC TAT     391
Ala Phe Leu Gln Met Asp Ser Leu Arg Pro Glu Asp Thr Gly Val Tyr
        100                 105                 110

TTT TGT GCT AGA TAT TAC GAT GAC CAC TAC TGT CTG GAC TAC TGG GGC     439
Phe Cys Ala Arg Tyr Tyr Asp Asp His Tyr Cys Leu Asp Tyr Trp Gly
    115                 120                 125
```

```
CAA GGT ACC CCG GTC ACC GTG AGC TCA GCT TCC ACC AAG GGC CCA TCC      487
Gln Gly Thr Pro Val Thr Val Ser Ser Ala Ser Thr Lys Gly Pro Ser
130             135                 140                 145

GTC TTC CCC CTG GCG CCC TGC TCC AGG AGC ACC TCC GAG AGC ACA GCC      535
Val Phe Pro Leu Ala Pro Cys Ser Arg Ser Thr Ser Glu Ser Thr Ala
                150                 155                 160

GCC CTG GGC TGC CTG GTC AAG GAC TAC TTC CCC GAA CCG GTG ACG GTG      583
Ala Leu Gly Cys Leu Val Lys Asp Tyr Phe Pro Glu Pro Val Thr Val
            165                 170                 175

TCG TGG AAC TCA GGC GCC CTG ACC AGC GGC GTG CAC ACC TTC CCG GCT      631
Ser Trp Asn Ser Gly Ala Leu Thr Ser Gly Val His Thr Phe Pro Ala
        180                 185                 190

GTC CTA CAG TCC TCA GGA CTC TAC TCC CTC AGC AGC GTG GTG ACC GTG      679
Val Leu Gln Ser Ser Gly Leu Tyr Ser Leu Ser Ser Val Val Thr Val
195                 200                 205

CCC TCC AGC AGC TTG GGC ACG AAG ACC TAC ACC TGC AAC GTA GAT CAC      727
Pro Ser Ser Ser Leu Gly Thr Lys Thr Tyr Thr Cys Asn Val Asp His
210                 215                 220                 225

AAG CCC AGC AAC ACC AAG GTG GAC AAG AGA GTT GGTGAGAGGC CAGCACAGGG    780
Lys Pro Ser Asn Thr Lys Val Asp Lys Arg Val
                230                 235

AGGGAGGGTG TCTGCTGGAA GCCAGGCTCA GCCCTCCTGC CTGGACGCAC CCCGGCTGTG    840

CAGCCCCAGC CCAGGGCAGC AAGGCATGCC CCATCTGTCT CCTCACCCGG AGGCCTCTGA    900

CCACCCCACT CATGCTCAGG GAGAGGGTCT TCTGGATTTT TCCACCAGGC TCCCGGCACC    960

ACAGGCTGGA TGCCCCTACC CCAGGCCCTG CGCATACAGG GCAGGTGCTG CGCTCAGACC   1020

TGCCAAGAGC CATATCCGGG AGGACCCTGC CCCTGACCTA AGCCCACCCC AAAGGCCAAA   1080

CTCTCCACTC CCTCAGCTCA GACACCTTCT CTCCTCCCAG ATCTGAGTAA CTCCCAATCT   1140

TCTCTCTGCA GAG TCC AAA TAT GGT CCC CCA TGC CCA TCA TGC CCA          1186
           Glu Ser Lys Tyr Gly Pro Pro Cys Pro Ser Cys Pro
           1               5                   10

GGTAAGCCAA CCCAGGCCTC GCCCTCCAGC TCAAGGCGGG ACAGGTGCCC TAGAGTAGCC   1246

TGCATCCAGG GACAGGCCCC AGCCGGGTGC TGACGCATCC ACCTCCATCT CTTCCTCAGC   1306

A CCT GAG TTC CTG GGG GGA CCA TCA GTC TTC CTG TTC CCC CCA AAA       1352
  Pro Glu Phe Leu Gly Gly Pro Ser Val Phe Leu Phe Pro Pro Lys
  1               5                   10                  15

CCC AAG GAC ACT CTC ATG ATC TCC CGG ACC CCT GAG GTC ACG TGC GTG    1400
Pro Lys Asp Thr Leu Met Ile Ser Arg Thr Pro Glu Val Thr Cys Val
                20                  25                  30

GTG GTG GAC GTG AGC CAG GAA GAC CCC GAG GTC CAG TTC AAC TGG TAC    1448
Val Val Asp Val Ser Gln Glu Asp Pro Glu Val Gln Phe Asn Trp Tyr
            35                  40                  45

GTG GAT GGC GTG GAG GTG CAT AAT GCC AAG ACA AAG CCG CGG GAG GAG    1496
Val Asp Gly Val Glu Val His Asn Ala Lys Thr Lys Pro Arg Glu Glu
        50                  55                  60

CAG TTC AAC AGC ACG TAC CGT GTG GTC AGC GTC CTC ACC GTC CTG CAC    1544
Gln Phe Asn Ser Thr Tyr Arg Val Val Ser Val Leu Thr Val Leu His
    65                  70                  75

CAG GAC TGG CTG AAC GGC AAG GAG TAC AAG TGC AAG GTC TCC AAC AAA    1592
Gln Asp Trp Leu Asn Gly Lys Glu Tyr Lys Cys Lys Val Ser Asn Lys
80                  85                  90                  95

GGC CTC CCG TCC TCC ATC GAG AAA ACC ATC TCC AAA GCC AAA            1634
Gly Leu Pro Ser Ser Ile Glu Lys Thr Ile Ser Lys Ala Lys
                    100                 105

GGTGGGACCC ACGGGGTGCG AGGGCCACAC GGACAGAGGC CAGCTCGGCC CACCCTCTGC   1694
```

```
CCTGGGAGTG ACCGCTGTGC AACCTCTGT CCCTACA GGG CAG CCC CGA GAG CCA    1749
                                           Gly Gln Pro Arg Glu Pro
                                            1               5

CAG GTG TAC ACC CTG CCC CCA TCC CAG GAG GAG ATG ACC AAG AAC CAG    1797
Gln Val Tyr Thr Leu Pro Pro Ser Gln Glu Glu Met Thr Lys Asn Gln
            10              15                  20

GTC AGC CTG ACC TGC CTG GTC AAA GGC TTC TAC CCC AGC GAC ATC GCC    1845
Val Ser Leu Thr Cys Leu Val Lys Gly Phe Tyr Pro Ser Asp Ile Ala
                25              30                  35

GTG GAG TGG GAG AGC AAT GGG CAG CCG GAG AAC AAC TAC AAG ACC ACG    1893
Val Glu Trp Glu Ser Asn Gly Gln Pro Glu Asn Asn Tyr Lys Thr Thr
        40                  45                  50

CCT CCC GTG CTG GAC TCC GAC GGC TCC TTC TTC CTC TAC AGC AGG CTA    1941
Pro Pro Val Leu Asp Ser Asp Gly Ser Phe Phe Leu Tyr Ser Arg Leu
 55              60                  65                  70

ACC GTG GAC AAG AGC AGG TGG CAG GAG GGG AAT GTC TTC TCA TGC TCC    1989
Thr Val Asp Lys Ser Arg Trp Gln Glu Gly Asn Val Phe Ser Cys Ser
                75                  80                  85

GTG ATG CAT GAG GCT CTG CAC AAC CAC TAC ACA CAG AAG AGC CTC TCC    2037
Val Met His Glu Ala Leu His Asn His Tyr Thr Gln Lys Ser Leu Ser
            90                  95                 100

CTG TCT CTG GGT AAA TGAGTGCCAG GGCCGGCAAG CCCCCGCTCC CCGGGCTCTC    2092
Leu Ser Leu Gly Lys
            105

GGGGTCGCGC GAGGATGCTT GGCACGTACC CCGTCTACAT ACTTCCCAGG CACCCAGCAT    2152

GGAAATAAAG CACCCACCAC TGCCCTGGGC CCCTGTGAGA CTGTGATGGT TCTTTCCACG    2212

GGTCAGGCCG AGTCTGAGGC CTGAGTGACA TGAGGGAGGC AGAGCGGGTC CCACTGTCCC    2272

CACACTGGCC CAGGCGTTGC AGTGTGTCCT GGGCCACCTA GGGTGGGGCT CAGCCAGGGG    2332

CTCCCTCGGC AGGGTGGGGC ATTTGCCAGC GTGGCCCTCC CTCCAGCAGC AGGACTCTAG    2392

AGGATCC                                                              2399

(2) INFORMATION FOR SEQ ID NO:2:

(i) SEQUENCE CHARACTERISTICS:
        (A) LENGTH: 236 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Trp Ser Trp Val Phe Leu Phe Phe Leu Ser Val Thr Thr Gly
 1               5                  10                  15

Val His Ser Gln Val Gln Leu Val Gln Ser Gly Gly Gly Val Val Gln
            20                  25                  30

Pro Gly Arg Ser Leu Arg Leu Ser Cys Lys Ala Ser Gly Tyr Thr Phe
        35                  40                  45

Thr Arg Tyr Thr Met His Trp Val Arg Gln Ala Pro Gly Lys Gly Leu
 50                  55                  60

Glu Trp Ile Gly Tyr Ile Asn Pro Ser Arg Gly Tyr Thr Asn Tyr Asn
 65                  70                  75                  80

Gln Lys Val Lys Asp Arg Phe Thr Ile Ser Arg Asp Asn Ser Lys Asn
                85                  90                  95

Thr Ala Phe Leu Gln Met Asp Ser Leu Arg Pro Glu Asp Thr Gly Val
            100                 105                 110

Tyr Phe Cys Ala Arg Tyr Tyr Asp Asp His Tyr Cys Leu Asp Tyr Trp
        115                 120                 125
```

```
Gly Gln Gly Thr Pro Val Thr Val Ser Ser Ala Ser Thr Lys Gly Pro
    130                 135                 140

Ser Val Phe Pro Leu Ala Pro Cys Ser Arg Ser Thr Ser Glu Ser Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
                180                 185                 190

Ala Val Leu Gln Ser Ser Gly Leu Tyr Ser Leu Ser Ser Val Val Thr
            195                 200                 205

Val Pro Ser Ser Ser Leu Gly Thr Lys Thr Tyr Thr Cys Asn Val Asp
        210                 215                 220

His Lys Pro Ser Asn Thr Lys Val Asp Lys Arg Val
225                 230                 235

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:3:

Glu Ser Lys Tyr Gly Pro Pro Cys Pro Ser Cys Pro
1               5                   10

(2) INFORMATION FOR SEQ ID NO:4:

(i) SEQUENCE CHARACTERISTICS:
        (A) LENGTH: 109 amino acids
        (B) TYPE: amino acid
        (D) TOPOLOGY: linear (ii) MOLECULE TYPE: protein (xi) SEQUENCE DESCRIPTION: SEQ ID NO:4:

Pro Glu Phe Leu Gly Gly Pro Ser Val Phe Leu Phe Pro Pro Lys Pro
1               5                   10                  15

Lys Asp Thr Leu Met Ile Ser Arg Thr Pro Glu Val Thr Cys Val Val
                20                  25                  30

Val Asp Val Ser Gln Glu Asp Pro Glu Val Gln Phe Asn Trp Tyr Val
            35                  40                  45

Asp Gly Val Glu Val His Asn Ala Lys Thr Lys Pro Arg Glu Glu Gln
        50                  55                  60

Phe Asn Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
                100                 105

(2) INFORMATION FOR SEQ ID NO:5:

(i) SEQUENCE CHARACTERISTICS:
        (A) LENGTH: 107 amino acids
        (B) TYPE: amino acid
        (D) TOPOLOGY: linear (ii) MOLECULE TYPE: protein
```

(xi) SEQUENCE DESCRIPTION: SEQ ID NO:5:

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

(2) INFORMATION FOR SEQ ID NO:6:

(i) SEQUENCE CHARACTERISTICS:
        (A) LENGTH: 107 amino acids
        (B) TYPE: amino acid
        (C) STRANDEDNESS:
        (D) TOPOLOGY: linear (xi) SEQUENCE DESCRIPTION: SEQ ID NO:6:

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Val Ser Tyr Met
            20                  25                  30

Asn Trp Tyr Gln Gln Lys Ser Gly Thr Ser Pro Lys Arg Trp Ile Tyr
            35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

(2) INFORMATION FOR SEQ ID NO:7:

(i) SEQUENCE CHARACTERISTICS:
        (A) LENGTH: 108 amino acids
        (B) TYPE: amino acid
        (C) STRANDEDNESS:
        (D) TOPOLOGY: linear (xi) SEQUENCE DESCRIPTION: SEQ ID NO:7:

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ile Lys Tyr
            20                  25                  30

Leu Asn Trp Tyr Gln Gln Thr Pro Gly Lys Ala Pro Lys Leu Leu Ile
            35                  40                  45

Tyr Glu Ala Ser Asn Leu Gln Ala Gly Val Pro Ser Arg Phe Ser Gly
    50                  55                  60

```
Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
                 85                  90                  95

Thr Phe Gly Gln Gly Thr Lys Leu Gln Ile Thr Arg
                100                 105
```

(2) INFORMATION FOR SEQ ID NO:8:

(i) SEQUENCE CHARACTERISTICS:
        (A) LENGTH: 107 amino acids
        (B) TYPE: amino acid
        (C) STRANDEDNESS:
        (D) TOPOLOGY: linear (xi) SEQUENCE DESCRIPTION: SEQ ID NO:8:

```
Asp Ile Gln Met Thr Gln Ser Pro Ser Ser Leu Ser Ala Ser Val Gly
 1                5                  10                  15

Asp Arg Val Thr Ile Thr Cys Ser Ala Ser Ser Val Ser Tyr Met
                 20                  25                  30

Asn Trp Tyr Gln Gln Thr Pro Gly Lys Ala Pro Lys Leu Leu Ile Tyr
                 35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
                100                 105
```

(2) INFORMATION FOR SEQ ID NO:9:

(i) SEQUENCE CHARACTERISTICS:
        (A) LENGTH: 107 amino acids
        (B) TYPE: amino acid
        (C) STRANDEDNESS:
        (D) TOPOLOGY: linear (xi) SEQUENCE DESCRIPTION: SEQ ID NO:9:

```
Asp Ile Gln Met Thr Gln Ser Pro Ser Ser Leu Ser Ala Ser Val Gly
 1                5                  10                  15

Asp Arg Val Thr Ile Thr Cys Ser Ala Ser Ser Val Ser Tyr Met
                 20                  25                  30

Asn Trp Tyr Gln Gln Thr Pro Gly Lys Ala Pro Lys Arg Trp Ile Tyr
                 35                  40                  45

Asp Thr Ser Lys Leu Ala Ser Gly Val Pro Ser Arg Phe Ser Gly Ser
 50                  55                  60

Gly Ser Gly Thr Asp Tyr Thr Phe Thr Ile Ser Ser Leu Gln Pro Glu
 65                  70                  75                  80

Asp Ile Ala Thr Tyr Tyr Cys Gln Gln Trp Ser Ser Asn Pro Phe Thr
                 85                  90                  95

Phe Gly Gln Gly Thr Lys Leu Gln Ile Thr Arg
                100                 105
```

(2) INFORMATION FOR SEQ ID NO:10:

(i) SEQUENCE CHARACTERISTICS:
        (A) LENGTH: 119 amino acids
        (B) TYPE: amino acid (C) STRANDEDNESS:
        (D) TOPOLOGY: linear (xi) SEQUENCE DESCRIPTION: SEQ ID NO:10:

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
            115

(2) INFORMATION FOR SEQ ID NO:11:

(i) SEQUENCE CHARACTERISTICS:
        (A) LENGTH: 126 amino acids
        (B) TYPE: amino acid
        (C) STRANDEDNESS:
        (D) TOPOLOGY: linear (xi) SEQUENCE DESCRIPTION: SEQ ID NO:11:

Gln Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Ser Tyr
            20                  25                  30

Ala Met Tyr Trp Val Arg Gln Ala Pro Gly Lys Gly Leu Glu Trp Val
        35                  40                  45

Ala Ile Ile Trp Asp Asp Gly Ser Asp Gln His Tyr Ala Asp Ser Val
    50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
            100                 105                 110

Pro Asp Tyr Trp Gly Gln Gly Thr Pro Val Thr Val Ser Ser
            115                 120                 125

(2) INFORMATION FOR SEQ ID NO:12:

(i) SEQUENCE CHARACTERISTICS:
        (A) LENGTH: 119 amino acids
        (B) TYPE: amino acid
        (C) STRANDEDNESS:
        (D) TOPOLOGY: linear (xi) SEQUENCE DESCRIPTION: SEQ ID NO:12:

Gln Val Gln Leu Val Glu Ser Gly Gly Gly Val Val Gln Pro Gly Arg
1               5                   10                  15

Ser Leu Arg Leu Ser Cys Ser Ser Ser Gly Tyr Thr Phe Thr Arg Tyr

-continued

```
                20                  25                  30
Thr Met His Trp Val Arg Gln Ala Pro Gly Lys Gly Leu Glu Trp Val
        35                  40                  45
Ala Tyr Ile Asn Pro Ser Arg Gly Tyr Thr Asn Tyr Asn Gln Lys Phe
 50                  55                  60
Lys Asp Arg Phe Thr Ile Ser Arg Asp Asn Ser Lys Asn Thr Leu Phe
 65                  70                  75                  80
Leu Gln Met Asp Ser Leu Arg Pro Glu Asp Thr Gly Val Tyr Phe Cys
                85                  90                  95
Ala Arg Tyr Tyr Asp Asp His Tyr Cys Leu Asp Tyr Trp Gly Gln Gly
                100                 105                 110
Thr Pro Val Thr Val Ser Ser
            115

(2) INFORMATION FOR SEQ ID NO:13:

(i) SEQUENCE CHARACTERISTICS:
        (A) LENGTH: 119 amino acids
        (B) TYPE: amino acid
        (C) STRANDEDNESS:
        (D) TOPOLOGY: linear (xi) SEQUENCE DESCRIPTION: SEQ ID NO:13:

Gln Val Gln Leu Val Gln Ser Gly Gly Gly Val Val Gln Pro Gly Arg
  1                 5                  10                  15
Ser Leu Arg Leu Ser Cys Lys Ala Ser Gly Tyr Thr Phe Thr Arg Tyr
                20                  25                  30
Thr Met His Trp Val Arg Gln Ala Pro Gly Lys Gly Leu Glu Trp Ile
        35                  40                  45
Gly Tyr Ile Asn Pro Ser Arg Gly Tyr Thr Asn Tyr Asn Gln Lys Phe
 50                  55                  60
Lys Asp Arg Phe Thr Ile Ser Thr Asp Lys Ser Lys Ser Thr Ala Phe
 65                  70                  75                  80
Leu Gln Met Asp Ser Leu Arg Pro Glu Asp Thr Ala Val Tyr Tyr Cys
                85                  90                  95
Ala Arg Tyr Tyr Asp Asp His Tyr Cys Leu Asp Tyr Trp Gly Gln Gly
                100                 105                 110
Thr Pro Val Thr Val Ser Ser
            115

(2) INFORMATION FOR SEQ ID NO:14:

(i) SEQUENCE CHARACTERISTICS:
        (A) LENGTH: 119 amino acids
        (B) TYPE: amino acid
        (C) STRANDEDNESS:
        (D) TOPOLOGY: linear (xi) SEQUENCE DESCRIPTION: SEQ ID NO:14:

Gln Val Gln Leu Val Gln Ser Gly Gly Gly Val Val Gln Pro Gly Arg
  1                 5                  10                  15
Ser Leu Arg Leu Ser Cys Lys Ala Ser Gly Tyr Thr Phe Thr Arg Tyr
                20                  25                  30
Thr Met His Trp Val Arg Gln Ala Pro Gly Lys Gly Leu Glu Trp Ile
        35                  40                  45
Gly Tyr Ile Asn Pro Ser Arg Gly Tyr Thr Asn Tyr Asn Gln Lys Phe
 50                  55                  60
Lys Asp Arg Phe Thr Ile Ser Thr Asp Lys Ser Lys Ser Thr Ala Phe
```

-continued

```
                65                  70                  75                  80
Leu Gln Met Asp Ser Leu Arg Pro Glu Asp Thr Ala Val Tyr Tyr Cys
                    85                  90                  95
Ala Arg Tyr Tyr Asp Asp His Tyr Cys Leu Asp Tyr Trp Gly Gln Gly
                100                 105                 110
Thr Pro Val Thr Val Ser Ser
        115
```

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:15:

TCCAGATGTT AACTGCTCAC                                                       20

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (xi) SEQUENCE DESCRIPTION: SEQ ID NO:16:

CAGGGGCCAG TGGATGGATA GAC                                             23

(2) INFORMATION FOR SEQ ID NO:17:

(i) SEQUENCE CHARACTERISTICS:
        (A) LENGTH: 9 base pairs
        (B) TYPE: nucleic acid
        (C) STRANDEDNESS: single
        (D) TOPOLOGY: linear (xi) SEQUENCE DESCRIPTION: SEQ ID NO:17:

GCCGCCACC                                                                        9

(2) INFORMATION FOR SEQ ID NO:18:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:18:

```
Leu Leu Gly Gly Pro Ser
1               5
```

(2) INFORMATION FOR SEQ ID NO:19:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:19:

```
Phe Leu Gly Gly Pro Ser
1               5
```

```
(2) INFORMATION FOR SEQ ID NO:20:

(i) SEQUENCE CHARACTERISTICS:
        (A) LENGTH: 5 amino acids
        (B) TYPE: amino acid
        (C) STRANDEDNESS:
        (D) TOPOLOGY: linear (xi) SEQUENCE DESCRIPTION: SEQ ID NO:20:

Val Ala Gly Pro Ser
1               5

(2) INFORMATION FOR SEQ ID NO:21:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:21:

Leu Glu Gly Gly Pro Ser
1                   5

(2) INFORMATION FOR SEQ ID NO:22:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:22:

Ala Ala Gly Gly Pro Ser
1                   5

(2) INFORMATION FOR SEQ ID NO:23:

(i) SEQUENCE CHARACTERISTICS:
        (A) LENGTH: 6 amino acids
        (B) TYPE: amino acid
        (C) STRANDEDNESS:
        (D) TOPOLOGY: linear (xi) SEQUENCE DESCRIPTION: SEQ ID NO:23:

Ala Ala Gly Gly Pro Ser
1                   5
```

METHODS AND MATERIALS FOR MODULATION OF THE IMMUNOSUPPRESIVE ACTIVITY AND TOXICITY OF MONOCLONAL ANTIBODIES

The present application claims priority to International application number PCT/US94/06198 filed Jun. 1, 1994, under 35 U.S.C. § 371, which is a continuation-in-part of U.S. patent application Ser. No. 08/070,116 filed Jun. 1, 1993, now issued as U.S. Pat. No. 5,885,573. The entire text of each of the above-referenced disclosures is specifically incorporated herein by reference without disclaimer.

FIELD OF THE INVENTION

This invention relates generally to methods and materials for modulation of the immunological activity and toxicity of immunosuppressive agents derived from murine OKT3 used in organ transplantation and in the treatment of auto-immune diseases.

BACKGROUND OF THE INVENTION

OKT3 is a murine monoclonal antibody (mAb) which recognizes an epitope on the ε-subunit within the human CD3 complex (Salmeron, 1991; Transy, 1989; see also, U.S. Pat. No. 4,658,019, herein incorporated by reference). Studies have demonstrated that OKT3 possesses potent T cell activating and suppressive properties depending on the assay used (Landgren, 1982; Van Seventer, 1987; Weiss, 1986). Binding of OKT3 to the TcR results in coating of the TcR and or modulation, thus mediating TcR blockade, and inhibiting alloantigen recognition and cell-mediated cytotoxicity. Fc receptor-mediated cross-linking of TcR-bound anti-CD3 mAb results in T cell activation marker expression, and proliferation (Weiss, 1986). Similarly, in vivo administration of OKT3 results in both T cell activation and suppression of immune responses (Ellenhorn, 1992; Chatenoud, 1990). Repeated daily administration of OKT3 results in profound immunosuppression, and provides effective treatment of rejection following renal transplantation (Thistlethwaite, 1984).

The production of an immune response to rodent mAbs is a major obstacle to their therapeutic use. Several groups have reported attempts to circumvent this problem by reconstructing the rodent antibody genes by replacing immunogenic murine constant region sequences by the equivalent human antibody sequences (reviewed in Adair, 1992). However, in cases such as these there is still the potential to mount an immune response against the variable region. In a further extension of the procedure, the variable region framework regions have been replaced with equivalent sequences from human variable region genes. From an examination of available X-ray structures of antigen-antibody complexes (reviewed in Poljak, 1991) it is probable that only a small number of antibody residues make direct contact with antigen. Other amino acids may contribute to antigen binding by positioning the contact residues in favorable configurations and also by inducing a stable packing of the individual variable domains and stable interaction of the light and heavy chain variable domains. Antibody domains have been the subject of detailed examination. (See for example, Looney, 1986, and references therein.)

The use of OKT3 is limited by problems of "first dose" side effects, ranging from mild flu-like symptoms to severe toxicity, which are believed to be caused by lymphokine production stimulated by OKT3. Although successful reuse of OKT3 has been reported (Woodle, 1991) it is complicated by a human anti-mouse antibody (HAMA) response (OMTSG, 1985), a proportion of the response being directed to the variable region of the antibody (Jaffers, 1984). While low titre HAMA may present no significant problem, some patients do develop high titre anti-isotype and/or anti-idiotype responses. These can result in specific inactivation and/or the rapid clearance of the drug.

Reported side effects of OKT3 therapy include flu-like symptoms, respiratory distress, neurological symptoms, and acute tubular necrosis that may follow the first and sometimes the second injection of the mAb (Abramowicz, 1989; Chatenoud, 1989; Toussaint, 1989; Thistlethwaite, 1988; Goldman, 1990). It has been shown that the activating properties of OKT3 result from TCR cross-linking mediated by the mAb bound to T cells (via its F(ab')$_2$ portion) and to FcτR-bearing cells via its Fc portion) (Palacios, 1985; Ceuppens, 1985; Kan, 1986). Thus, before achieving immunosuppression, OKT3 triggers activation of mAb-bound T cells and FcτR-bearing cells, resulting in a massive systemic release of cytokines responsible for the acute toxicity of the mAb (Abramowicz, 1989; Chatenoud, 1989). Data obtained using experimental models in chimpanzees and mice have suggested that preventing or neutralizing the cellular activation induced by anti-CD3 mAbs reduces the toxicity of these agents (Parleviet, 1990; Rao, 1991; Alegre, Eur. J. Immunol., 1990; Alegre, Transplant Proc., 1990; Alegre, Transplantation, 1991; Alegre, J. Immun., 1991; Ferran, Transplantation, 1990). In addition, previous results reported in mice using F(ab')$_2$ fragments of 145-2C11, a hamster anti-mouse CD3 that shares many properties with OKTS3, have suggested that, in the absence of FcτR binding and cellular activation, anti-CD3 mAbs retain at least some immunosuppressive properties in vivo (Hirsch, Transplant Proc., 1991; Hirsch, J. Immunol., 1991).

A great need exists for nonactivating forms of anti-human CD3 mAbs for use as immunosuppressive agents.

Initial attempts to find nonactivating anti-human CD3 mAbs for use in man, involved treatment of kidney allograft recipients undergoing rejection with T10B9.1A-31, a non-mitogenic anti-TCRαβ mAb. This resulted in a reduced incidence of fever as well as neurological and respiratory side effects (Lucas, 1993; Waid, 1992; Waid, 1991). However, some T cell activation or related side effects remained perhaps due to the specificity of this antibody. In addition, being an IgM mAb, the clearance of T10B9.1A-31 is more rapid than that of OKT3 (an IgG2m mAb), thus requiring frequent injections of high doses of mAb.

Early data on the utility of chirneric antibodies (Morrison, 1984) in which the coding sequences for the variable region of the mAb is retained the coding sequences for the constant regions are derived from human antibody suggested that the HAMA response may indeed be reduced, however a HAMA response to the murine variable region could still emerge (reviewed by Adair, 1992) and more recently the humanization process has been taken further by substituting into a human antibody those amino acids in the variable regions believed to be involved in antigen binding to give a fully humanized antibody (Reichman, 1988).

A major concern is that a humanized antibody will still be immunogenic because of the presence of the non-CDR residues which need to be transferred in order to regenerate suitable antigen binding activity, in addition to any anti-paratope antibodies that may be generated. Humanized antibodies, such as CAMPATH-1H and Hu2PLAP, have been administered to patients (LoBuglio, 1989). Both of these antibodies used the rodent amino acid sequences in CDRs as defined by Kabat, 1987 along with the rodent framework residues at position 27, where the amino acid is buried, and position 30 where the residue is predicted to be solvent accessible near CDR1. In both cases no specific immune response to initial treatments with the administered antibody was noted, although responses to a second course of treatment was seen in one study using CAMPATH-1H for the treatment of rheumatoid arthritis (Frenken, 1991). There have been no reported clinical studies using humanized antibodies in which other non-CDR solvent-accessible residues have also been included in the design.

The interactions of various cell surface proteins such as T cell receptor/CD3 complex (TCR/CD3), MHC, CD8, ED45 and CD4 have been shown to be important in the stimulation of T cell responses (Floury, 1991, Swartz, 1985, Strominger, 1980, Weiss, 1988). Two of these molecules, CD4 and CD3 have been found to be physically associated on the T cell (Saizawa, 1987, Anderson, 1988, Rojo, 1989, Mittler, 1989, Dianzani, 1992). This association is critical to T cell receptor mediated signal transduction, in part due to their associated kinase and phosphates activities (Ledbetter, 1990). Molecules which can interrupt or prevent these interactions (i.e. antibodies) are currently recognized as therapeutically useful in the treatment of kidney allograft rejection (Ortho Multicenter Transplant Group, 1985). A modification of antibody treatment, one in which several of the T cell surface proteins are directly bound together by one antibody might prove useful in current immunotherapy protocols. In addition to blocking cell adhesion or cell to cell interaction, antibodies which are capable of cross-linking several cell surface proteins may result in stimulation of T cell activity or induction of aberrant signalling and thus produce modulation of the immune response (Ledbetter, 1990).

Bringing together molecules involved in T cell activation such as CD3 and CD4, or CD3 and CD8, may be a potent method for immunoactivation. Previous studies have shown that cross-linking CD3 and CD4 with heteroconjugates composed of anti-CD3 and anti-CD4 antibodies result in a greater stimulation of $Ca^{2+}$ flux than that observed with CD3 cross linked to itself or simultaneous cross-linking of CD3 and CD4 by separate reagents (Ledbetter, 1990). Similarly, cross-linking CD3 and CD8 with immobilized antibody mixtures resulted in synergistic effects on T cell proliferation and IL-2 receptor expression (Emnuich, 1986 and 1987). These studies taken together point to a critical role for the interaction of CD3 with CD4/8 in T cell activation.

The immunomodulatory effect of cross linking various T cell surface molecules can be both immunosuppressive and immunostimulatory. Linkage of CD4 with itself or other T cell surface molecules has been shown to result in a different pattern of protein phosphorylation compared to cross-linking CD3 to itself (Ledbetter, 1990). This aberrant signalling may result as a consequence of binding both CD3 and CD4 simultaneously by a single cross-linking reagent. Previous studies have shown that pretreatment of T cells with antibody to cross-link CD4 to itself before anti-CD3 treatment inhibits T cell activation and promotes apoptosis (Newell, 1990). These results would argue that a reagent that crosslinks CD4 with CD3, or other T cell surface molecules, could be a potent immunosuppressant by virtue of inappropriate signalling through the TCR/CD3 complex.

BRIEF SUMMARY OF THE INVENTION

In general, this invention contemplates the generation of anti-human CD3 mAbs with reduced activating properties as compared with OKT3. One way to acheive this is by transferring the complementary determining regions of OKT3 onto human IgG frameworks and then performing point mutations that reduce the affinity of the "humanized" anti-CD3 mAbs for FcτRs. Studies show that whereas OKT3 and the parental humanized anti-CD3 mAbs activate T cells similarly, a humanized Fc variant fails to do so. Both the Fc variant and the activating anti-CD3 mAbs induce comparable modulation of the TCR and suppression of cytolytic T cell activity. The invention further contemplates prolongation of human allograft survival with the nonactivating anti-CD3 mAbs, which retain significant immunosuppresive properties in vivo. Thus, the use of an Fc variant in clinical transplantation should result in fewer side effects than observed with OKT3, while maintaining its clinical efficacy.

The present invention further contemplates the exploitation of an experimental model in which human splenocytes from cadaveric organ donors are inoculated into severe combined immunodeficient mice (hu-SPL-SCID mice) to test the activating and immunosuppressive properties of these anti-human CD3 mAbs in vivo. Unlike injection of OKT3 or of the parental humanized mAb, administration of the Fc variant does not result in T cell activation in vivo, as evidenced by the lack of induction of surface markers of activation, and of systemic human cytokines, including IL-2.

In accordance with long-standing patent law practice, the words "a" and "an," when used to describe the invention in the specification or claims denotes "one or more" of the object being discussed.

Specific embodiments of the invention are as follows.

In one embodiment, the present invention contemplates a "humanized" version of the murine OKT3 antibody, a powerful immunosuppressive agent. In a preferred embodiment, the "humanized" monoclonal antibody of the present invention comprises a point mutation to leucine at position 234. In another embodiment, the antibody of the present invention comprises a point mutation to glutamic acid at position 235.

Preferred embodiments of the present invention include anti-CD3 monoclonal antibodies that have reduced T cell activating properties relative to murine OKT3. In some preferred embodiments, "humanized" murine OKT3 antibody having a human Fc region and a murine antigen binding region, form the basis for the production of the antibody. For example, the human Fc region can be an IgG1 or an IgG4 Fc portion. In some preferred antibodies, the human Fc region is an IgG1 portion.

In some embodiments the antibody has a mutated Fc receptor binding region, which leads to the antibody having reduced T cell activating properties relative to murine OKT3. The Fc receptor binding region is found from about position 220 to about position 250 of the antibody, and mutations within this region are anticipated to have the potential to reduce the T cell activation properties of the antibodies by disrupting the region's ability to bind to Fc. The inventors have discovered that mutations in the region spanning about position 230 to about position 240 of the "humanized" antibodies can produce particular advantages. Comparisons of antibodies that bind to Fc those that do not bind to Fc suggest that changes in this region result in anti-CD3 antibodies that do not activate T cells. For example, some of the preferred antibodies comprise a mutation at position 234, at position 235, or at both. Anti-CD3 antibodies comprising one, two, three, four, five, or more mutations at one or more of positions 230, 231, 232, 233, 234, 235, 236, 237, 238, 239, or 240, are expected to have advantages.

The purpose of the mutations is to disrupt the structure of the Fc receptor binding region. Therefore, while it is expected that mutations that insert an amino acid that differs significantly from the one that is deleted are most likely to disrupt the structure and have the desired effect, the invention is not limited to specific mutations at specific locations. For example, the inventors have had success by substituting charged amino acids such as glutamic acid for neutral amino acids such as leucine. The inventors have also had success inserting relatively general amino acids such as alanine for relatively complex amino acids such as phenylalanine. Those of skill in the art will understand the wide variety of mutations that can lead to the disruption of the region. For example, a neutral, positively, or negatively charged amino acid can be replaced with an amino acid of a different charge. Hydrophilic amino acids can replace hydrophobic amino acids, and vice versa. Large amino acids can replace small amino acids, and vice versa. An α-helix breaking, or other secondary structure disrupting, amino acid can be inserted.

In one specific embodiment of the invention the "humanized" murine OKT3 antibody is gOKT3–5. For example, the inventors have found certain advantages for monoclonal antibodies made by placing a mutation from leucine to glutamic acid at position 235 of gOKT3–5. In other specific embodiments, the "humanized" OKT3 antibody is gOKT3–7. For example, such gOKT3–7-based antibodies may comprise a mutation from phenylalanine to alanine at position 234, a mutation from leucine to alanine at position 235, or both. Certain preferred antibodies comprise a mutation from phenylalanine to alanine at position 234 and a second mutation from leucine to alanine at position 235, with a specific example being Ala-Ala-IgG4.

Interestingly, the inventors have found that a gOKT3–7 antibody having an IgG1 Fc region and mutated to have alanine at both positions 234 and 235 (gOKT3-7($\tau_4$-a/a) does not bind to complement. Specifically, this antibody does not bind to the C1q component and start the complement-mediated cascade. This result was totally unexpected and has the advantage of removing concerns about complement activation upon treatment with the antibodies. Those of skill will understand the relative difficulties that complement activation could cause in human subjects.

Other embodiments of the invention include pharmaceutical compositions comprising the claimed anti-CD3 antibodies and a physiologically acceptable carrier. The physiologically acceptable carrier can be any carrier that will allow the introduction of the claimed antibody in a therapeutic manner.

Other embodiments of the invention include methods of suppressing immune response-triggered rejections of transplanted organ tissue. These methods comprise the step of administering to an organ transplant patient, either before, during or after transplantation, a monoclonal antibody useful to modulate immunosuppressive activity. In certain preferred embodiments, the antibody is a "humanized" murine OKT3 monoclonal antibody that has a mutation. Other preferred methods for suppression of immune response-triggered rejection of transplanted organ tissue comprise the step of administering an antibody modulates immune response through binding to a first T-cell surface protein, designated CD3, and, simultaneously, to a second T-cell surface protein. For example, the second T-cell surface protein can be CD3, CD4, or CD8.

BRIEF DESCRIPTION OF THE DRAWINGS

The drawings and descriptions below form a portion of the specification.

FIG. 1A and FIG. 1B. Sequences of humanized OKT3 variable regions. FIG. 1A and FIG. 1B show the alignments of the OKT3 light chain (FIG. 1A) (SEQ ID NO:6) and the heavy chain (FIG. 1B) (SEQ ID NO:10) variable domain amino acid sequence (row 1), the variable domain sequence from the human antibodies chosen as acceptor framework (row 2), and the humanized OKT3 variable domain sequences (rows 3–5) (SEQ ID NO:8, SEQ ID NO:9, SEQ ID NO:12, SEQ ID NO:13 and SEQ ID NO:14). The CDR choices are singly underlined. Rows 3–5 show only differences from the human acceptor sequence, with the non-CDR differences shown double underlined. Dashes indicate gaps introduced in the sequences to maximize the alignment. Numbering is as Kabat et al., (1987).

FIG. 2A, FIG. 2B, FIG. 2C, FIG. 2D and FIGS. 2E–G. Amino acid and nucleotide sequence of murine OKT3.

FIG. 3A and FIG. 3B show results from separate experiments. solid squares: Orthomune® OKT3; open circles: cOKT3(λ4); closed triangles: gPLT3–1(γ4); closed circles: gOKT3–5(γ4); open squares: gOKT3–7(γ4); open triangles: mOKT4A.

FIG. 3A and FIG. 3B. FcR binding assay. FIG. 3A. Inhibition of binding of PE-coupled murine IgG2a to PcR on U937 cells by anti-CD3 mAbs. Different concentrations of the mAbs were added to the FcR-bearing U937 cell-line, previously stimulated with interferon-γ, to compete for the binding of a PE-labeled IgG2a. The data are expressed as a percent of maximal fluorescence as described in FIG. 5. FIG. 3B. Inhibition of $^{125}$I-labelled human IgG binding to human FcR on U937 cells by murine and "humanized" OKT3. FcR binding activity to FcR on U937 cells was measured using a competitive inhibition assay as described in materials and methods. The results have been normalized so that the maximum binding of $^{125}$I-huIgG in the absence of inhibitor equals 100%. In this experiment the maximum binding (2750 cpm) was 15% of the total radioactivity added. The symbols for both figures correspond to the following Abs: open triangles, OKT3; closed triangles, gOKT3–5 mAb; open squares, Leu-234 mAb; closed circles, Glu-235 mAb.

DETAILED DESCRIPTION OF THE INVENTION

I. The Invention

Figure 3A:
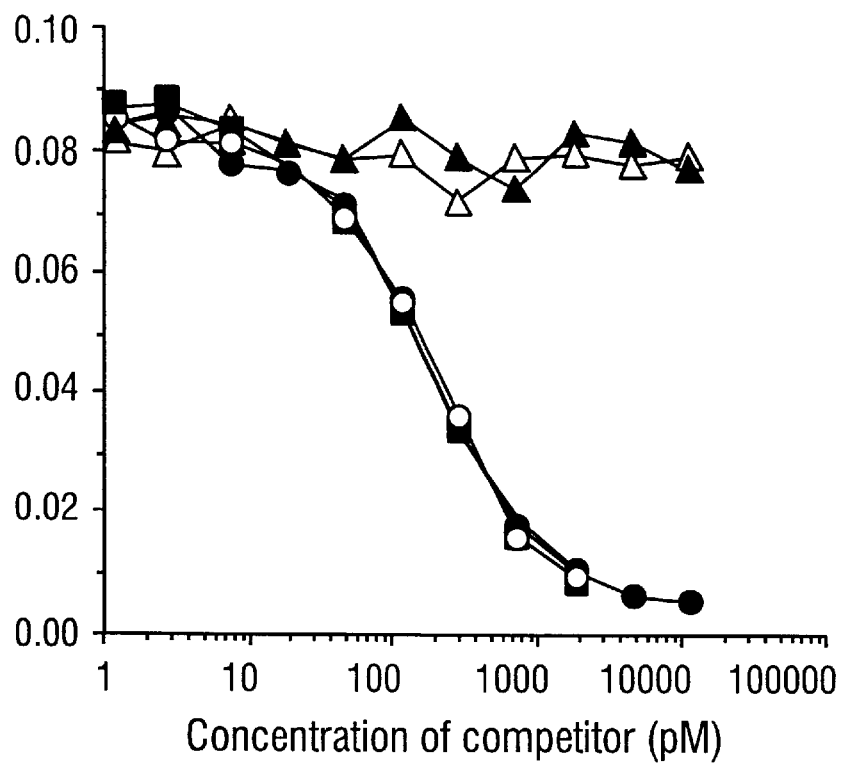
FIG. 3A and FIG. 3B. Relative Affinity Determination. Competition of OKT3 and humanized OKT3 antibodies for antigen against FITC-mOKT3. Increasing concentrations of unlabelled competitor antibody were added to a subsaturating concentration of FITC-mOKT3 tracer antibody, and were incubated with human PBMC for 1 hour at 4° C. Cells were washed and fixed, and the amount of bound and free FITC-mOKT3 was calculated. The affinities of the antibodies were each calculated according to the formula [X]–[mOKTK3]=$(1/K_x)$–$(1/K_a)$, where $K_a$ is the affinity of mOKT3, and =$K_x$ is the affinity of the competitor X. [ ] indicates the concentration of competitor at which bound/free tracer binding is $R_o/2$ and $R_o$ is maximal tracer binding (Rao, 1992).

The potent immunosuppressive agent OKT3 is a murine IgG2a mAb directed against the CD3 complex associated with the human TCR (Van Wauwe, 1980). However, the administration of OKT3 to transplant recipients induces the systematic release of several cytokines, including IL-2, IL-6, TNF-α and IFN-γ (Abramowicz, 1989; Chatenoud, 1989). This production of cytokines has been correlated with the adverse side-effects frequently observed after the first injection of OKT3 (Van Wauwe, 1980; Chatenoud, 1989; Thistlethwaite, 1988), and may augment the production of anti-isotopic and anti-idiotypic antibodies occurring in some patents after one or two weeks of treatment, then can neutralize OKT3 and preclude subsequent treatments of rejection episodes (Thistlethwaite, 1988).

Several pieces of evidence strongly suggest that these side-effects are a consequence of the cross-linking between T lymphocytes and Fc receptor (FcR)-bearing cells through the Fc portion of OKT3, resulting in activation of both cell types (Debets, 1990; Krutman, 1990): 1.) anti-CD3 mAbs did not stimulate T cell proliferation in vitro, unless the Ab was immobilized to plastic or bound to FCR+ antigen presenting cells included in the culture (van Lier, 1989); 2.) the cross-linking of OKT3 through FcRs I and II enhanced proliferation in response to IL-2, in vitro (van Lier, 1987); 3.) proliferation of murine T cells induced by 145-2C11, a hamster mAb directed against the murine CD3 complex, could be blocked by the anti-FcR Ab, 2.4G2; 4.) the injection into mice of F(ab')$_2$ fragments of 145-2C11 induced significant immunosuppression without triggering full T cell activation (Hirsch, 1990) and was less toxic in mice than the whole mAb (Alegre, 1990); 5.) the administration of an OKT3 IgA switch variant that displayed a reduced FcR-mediated T cell activation as compared with OKT3 IgG2a, resulted in fewer side effects in chimpanzees in vivo (Parleviet, 1990).

Thus, theoretically, improvement of anti-CD3 mAb therapy can be obtained by molecularly modifying OKT3 to reduce its affinity for FcRs. The mutated Ab obtained would lead to lower cellular activation and acute toxicity in vivo, but conserved immunosuppressive properties.

II. The Immune System

The immune system of both humans and animals include two principal classes of lymphocytes: the thymus derived cells (T cells), and the bone marrow derived cells (B cells). Mature T cells emerge from the thymus and circulate between the tissues, lymphatics, and the bloodstream. T cells exhibit immunological specificity and are directly involved in cell-mediated immune responses (such as graft rejection). T cells act against or in response to a variety of foreign structures (antigens). In many instances these foreign antigens are expressed on host cells as a result of infection. However, foreign antigens can also come from the host having been altered by neoplasia or infection. Although T cells do not themselves secrete antibodies, they are usually required for antibody secretion by the second class of lymphocytes, B cells.

A. T Cells

There are various subsets of T cells, which are generally defined by antigenic determinants found on their cell surfaces, as well as functional activity and foreign antigen recognition. Some subsets of T cells, such as $CD8^+$ cells, are killer/suppressor cells that play a regulating function in the immune system, while others, such as $CD4^+$ cells, serve to promote inflammatory and humoral responses. (CD refers to cell differentiation cluster; the accompanying numbers are provided in accordance with terminology set forth by the International Workshops on Leukocyte Differentiation, *Immunology Today*, 10:254 (1989). A general reference for all aspects of the immune system may be found in Klein, J. *Immunology: The Science of Self-Nonself Discrimination*, Wiley & Sons, N.Y. (1982).

1. T Cell Activation

Human peripheral T lymphocytes can be stimulated to undergo mitosis by a variety of agents including foreign antigens, monoclonal antibodies and lectins such as phytohemagglutinin and concanavalin A. Although activation presumably occurs by binding of the mitogens to specific sites on cell membranes, the nature of these receptors, and their mechanism of activation, is not completely elucidated. Induction of proliferation is only one indication of T cell activation. Other indications of activation, defined as alterations in the basal or resting state of the cell, include increased lymphokine production and cytotoxic cell activity.

T cell activation is an unexpectedly complex phenomenon that depends on the participation of a variety of cell surface molecules expressed on the responding T cell population (Leo, 1987; Weiss, 1984). For example, the antigen-specific T cell receptor (TcR) is composed of a disulfide-linked heterodimer, containing two clonally distributed, integral membrane glycoprotein chains, $\alpha$ and $\beta$, or $\gamma$ and $\delta$, non-covalently associated with a complex of low molecular weight invariant proteins, commonly designated as CD3 (the older terminology is T3) Leo, 1987).

The TcR $\alpha$ and $\beta$ chains determine antigen specificities (Saito, 1987). The CD3 structures are thought to represent accessory molecules that may be the transducing elements of activation signals initiated upon binding of the TcR $\alpha\beta$ to its ligand. There are both constant regions of the glycoprotein chains of TcR, and variable regions (polymorphisms). Polymorphic TcR variable regions define subsets of T cells, with distinct specificities. Unlike antibodies which recognize soluble whole foreign proteins as antigen, the TcR complex interacts with small peptidic antigen presented in the context of major histocompatibility complex (MHC) proteins. The MHC proteins represent another highly polymorphic set of molecules randomly dispersed throughout the species. Thus, activation usually requires the tripartite interaction of the TcR and foreign peptidic antigen bound to the major MHC proteins.

With regard to foreign antigen recognition by T cells the number of peptides that are present in sufficient quantities to bind both the polymorphic MHC and be recognized by a given T cell receptor, thus inducing immune response as a practical mechanism, is small. One of the major problems in clinical immunology is that the polymorphic antigens of the MHC impose severe restrictions on triggering an immune response. Another problem is that doses of an invading antigen may be too low to trigger an immune response. By the time the antigenic level rises, it may be too late for the immune system to save the organism.

The tremendous heterogeneity of the MHC proteins among individuals remains the most serious limiting factor in the clinical application of allograft transplantation. The ability to find two individuals whose MHC is identical is extremely rare. Thus, T cells from transplant recipients invariably recognize the donor organ as foreign. Attempts to suppress the alloreactivity by drugs or irradiation has resulted in severe side effects that limit their usefulness. Therefore, more recent experimental and clinical studies have involved the use of antibody therapy to alter immune function in vivo. The first successful attempt to develop a more selective immunosuppressive therapy in many was the use of polyclonal heterologous anti-lymphocyte antisera (ATG) (Starzl, 1967; Shield, 1979).

2. Antibody Structure

Antibodies comprise a large family of glycoproteins with common structural features. An antibody comprises of four polypeptides that form a three dimensional structure which resembles the letter Y. Typically, an antibody comprises of two different polypeptides, the heavy chain and the light chain.

An antibody molecule typically consists of three functional domains: the Fc, Fab, and antigen binding site. The Fc domain is located at the base of the Y. The arms of the Y comprise the Fab domains. The antigen binding site is located at the end of each arm of the Y.

There are five different types of heavy chain polypeptides which types are designated $\alpha$, $\delta$, $\epsilon$, $\gamma$, and $\mu$. There are two different types of light chain polypeptides designated $\kappa 0$ and $\lambda$. An antibody typically contains only one type of heavy chain and only one type of light chain, although any light chain can associate with any heavy chain.

Antibody molecules are categorized into five classes, IgG, IgM, IgA, IgE and IgD. An antibody molecule comprises one or more Y-units, each Y comprising two heavy chains and two light chains. For example IgG consists of a single Y-unit and has the formula $\alpha_2\kappa_2$ or $\alpha_2\lambda_2$. IgM comprises of 5 Y-like units.

The amino terminal of each heavy light chain polypeptide is known as the constant (C) region. The carboxyl terminal of each heavy and light chain polypeptide is known as the variable (V) region. Within the variable regions of the chains are Hypervariable regions known as the complementarity determining region (CDR). The variable regions of one heavy chain and one light chain associate to form an antigen binding site. Each heavy chain and each light chain includes three CDRs. The six CDRs of an antigen binding site define the amino acid residues that form the actual binding site for the antigen. The variability of the CDRs account for the diversity of antigen recognition.

B. Immune Response

The principal function of the immune system is to protect animals from infectious organisms and from their toxic products. This system has evolved a powerful range of mechanisms to locate foreign cells, viruses, or macromolecules; to neutralize these invaders; and to eliminate them from the body. This surveillance is performed by proteins and cells that circulate throughout the body. Many different mechanisms constitute this surveillance, and they can be divided into two broad categories—nonadaptive and adaptive immunity.

Adaptive immunity is directed against specific molecules and is enhanced by re-exposure. Adaptive immunity is mediated by cells called lymphocytes, which synthesize cell-surface receptors or secrete proteins that bind specifically to foreign molecules. These secreted proteins are known as antibodies. Any molecule that can bind to an antibody is known as an antigen. When a molecule is used to induce an adaptive response it is called an immunogen. The terms "antigen" and "immunogen" are used to describe different properties of a molecule. Immunogenicity is not an intrinsic property of any molecule, but is defined only by its ability to induce an adaptive response. Antigenicity also is not an intrinsic property of a molecule, but is defined by its ability to be bound by an antibody.

The term "immunoglobulin" is often used interchangeably with "antibody." Formally, an antibody is a molecule that binds to a known antigen, while immunoglobulin refers to this group of proteins irrespective of whether or not their binding target is known. This distinction is trivial and the terms are used interchangeably.

Many types of lymphocytes with different functions have been identified. Most of the cellular functions of the immune system can be described by grouping lymphocytes into three basic types—B cells, cytotoxic T cells, and helper T cells. All three carry cell-surface receptors that can bind antigens. B cells secrete antibodies, and carry a modified form of the same antibody on their surface, where it acts as a receptor for antigens. Cytotoxic T cells lyse foreign or infected cells, and they bind to these target cells through their surface antigen receptor, known as the T-cell receptor. Helper T cells play a key regulatory role in controlling the response of B cells and cytotoxic T cells, and they also have T-cell receptors on their surface.

The immune system is challenged constantly by an enormous number of antigens. One of the key features of the immune system is that it can synthesize a vast repertoire of antibodies and cell-surface receptors, each with a different antigen binding site. The binding of the antibodies and T-cell receptors to foreign molecules provides the molecular basis for the specificity of the immune response.

The specificity of the immune response is controlled by a simple mechanism—one cell recognizes one antigen because all of the antigen receptors on a single lymphocyte are identical. This is true for both T and B lymphocytes, even though the types of responses made by these cells are different.

All antigen receptors are glycoproteins found on the surface of mature lymphocytes. Somatic recombination, mutation, and other mechanisms generate more than $10^7$ different binding sites, and antigen specificity is maintained by processes that ensure that only one type of receptor is synthesized within any one cell. The production of antigen receptors occurs in the absence of antigen. Therefore, a diverse repertoire of antigen receptors is available before antigen is seen.

Although they share similar structural features, the surface antibodies on B cells and the T-cell receptors found on T cells are encoded by separate gene families; their expression is cell-type specific. The surface antibodies on B cells can bind to soluble antigens, while the T-cell receptors recognize antigens only when displayed on the surface of other cells.

When B-cell surface antibodies bind antigen, the B lymphocyte is activated to secrete antibody and is stimulated to proliferate. T cells respond in a similar fashion. This burst of cell division increases the number of antigen-specific lymphocytes, and this clonal expansion is the first step in the development of an effective immune response. As long as the antigen persists, the activation of lymphocytes continues, thus increasing the strength of the immune response. After the antigen has been eliminated, some cells from the expanded pools of antigen-specific lymphocytes remain in circulation. These cells are primed to respond to any subsequent exposure to the same antigen, providing the cellular basis for immunological memory.

In the first step in mounting an immune response the antigen is engulfed by an antigen presenting cell (APC). The APC degrades the antigen and pieces of the antigen are presented on the cell surface by a glycoprotein known as the major histocompatibility complex class II proteins (MHC II). Helper T-cells bind to the APC by recognizing the antigen and the class II protein. The protein on the T-cell which is responsible for recognizing the antigen and the class II protein is the T-cell receptor (TCR).

Once the T-cell binds to the APC, in response to Interleukin I and II (IL), helper T-cell proliferate exponentially. In a similar mechanism, B cells respond to an antigen and proliferate in the immune response.

The TCR acts in conjunction with a protein that is also expressed on the surface of the T-cell called CD3. The complex is the TCR-CD3 complex. Depending on the type of lymphocyte, the lymphocyte can also express other cell surface proteins which include CD2, CD4, CD8, and CD45. The interactions between these cell surface proteins are important in the stimulation of T cell response.

Two major sub-populations of T cells have been identified. CD4 lymphocytes can present on its cell surface, the CD4 protein, CD3 and its respective T cell receptor. CD8 lymphocytes can present on its cell surface, the CD8 protein, CD3 and its respective T cell receptor.

CD4 lymphocytes generally include the T-helper and T-delayed type hypersensitivity subsets. The CD4 protein typically interacts with Class II major histocompatibility complex. CD4 may function to increase the avidity between the T cell and its MHC class II APC or stimulator cell and enhance T cell proliferation.

CD8 lymphocytes are generally cytotoxic T-cells, whose function is to identify and kill foreign cells or host cells displaying foreign antigens. The CD8 protein typically interacts with Class I major histocompatibility complex.

C. Clinical Use of Antibodies

Clinical trials of the ATG treatment suggested a significant reduction of early rejection episodes, improved long term survival and, most importantly, reversal of ongoing rejection episodes. However, the results were often inconsistent due to the inability to standardize individual preparations of antisera. In addition, the precise nature of the target antigens recognized by the polyclonal reagents could not be defined, thus making scientific analysis difficult. The advent of monoclonal antibody (mAb) technology provided the bases for developing potentially therapeutic reagents that react with specific cell surface antigens which are involved in T cell activation.

One of the clinically successful uses of monoclonal antibodies is to suppress the immune system, thus enhancing the efficacy of organ or tissue transplantation. U.S. Pat. No. 4,658,019, describes a novel hybridoma (designated OKT3) which is capable of producing a monoclonal antibody against an antigen found on essentially all normal human peripheral T cells. This antibody is said to be monospecific for a single determinant on these T cells, and does not react with other normal peripheral blood lymphoid cells. The OKT3 mAb described in this patent is currently employed to prevent renal transplant rejection (Goldstein, 1987).

One unexpected side effect of the OKT3 therapy was the profound mitogenic effect of the mAb in vivo (Ellenhorn, 1988).

In addition, other cell surface molecules have been identified that can activate T cell function, but are not necessarily part of the T cell surface receptor complex. Monoclonal antibodies against Thy-1, TAP, Ly-6, CD2, or CD28 molecules can activate T cells in the absence of foreign antigen in vitro (Leo, 1989; Takada, 1984). Moreover, certain bacterial proteins although differing in structure from mAbs, also have been shown to bind to subsets of T cells and activate them in vitro (White, 1989).

The possibility of selectively down-regulating the host's immune response to a given antigen represents one of the most formidable challenges of modem immunology in relation to the development of new therapies for IgE-mediated allergies, autoimmune diseases and the prevention of immune rejection of organ transplants. Similar considerations apply to an increasing number of promising therapeutic modalities for a broad spectrum of diseases, which would involve the use of foreign biologically active agents potentially capable of modulating the immune response, provided they were not also immunogenic. Among these agents, one may cite (1) xenogeneic monoclonal or polyclonal antibodies (collectively referred to here as xIg) against different epitopes of the patients' $CD4^+$ cells (Cruse, 1989; Diamantstein 1986), administered alone or in combination with immunosuppressive drugs for the treatment of rheumatoid arthritis and other autoimmune diseases, or for the suppression of graft-versus-host reactions and the immune rejection of organ transplants (Cruse, 1989).

The therapeutic effectiveness of these immunological strategies is undermined by the patients' antibodies which prevent these bullets from reaching their target cells. In addition, the repeated administration of these agents may result in serious complications, viz. serum sickness, anaphylactic symptoms (i.e. bronchospasm, dyspnea and hypotension) and/or the deposition in the liver of toxic immune complexes leading frequently to hepatotoxicity.

D. Preparation of Monoclonal and Polyclonal Antibodies

Briefly, a polyclonal antibody is prepared by immunizing an animal with an immunogen, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies inter alia, upon the nature of the immunogen as well as the animal used for immunization. A variety of routes can be used to administer the immunogen (subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce a monoclonal antibody, mice are injected intraperitoneally with between about 1–200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

III. Immunusuppressive Modulation Through Use of "Humanized" mAbs

In order to improve the effectiveness and expand the uses of OKT3, humanized versions of the antibody have been generated. It has been shown (Woodle, 1992) that simple transfer of the loop regions and the complementarity determining regions (CDR's) (Kabat, 1987), which are believed to contain the antigen contacting amino acids, into a human framework was not sufficient in the case of OKT3 to provide the structure required for efficient antigen binding. Examination of the remaining framework residues identified several which could potentially contribute to a reconstitution of binding in a human framework. When amino acids at these positions in the human framework were replaced with those from OKT3 to give gOKT3–5, antigen binding was shown to be fully restored. Subsequently, it has been noted (Jolliffe, 1991) that a number of these amino acids derived from the OKT3 sequence are not required to achieve a humanized antibody with the same affinity as murine OKT3.

To reduce the immune responses observed in patients treated with murine OKT3, a "humanized" OKT3 (gOKT3–5), comprised of the complementary determining regions (CDR) of the murine anti-CD3 mAb and of the variable framework and constant regions of a human IgG4, was developed. However, as a therapeutic drug, an additional problem associated with OKT3, the first-dose reactions attributed to the T cell activation by the mAb, remained. Since gOKT3–5 produces, in vitro, similar activation to OKT3, it is quite likely that the same side-effects might also occur with this drug in vivo. F(ab')$_2$ fragments of OKT3 have led to potent immunosuppression and TCR modulation, in vitro. Non-activating F(ab')$_2$ fragments of anti-CD3 mAbs to mice was as efficacious as whole anti-CD3 in delaying skin graft rejection, while the F(ab')$_2$ fragments exhibited significantly reduced T cell activation and fewer side-effects in mice. However, the production of F(ab')$_2$ fragments in large quantities remains difficult. Furthermore, the half-life of this drug in the blood stream is relatively short, as compared with whole mAb. Thus, frequent injections of the F(ab')$_2$ fragments of anti-CD3 were necessary to achieve maximal immunosuppression, making the use of this mAb fragment inappropriate for clinical transplantation. Finally, recent studies have shown that even a small contaminant of whole mAb in the F(ab')$_2$ preparation ($<1/10^4$ molecules) has a synergistic effect on T cell activation.

A. Point Mutations in "Humanized" mAbs

The Fc portion of the murine IgG2a Abs, including OKT3, binds preferentially to the high affinity 72 kD FcR I (CD64) present on human macrophages and IFN-γ-stimulated polymorphonuclear leukocytes (Anderson, 1986; Lynch, 1990; Shen, 1987), but also to the low affinity 40 kD FcR II (CD32) that is found on human macrophages, B cells and polymorphonuclear neutrophils (Anderson, 1986; Petroni, 1988; Bentin, 1991). The CH2 region in the Fc portion of IgGs has been found to be the domain that selectively binds FcR I and 11 (Ollo, 1983; Woof, 1984; Burton, 1985; Partridge, 1986; Duncan, 1988). In fact, the exact binding segment has been localized to an area corresponding to amino acids 234 to 238 (Duncan, 1988) and the respective affinity of several isotypes has been determined (Gergely, 1990). Duncan et al. have shown that the mutation of a single amino acid in the FcR binding segment of a murine IgG2b, converting the sequence to that found in a murine IgG2a, resulted in a 100-fold enhancement of the binding to FcR (1988). Based on those data, a mutation was introduced into the Fc region of an anti-CD3 human IgG4 antibody resulting in a sequence similar to the low affinity sequence of the murine IgG2b. This mAb contains a glutamic acid rather than a leucine at position 235 of the human IgG4 heavy chain (Glu-235 mAb). The mutational analysis was performed on a "humanized" anti-CD3 mAb, the gOKT3–5 mAb by splicing the murine complementarily determining regions into the human IgG4 framework gene sequence. The gOKT3–5 mAb was previously shown to retain binding affinity for the CD3 complex similar to murine OKT3 and all the in vitro activation and immunosuppressive properties of OKT3. In addition, the gOKT3–5 mAb had an FcR binding sequence differing by only two amino acids from the same region on the murine IgG2b or by one amino acid in the murine IgG2a/human IgG1. Since a mutation in the FcR binding region of the mab could modify the conformation of the molecule and thus be responsible for a decrease in FcR binding regardless of the amino acid sequence obtained, we performed a control mutation of amino acid 234 from a phenylalanine into a leucine in order to mimic the FcR binding area found in the high affinity murine IgG2a and human IgGI. This mAb was designated Leu-234.

Therefore, the site-specific mutations described above were introduced into the Fc portion of the gOKT3–5 mAb to affect the binding of the Ab to FcR. The appropriate mutant of the anti-CD3 mAb was designed to exhibit the low-activating properties of F(ab')$_2$ fragments, the purity of a monoclonal antibody and an increased serum half-life as compared with F(ab')$_2$ fragments or possibly even with murine OKT3, since chimeric mouse/human antibodies have been shown to circulate longer their murine counterpart. The resulting mAb thus avoids the acute toxicity and the immunization induced by OKT3, in vivo, although, theoretically, the substitution of glutamic acid at position 235 in order to mimic murine IgG2b could also create an immunogenic epitope in the constant region of the humanized antibody.

In fact, a single amino acid substitution of a glutamic acid for a leucine at position 235 in the Fc portion of the gOKT3–5 mAb resulted in a mAb which bound U937 cells 100-fold less than the murine OKT3. This mutation, which generated an FcR binding sequence similar to the one found in murine IgG2b, resulted in a mAb with a 10-fold lower affinity for FcR than the murine IgG2b (data not shown). The reason for this difference is unclear but may imply that the interaction of the five amino acid-FcR binding region with the adjacent amino acids, which in the case of the Glu mAb are part of a human IgG4, is relevant to FcR binding.

All the Abs tested showed some modulation of the TCR after a culture of 12 hours. However, the Glu-235 mAb had to be added in higher concentrations or for a longer period of time to achieve maximal modulation. This suggests that low FcR binding might delay the induction of TCR internalization. All the Abs also inhibited CTL activity, indicating similar suppressive properties by this assay. Thus, altering the binding of the gOKT3–5 mAb by site-directed mutagenesis did not significantly affect the immunosuppressive ability of the mAb, in vitro.

The reduced binding of the Glu-235 mAb correlated with a marked decrease in the T cell activation induced by this Ab, as assessed by the absence of T cell proliferation, the decreased expression of cell surface markers of activation, the diminished release of TNF-α and GM-CSF and the lack of secretion of IFN-γ. The magnitude of T cell mitogenesis is known to correlate with the affinity of anti-CD3 mAbs for FcR I, whose relative binding is IgG1=IgG3>IgG4 for human subclasses of Abs and IgG2a=IgG3>IgGl>IgG2b for murine isotypes. The anti-CD3 mAbs employed in this study displayed an FcR binding as expected, with the human IgG4 gOKT3–5 mAb binding less avidly to U937 cells than murine IgG2a OKT3 or Leu-234 mAb, but with much higher affinity than the Glu-235 mAb.

The activation induced by the different anti-CD3 mAbs tested did not entirely correlate with their affinity for FcRs. In spite of the increased affinity of OKT3 for FcRs as compared with the gOKT3–5 mAb, no significant difference in the T cell activation was observed between the two mAbs. One explanation could be that activation is maximal whenever a certain threshold of cross-linking between T lymphocytes and FcR is attained. Another possibility is that the binding of the mAb to the CD3 antigen potentiates its avidity for FcR-bearing cells.

The extent of the functional changes generated in the FcR binding region of the gOKT3–5 mAb that form the Glu-235 mAb has further implications. The ability of certain isotypes of anti-CD3 mAbs to activate T cells and mediate ADCC has been shown to vary in the population. Murine IgG2a and IgG3 anti-CD3 mAbs are mitogenic for virtually all individuals. In contrast, murine IgG1 and IgG2b mAbs induce proliferation in only 70% and 5% to 10%, respectively. The Glu mAb, which appears to function as a non-activator IgG2b in a small fraction of the population. However, even in these individuals, IgG2b mAbs seen to trigger a different pathway of activation. For instance, in contrast to other anti-CD3 isotypes, IgG2b mAbs do not induce the production of IL-2 or IFN-γ. Thus, the proliferation observed in the small subset of the patient population may be an IL-2 independent T cell mitogenesis, which has previously been reported in other settings. More importantly, the reduced FcR binding of the Glu-235 mAb to FcR, as compared with murine IgG2b Abs, may be sufficient to abrogate the activation of even this subset of individuals.

In one embodiment, the present invention contemplates a class of homo-bifunctional antibodies, a humanized version of OKT3 which also interacts with CD4. This humanized antibody has an Fv region containing the CD3 ε antigen specificity of OKT3 and an Fc region from either human IgG1 or IgG4 antibody. The humanized anti CD3 antibody binds CD4 directly, either immobilized on plastic or on CD4$^+$, CD3$^-$, FcR cells. Initial mapping experiments suggest that the binding occurs near the OKT4A epitope on CD4. The weak interaction of some antibodies (but not human IgG4) with this region of CD4, independent of antigen/antibody binding site, has been reported (Lanert, 1991). However, unlike these reports, the antibody of the present invention binds with either a γ1 or a γ4 heavy chain. The CD4 binding site on humanized OKT3 has been mapped to the Fab fragment and probably resides in the framework sequences of the variable region.

By use of a monoclonal antibody of the present invention, specific polypeptides an polynucleotides of the invention can be recognized as antigens, and thus identified. Once identified, those polypeptides and polynucleotides can be isolated and purified by techniques such as antibody-affinity chromatography. In antibody-affinity chromatography, a monoclonal antibody is bound to a solid substrate and exposed to a solution containing the desired antigen. The antigen is removed from the solution through an immuno-specific reaction with the bound antibody. The polypeptide or polynucleotide is then easily removed from the substrate and purified.

VII. Pharmaceutical Compositions

In a preferred embodiment, the present invention provides pharmaceutical compositions comprising antibodies immunoreactive with CD3 and CD4 cell surface ntigens.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminant, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A carrier can also be a liposome. Means for using liposomes as delivery vehicles are well known in the art [See, e.g. Gabizon et al., 1990; Ferruti et al., 1986; and Ranade, V. V., 1989].

A transfected cell can also serve as a carrier. By way of example, a liver cell can be removed from an organism, transfected with a polynucleotide of the present invention using methods set forth above and then the transfected cell returned to the organism (e.g. injected intravascularly).

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Mutation in the Fc portion of the human-OKT3 mAb

Mutations of the phenylalanine in position 234 into a leucine to increase the affinity of the binding of the mAb to FcR I (Leu-234), or of the contiguous leucine (235) into a glutamic acid to reduce FcR binding (Glu-235) were performed as follows: ultracompetent CJ 236 E. coli (Invitrogen, San Diego, Calif.) were transformed with pSG5 containing the heavy chain gene of the gOKT3 mAb. The bacteria were allowed to grow in LB broth supplemented with uridine (25 mg/ml), ampicillin (100 µg/ml) until reaching an optical density of 0.35 at a wave length of 600 nm. The CJ 236 E. coli were infected with helper phage M-13 (pfu) (Stratagene) to generate uridine incorporated single stranded template. An oligonucleotide synthesized with thymidine and containing the desired mutation was then annealed to the uridine-single-stranded template to serve as a primer for the replication of the plasmid after the addition of deoxynucleotides, T7 polymerase and T4 ligase; the wild type DNA thus contains uridine, while the mutated plasmid obtained utilizes thymidine. The synthesis reaction was stopped with EDTA 0.5 M and Tris HCl-EDTA 1 M, and 10 µl were transformed into competent DH5 E. coli that degrade uridine-DNA and thus grew on ampicillin-selected media when transformed with the mutated construct. The plasmid was isolated by Qiagen minipreps; the mutated sequence in pSG5 was co-introduced with the psG5 vector containing the light chain of the mAb into COS-1 cells for transient expression of the mutant immunoglobulin.

Example 2

Generation and Identification of OKT3 Variable Region Sequences

OKT3 variable region sequences were derived from oligo-dT primed cDNA from OKT3 hybridoma cells using the Amersham International Plc. cDNA synthesis kit. The cDNA was cloned in pSP64 using EcoRI linkers. E. coli clones containing light and heavy chain cDNAs were identified by oligonucleotide screening of bacterial colonies using the oligonucleotides: 5'-TCCAGATGTTAACTGCTCAC-3'(SEQ ID NO:15) for the light chain, which is complementary to a sequence in the mouse κ constant region, and 5'-CAGGGGCCAGTGGATGGATAGAC-3'(SEQ ID NO:16) for the heavy chain, which is complementary to a sequence in the mouse IgG2a constant CH1 domain region.

The amino acid sequences for the variable regions deduced from the sequences of the cDNAs are shown in FIG. 1A (row 1) for the light chain and FIG. 1B (row 1) for the heavy chain. The CDR's are shown with the single underlining. The light chain is a member of the mouse $V_L$ subgroup VI and uses a $J_K 4$ minigene. The heavy chain is probably a member of the mouse $V_H$ subgroup II, most probably IIb, although it also has significant homology to the consensus for group Va. The D region is currently unclassified and the $J_H$ region is $J_H 2$. In terms of the loop predictions for the hypervariable regions proposed by Chothia et al., 1987, the loops can be assigned to canonical structures 1 for L1, 2 for L2 and 1 for L3, and to canonical structures 1 for H1 and 2 for H2, Chothia et al., have not yet predicted canonical forms for H3. The light chain variable region amino acid sequence shows a high degree of homology to the Ox-1 germline gene and to the published antibodies 45.2.21.1, 14.6b.1 and 26.4.1 (Sikder, 1985). The heavy chain variable region amino acid sequence shows reasonable homology to a subgroup of the J558 family including 14.6b.1. Some antibodies with these combinations of light and heavy chain genes have previously been shown to have affinity for alpha-1-6 dextran.

Example 3

Design and Construction of Humanized OKT3 Genes

The variable region domains for the humanized antibodies were designed with mouse variable region optimal codon usage (Grantham, 1986) and used the signal sequences of the light and heavy chains of mAb B72.3 (Whittle, 1987). Immediately 5' to the initiator ATG a 9-bp Kozak sequence (Kozak, 1987), 5'-GCCGCCACC-3' (SEQ ID NO: 17), was inserted. 5' and 3' terminal restriction sites were added so that the variable regions could be attached directly to the DNA sequences for the human. IgG4 and κ constant regions prior to cloning into the eukaryotic expression vectors.

The variable regions were built either by simultaneously replacing all of the CDR and loop regions by oligonucleotide directed, site-specific mutagenesis (Ollo, 1983) of a previously constructed humanized variable region for B72.3 cloned in M13 (Emtage et al.), or by assembling the sequence using synthetic oligonucleotides ranging in size from 27–67 base pairs and with 6 base overhangs. The oligonucleotides were synthesized on an Applied Biosystems Model 380B DNA Synthesizer and purified by HPLC. The oligonucleotides were enzymatically phosphorylated, paired, annealed and then equimolar aliquots of each pair were mixed and ligated. The cloning sites were exposed by restriction digestion of the ligation mixture and the correctly sized fragments were identified and cloned directly into the expression vectors, 5' to the constant regions, prior to sequencing and expression.

For the design of the humanized OKT3 variable region sequences, REI (Kabat, 1987) was chosen as the human light chain framework, and KOL was chosen for heavy chain variable region. In both cases antibodies were selected for which a structure had been determined by X-ray crystallography so that a structural examination of individual residues in the human variable region frameworks could be made. The variable region sequences of the human acceptor frameworks are shown in FIG. 1A and FIG. 1B (row 2) (SEQ ID NO:7 and SEQ ID NO: 11).

For comparison purposes, the amino acid and nucleotide sequences for murine OKT3 (SEQ ID NO:1, SEQ ID NO:2, SEQ ID NO:3, SEQ ID NO:4 and SEQ ID NO:5), as obtained from Sequences of Proteins of Immunbiological Interest 4/e (1987), are provided in FIG. 2A, FIG. 2B, FIG. 2C, FIG. 2D and FIG. 2E.

Row 3 in each of FIG. 1A (SEQ ID NO:8) and FIG. 1B (SEQ ID NO: 12) shows the sequences for the variable regions of the initial design, gL and gH. Only differences from the human acceptor sequence are shown. For gL the CDR choices were as suggested by Kabat et al., and no other non-CDR murine residues were used. For gH the OKT3 CDR's, as suggested by reference to Kabat et al., were substituted into the KOL sequence along with the murine residues at positions 27, 28 and 30 which are normally bound in a loop region adjacent to CDR1 (Chothia, 1987; 1989). The importance of residue 27 as a determiner of antigen binding was shown by Riechmann et al., (1988) in the reconstitution of binding activity of the CAMPATH-1 antibody. The residues 28 and 30 are predicted to be at the surface of the antibody and near to CDR1. Residue 29 is the same in both KOL and OKT3 (FIG. 1B) and therefore does not require to be altered.

Figure 3B:
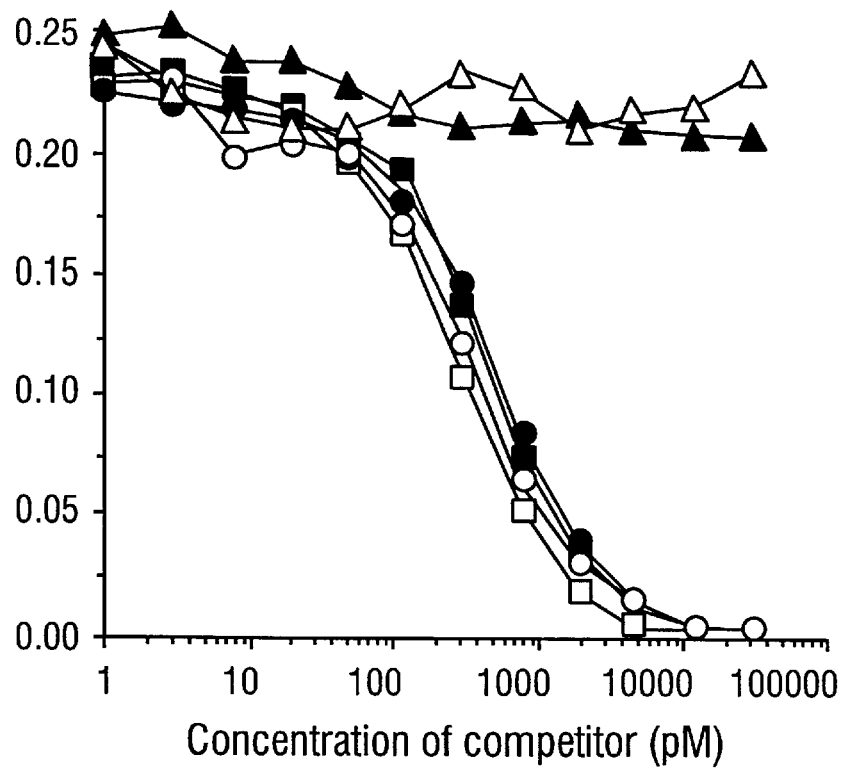

The DNA sequences coding for the initial humanized light and heavy variable regions were constructed by simultaneous replacement through site-directed mutagenesis of sequences in previously generated light and heavy chain DNAs of a humanized form of antibody B72.3. The DNA sequences coding for the humanized variable regions were then attached to the human γ-4 and κ constant region sequences and inserted into expression vectors as described for the chimeric genes. The gL and gH genes, when co-expressed in COS cells yield antibody gOKT3–1.

gOKT3–1 binds poorly to HPB-ALL cells and is not able to block the binding of mOKT3 to the cells (FIG. 3A and FIG. 3B). Therefore it was clear that further OKT3 residues outside of the CDRs needed to be considered for substitution into the humanized antibody. For the light chain these positions are at 1 and 3 which by reference to known structures for antibody variable regions are probable surface residues located near to the CDR's, residue 46 which is usually at the domain interface and the packing residue at 47, gLA has all four residues derived from the murine sequence while gLC has murine residues at positions 46 and 47 only.

Similarly, for the heavy chain, a number of locations were considered. These were at positions 23, 73 and 76 which are believed, by analogy with known antibody structures, to be partly or completely solvent exposed residues near the CDRs; at positions 6, 24, 48, 49, 71, 78 and 88 which are residues believed either to be involved in positioning of the CDRs and/or in intradomain packing, and the variable domain interface residue 91. Finally at residue 63 in CDR2, which is usually an intra-domain packing residue, the residue found in KOL was used so that potentially unfavorable contacts with other packing residues from the human framework could be avoided. A number of light and heavy chain variants were built to assess the contribution of these framework residues. It was found by experiment that residues 1 and 3 on the light chain were not required to be derived from the murine sequence, but that one or both of residues 46 and 47 should be derived from the murine sequence. FIG. 1A, row 4 (SEQ ID NO:9) shows the sequence of gLC which differs from gL by having the murine sequences at residues 46 and 47. Similarly, in the heavy chain it was found that while incorporating all of the modifications described above to give gHA (FIG. 1B, row 4) (SEQ ID NO:13), and co-expressing this gene with cL or gLC would lead to antigen binding equivalent to cOKT3 or mOKT3, some of the residues were not necessary to retain equivalent binding affinity. In particular it was found when the KOL sequences were used at positions 71, 73, 76, 88 and 91 in the gHG gene, co-expression of gHG with cL or gLC led to antigen binding equivalent to cOKT3 or mOKT3. Therefore, the binding affinity of the gLC/gHA(gOKT3-5) and gLC/gHG(gLC/gHG) combinations have been analyzed in more detail.

Large scale COS cell expression preparations were made and the humanized antibody was affinity purified by Protein A. Relative binding affinities were measured. FIG. 3A and FIG. 3B show results from two such experiments. The affinity of mOKT3 for antigen ($K_a$,) was measured to be $1.2 \times 10^9$ $M^{-1}$ by Scatchard analysis. This value for mOKT3 compares well to that of $1.3 \times 10^9$ $M^{-1}$ by Scatchard analysis. This value for mOKT3 compares well to that of $1.3 \times 10^9$ $M^{-1}$ determined previously (Gergely, 1990). In FIG. 3A, gOKTE- 5 was compared with cOKT3 and mOKT3 for competition against mOKT3. Values of $1.2 \times 10^9$ $M^{-1}$ and $1.1 \times 10^9$ $M^{-1}$ 2343 obtained for the cOKT3 and gOKT3–5 antibodies respectively.

Figure 4:
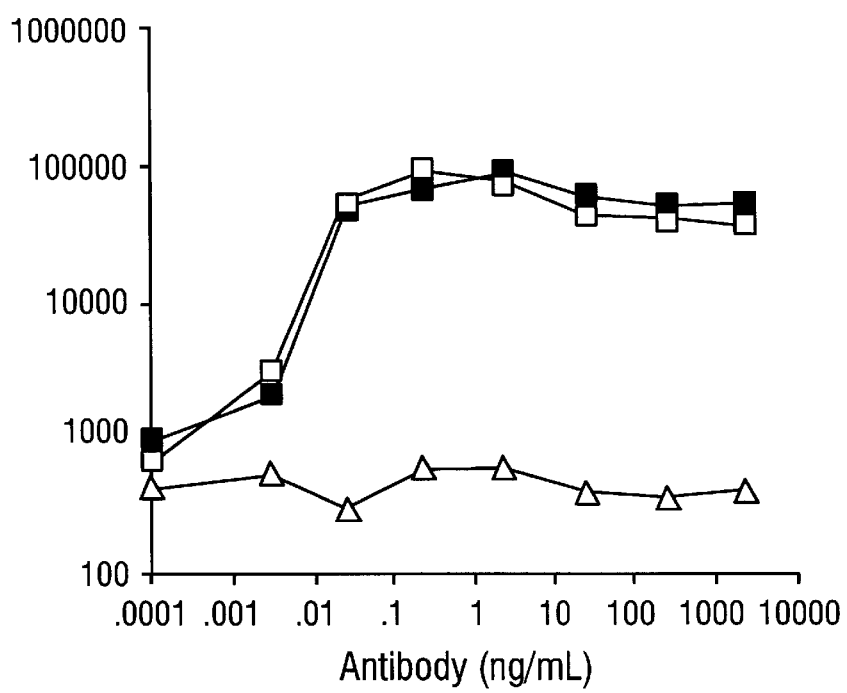
FIG. 4 Proliferation Assay. Proliferation of human PBMC to anti-CD3 antibody produced by COS cell transfection. PBMC were incubated for 68 hours in the presence of increasing amounts of anti-CD3 antibody, then pulsed with $^3$H-thymidine for an additional 4 h, and the incorporation of $^3$H-thymidine quantitated. closed squares: Orthomune® OKT3; open squares: gOKT3–7(γ4); open triangles: mOKT4A.

Subsequently, (FIG. 3B) similar results were obtained for gOKT3–7 ($K_a$ $1.4 \times 10^9$ $M^{-1}$) compared to $1.2 \times 10^9$ $M^{-1}$ for mOKT3, $1.4 \times 10^9$ $M^{-1}$ for cOKT3 and $1.1 \times 10^9$ $M^{-1}$ for gOKT3–5. These experiments show that the antigen binding activity of OKT3 has been successfully transferred to the humanized antibodies. Previous studies have indicated that mitogenic potency is a sensitive parameter of the T cell activation properties of anti-CD3 mAbs (Woodle, 1991). In an earlier study it was shown that gOKT3–5 still demonstrated mitogenic potency even in the context of an IgG4 isotype. Therefore, the activation potency of gOKT3–7 antibody was assessed by quantitating proliferating responses. gOKTE-7 demonstrated mitogenic potency equivalent to that of mOKT3 (FIG. 4). This suggests that cross-linking of the bound antibody still occurs with the γ4 isotype leading to proliferative signals. A therapeutic humanized OKT3 antibody may need further alterations to the constant region to minimize such effects.

Example 4

Construction and Expression of Chimeric OKT3 Genes

The murine cDNAs were assembled into expression vector controls for the biological function of the humanized antibodies. The murine variable region cDNA sequences were attached to human k light chain and γ4 heavy chain constant region DNA sequences following a previously described strategy to generate chimeric OKT3 (cOKT3)

genes which were then inserted into eukaryotic expression vectors. As the ultimate aim is to design a humanized OKT3 iGg antibody which can efficiently bind to CD3 while retaining useful effector pharmacokinetics and have no first dose side effects, a reduced affinity for FcR was built into the constructs by using the γ4 gene.

Small scale COS cell expression and metabolic labelling studies were as described (Whittle, 1987). Large scale COS cell expression studies were performed in roller bottles, harvesting the product supernatant 5 days after transfection. (T. Livelli, Specialty Media Inc., Lavallette, N.J.). Material from large scale transfections was purified by Protein A Sepharose chromatography. The yield of assembled antibody in COS cell supernatants was measured as described by Woodle et al., 1992. Murine OKT3, cOKT3, and murine/ chimeric hybrid antibodies expressed from COS cells were shown to bind to antigen equivalently to mOKT3 and to block the binding of MOKT3 to CD3 positive cells.

Example 5

Transient Expression of Murine and Human-OKT3 mAbs Genes

COS-1 cell expression studies were performed using reagents and procedures from a transient expression kit (Specialty media, Lavallette, N.J.) modified for use in roller bottles (T. Livelli, Specialty Media, personal communication). Product supernatants for purification of the test Abs were harvested 6 days after transfection.

ELISA assays were performed to determine the yield of assembled "humanized" antibody in COS cells supernatants. Ninety-six well plates were coated with F(ab')$_2$ goat anti-human Fc antibody. COS cell supernatants were added and incubated for one hour at room temperature and washed. Horseradish peroxidase-conjugated goat anti-human kappa chain (Caltag) was used with o-phenylenediamine (OPD) for detection. Purified human IgG was used as standard.

Example 6

Mutated "Humanized" OKT3 mAbs Bind to the CD3 Complex of T cells with the Same Affinity as Murine OKT3

The Fc portion of the gOKT3–5 mAb was mutated according to procedures described above in order to alter its binding to FcR-bearing cells. A phenylalanine was substituted for a leucine in position 234 (Leu-234), or the adjacent leucine (235) was transformed into a glutamic acid (Glu-235). The affinity of the gOKT3–5 mAb for the TCR complex was previously shown to be similar to that of OKT3 (Van Wauwe et al., 1980). Although changes in the Fc portion of the mAb should not alter Ag binding affinity, it was important to show that point mutations in the CH2 region of the Ab, close to the hinge, did not impair the binding of the Leu-234 and the Glu-235 mAbs to the CD3 antigen.

A displacement assay was performed to examine the ability of the mutated Abs to competitively inhibit the binding of murine OKT3 to human T cells. Human peripheral blood acute lymphocytic leukemia cells were re-suspended in flow cytofluorimetry (FCM) buffer at 5×10$^5$ cells/ml. Dilutions of the anti-CD3 mAbs were added and incubated at 4° C. for 1 hour. Fluorescein isothiocyanate (FITC) was dissolved in N,N-dimethyl formamide (DMF) to give a 10 mg/ml solution. FITC/DMF was added to purified mAb at 1:10 w/w and incubated at 25° C. for four hours, followed by dialysis into PBS containing an anion exchange resin (AG1-X8, 200–400 mesh, chloride form; Bio-Rad). Aggregates were removed prior to use by airfuge centrifugation (Becton-Dickinson). A fixed saturating amount of OKT3-FITC was added, and the cells were further incubated for 1 hour at 4° C., washed and analyzed by flow cytofluorimetry (FCM).

One or two-color FCM were performed using a FACScan flow cytometer, interfaced to a Hewlett-Packard 310 computer. Data analysis were performed using Consort-30 software. Logarithmically amplified fluorescence data were collected on 10,000 viable cells, as determined by forward and right angle light scatter intensity. One-color fluorescence data were displayed in histogram mode with fluorescence intensity on the x axis and cell number of the y axis. Two-color fluorescence data were displayed as contour plots with green (FITC) fluorescence on the x axis and orange (phycoerythrin) fluorescence on the y axis. All FCM staining procedures were performed at 4° C. in FCM buffer.

Figure 5:
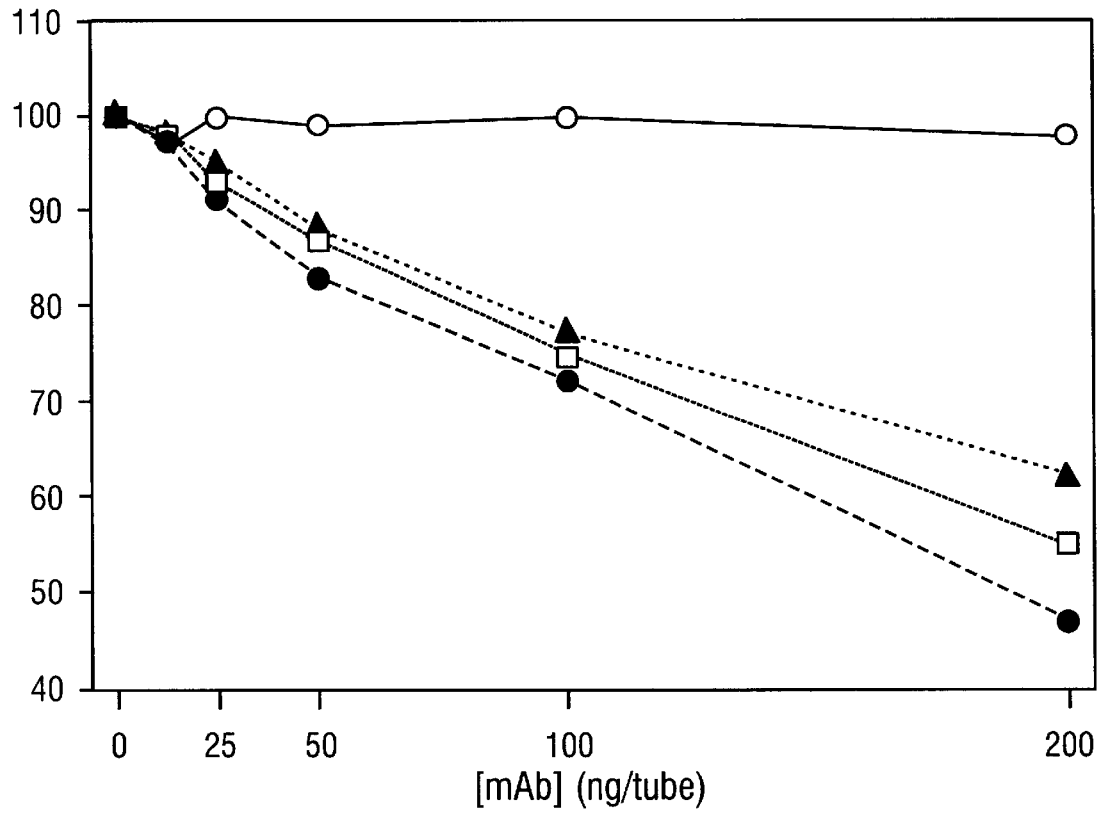
FIG. 5. OKT3 displacement assay. Serial dilutions of the "humanized" mAbs were used to competitively inhibit the binding of labeled OKT3 to the CD3 complex, as described in materials and methods. Values are expressed as a percent of the maximal fluorescence (arbitrary units attributed by the flow cytometer) achieved by binding of the labeled OKT3 alone. The symbols correspond to the following Abs: open circles, gOKT3–6 mAb; closed triangles, gOKT3–5 mAb; open squares, Leu-234 mAb; closed circles, Glu-235 mAb.

The results of this assay are shown in FIG. 5. The data is presented as % inhibition of maximal fluorescence intensity (determined by OKT3-FITC binding in the absence of blocking Ab). Both mutant Abs displayed a similar affinity for their epitope as the parental gOKT3–5 mAb. In contrast, the gOKT3–6 mAb, a different "humanized" OKT3 which has a very weak binding activity for the CD3 antigen (Van Wauwe et al., 1980), was unable to displace the OKT3 mAb. These results correlate with the data obtained previously on a panel of isotype-switch variants of murine anti-CD3 mAbs. In those studies, the anti-CD3 mAbs expressing different isotypes had a comparable avidity for the TCR complex as assessed by Scatchard analysis (Van Wauwe et al., 1980), or by precipitation of the TCR complex and cross-blocking experiments. Thus, any differences in the activation or suppressive properties of the mutated Abs could not be attributed to a modified affinity of the combining site of the anti-CD3 mAbs for T cells.

Example 7

Binding of the Mutant anti-CD3 mAbs to FcR on U937 Cells

The mutations generated in the CH2 region of the human IgG4 gOKT3–5 either mimicked the amino acid sequence of the FcR binding region of a human IgG1 (Leu-234), which has a higher affinity for human FcR I than human IgG4, or of a murine IgG2b (Glu-235) that binds weakly to FcR I but still binds to human FcR II. In order to determine the effects of those mutations on FcR binding, the FcR binding affinity of the various "humanized" OKT3 mAbs were tested on the monocytic U937 cell line that bears FcR I and II by displacement of either a PE-coupled murine IgG2a (FIG. 3A) or of a $^{125}$I-labelled human IgG1 (FIG. 3B).

The murine anti-CD5 IgG2a-PE, OKT3E IgG2b, OKT3D IgG2b, OKT3 IgG2a, and a human IgG4 Ab FITC-coupled as described supra, were used to compete for binding in the FcR binding assay. Phycoerythrin-coupled (PE) anti-CD2 and anti-CD5 used as counterstains in the activation assays were purchased from Coulter Immunology. Modulation and coating of the TCR were determined using FITC-coupled OKT3 IgG2a and OKT3D IgG2a as described below.

FcR binding assays were performed using the FcR I- and II-bearing U937 human cell line.

For competitive inhibition assay with PE-coupled murine anti-CD5 IgG2a, 30×10$^6$ cells were cultured overnight at 37° C. in complete media in the presence of 500 U/mL of human IFN-γ to enhance the expression of FcR I. The cells were washed three times with DMEM containing 25 μm HEPES, incubated for 2 hours at 37° C. in FCS-free media and washed twice in DMEM and once in flow cytofluorimetry (FCM) buffer (PBS containing 0.1% FCS and 0.1% sodium-azide). Aliquots of the anti-CD3 mAbs serially diluted in FCM buffer, were added to 96 well V-bottom tissue culture plates along with 250,000 U937 cells/well. After incubating the cells for 15 min. at 0° C., 0.3 μg of anti-CD5 was added. Displacement of Fc-mediated anti-CD3 binding was allowed to occur for 90 minutes at 0° C., after which cells were harvested and washed in FCM buffer. Fluorescence of 10,000 cells stained with the PE-anti-CD5 Ab was determined using a FACScan flow cytometer. The data was plotted in a format using Consort 30 software as described below.

For competitive inhibition assay for FeR binding with $^{125}$I-human IgG, U937 cells were washed and resuspended at a concentration of $1.4 \times 10^8$ cells/ml in the assay medium (0.2% BSA in PBS). Aliquots of $1 \times 10^6$ cells per tube were incubated for 1 h at 37° C. with $^{125}$I-labeled human IgG at a final concentration of $1 \times 10^9$ M. Murine or "humanized" OKT3 was added at final concentrations ranging from 0.023 μg/ml to 150 μg/ml, with the total volume equaling 21 82 l/tube. Following the incubation, the mixture was layered over 10% sucrose. Upon centrifugation at 11000×g for 5 min., the pelleted cells (bound $^{125}$I-huIgG) separated from the medium containing free $^{125}$I-huIgG. The tubes were then frozen in dry ice and the bottom of the tube containing the pelleted cells was removed for analysis of the bound $^{125}$I-huIgG.

The maximum binding of $^{125}$-huIgG was determined in the absence of the inhibitor. The results are expressed as a percentage of the $^{125}$I-huIgG bound in the presence of the inhibitor relative to the maximum binding. Non-specific binding is seen as the percentage bound in the presence of excess inhibitor (150 μg/ml murine OKT3). All controls and samples were assayed in triplicate tubes.

Figures 6, 7:
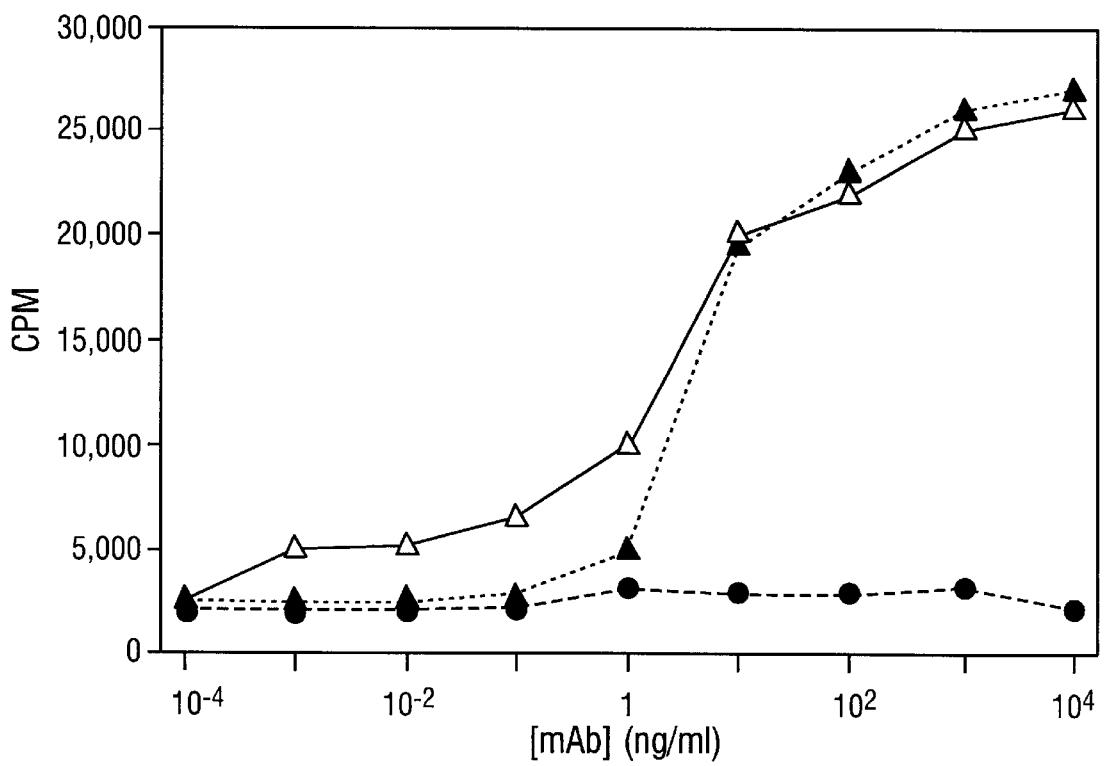
FIG. 6. N-terminal of $CH_2$ domain.
FIG. 7. Mitogenicity induced by murine and "humanized" anti-CD3 mAbs. PBMC were incubated for 72 hours with serial dilutions of the mAbs before the addition of 1 µCi/well of $H^3$ Thymidine. Proliferation is depicted as the mean counts per minute (CPM) of triplicates (SEM<10%). These data are representative of the proliferation obtained with PBMC with 3 different donors. The symbols correspond to the following Abs: open triangles, OKT3; closed triangles, gOKT3–5 mAb; closed circles, Glu-235 mAb.

The N-terminal of the $CH_2$ domain of the mutated constructs is summarized in FIG. 6.

As shown in FIG. 3A and FIG. 3B, murine OKT3 IgG2a had, as expected, the highest affinity of all the anti-CD3 mAbs tested for FcR on U937 cells. As previously shown for human IgG4 mAbs, the gOKT3–5 required a 10-fold higher concentration to achieve the same inhibition. The Leu-234 mAb, that was expected to enhance FcR binding, has consistently proven to compete more efficiency for FcR binding than the gOKT3–5 mAb. In contrast, the Glu-235mAb, bearing the FcR binding region similar to murine IgG2b, bound poorly to U937 cells, requiring a 10-fold higher concentration than the gOKT3–5 and approximately a 100-fold greater concentration than the murine OKT3 to achieve the same percent inhibition. These results indicated that, as anticipated from their respective amino acid sequence in the FcR binding domain, the rank order of binding of the mAbs to U937 cells was murine OKT3>Leu-324>gOKT3–5>Glu-235 mAb.

Example 8

Proliferation Assays

The Glu-235 mAb was tested for its ability to induce T cell proliferation. Human peripheral blood mononuclear cells (PBMC) were obtained from normal volunteers by Ficoll-hypaque density gradient centrifugation of EDTA-anticoagulated whole blood. EBV-transformed lymphoblastoid cell lines (LCL) and human histiocytoma-derived U937 cell-line were maintained in continuous culture in complete media (DMEM supplemented with 2 mM L-glutamine), 2 mM non-essential amino acids, 100 U/mL penicillin-streptomycin (Gibco), $5 \times 105$ M 2-mercapto-ethanol (Gibco) and 25 μM HEPES (Gibco) with 10% fetal calf serum (FCS, Gibco).

PBMC preparations were resuspended in complete DMEM with 1% FCS and aliquotted to 96-well round bottom tissue culture plates (Costar) at $1 \times 10^5$ cells/well. The different Abs were added to the wells by serial log dilutions in culture media. After 72 hours of culture at 37° C. in a 5% $CO_2$ incubator, 1 μCi of $^3$H-thymidine was added to each well and followed by an additional 24 hour incubation. Cells were harvested on a semi-automatic cell harvester and H-thymidine incorporation was measured in a liquid scintillation counter. All data were expressed as mean CPM of triplicate determinations.

Stimulation of PBMC with the wild-type gOKT3–5 mAb resulted in cell proliferation comparable to that observed with PBMC stimulated with murine OKT3, as shown in FIG. 7. In contrast, no proliferation was induced by the Glu-235 mAb using PBMC from 3 different donors at mAb concentrations up to 10 μg/ml, suggesting that the alteration of the FcR binding region of this mAb had impaired its mitogenic properties.

Example 9

Activation of T Cells by CDR-grafted Mutant mAbs

In order to further analyze early T cell activation events, human peripheral blood mononuclear cells (PBMC), cultured with various anti-CD3 mAbs, were assessed for cell surface expression of Leu 23 and IL-2 receptor at 12 and 36 hours incubation, respectively.

For studies involving T cell expression of activation markers, $2 \times 10^6$ PBMC were cultured for either 12 hours (Leu 23 expression) or 36 hours (IL-2 receptor expression) in 24 well tissue culture plates in the presence of varying concentrations of the mAbs.

Figure 8A:
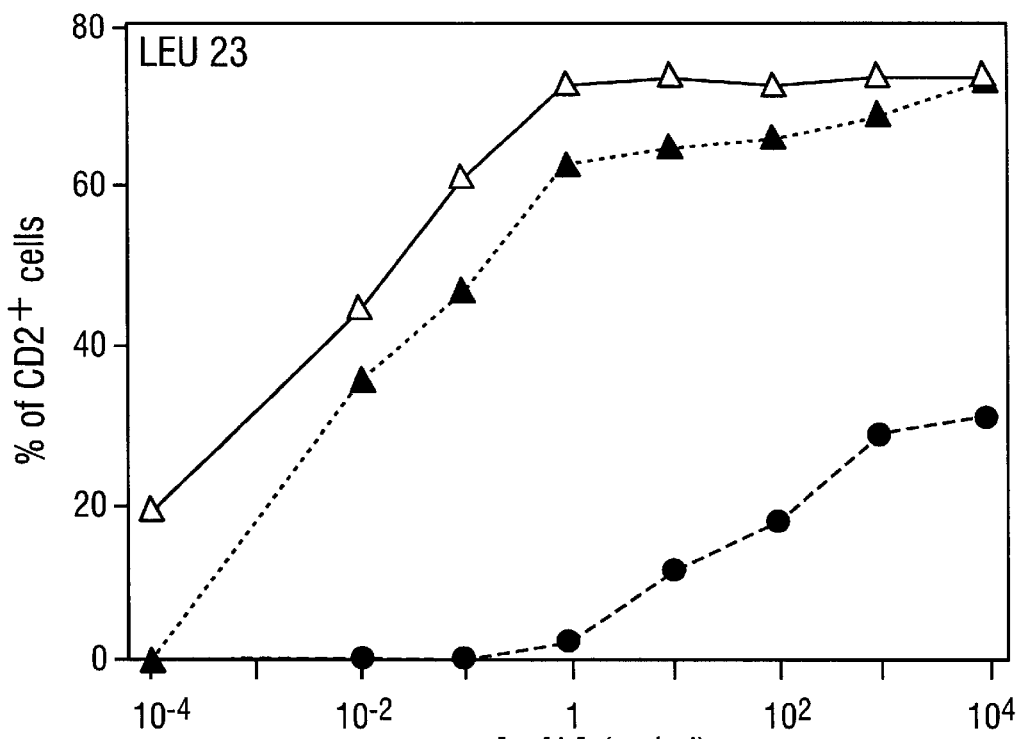
FIG. 8A and FIG. 8B. Expression of markers of activation on the surface of T cells after stimulation with murine and "humanized" OKT3 mAbs. T cell expression of Leu 23 and IL-2 receptor was determined after culture of PBMC for 12 or 36 hours respectively, in the presence of varying concentrations of the anti-CD3 mAbs. The cells were stained with FITC-coupled anti-Leu 23 or anti-IL-2 receptor mbs and the fraction of T cells (CD2 or CD5-positive cells, counterstained by PE-coupled Abs) expressing the markers of activation were determined by FCM. The symbols correspond to the following Abs: open triangles, OKT3; closed triangles, gOKT3–5 mAb; closed circles, Glu-235 mAb.
Figure 8B:
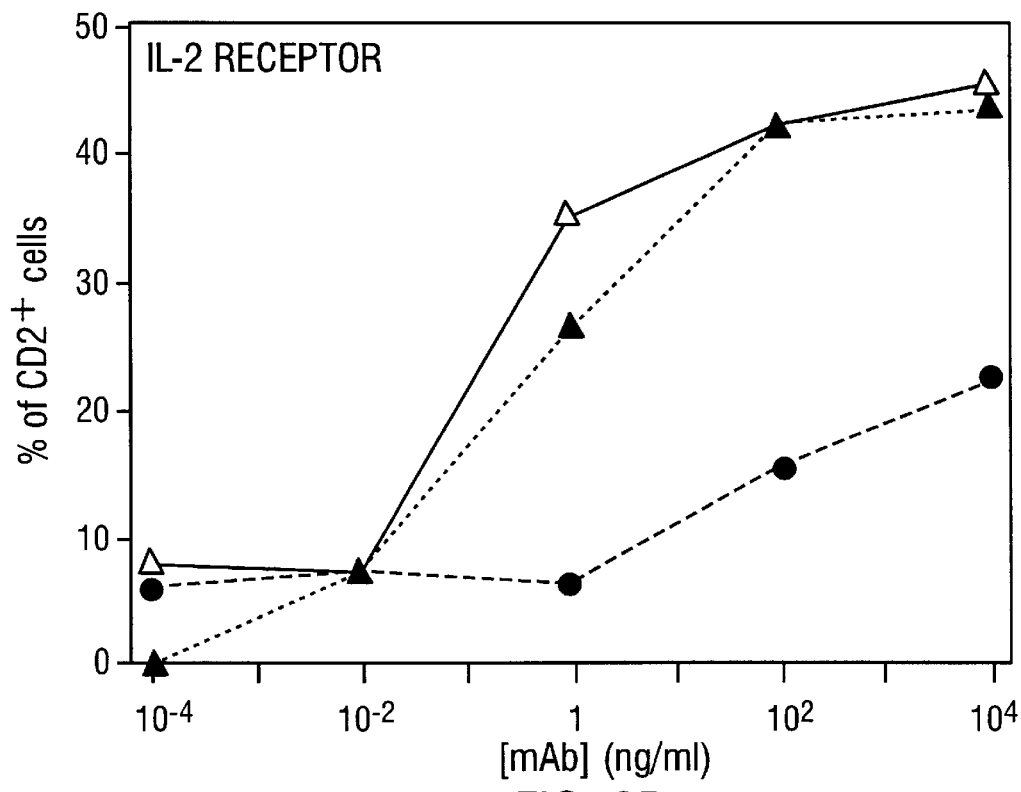

No significant differences were reproducibly observed between murine OKT3 and gOKT3–5 mAb with respect to expression of these cell surface markers (FIG. 8A and FIG. 8B). In contrast, activation by the Glu-235 mAb resulted in lower levels of expression of both markers. In fact, the highest concentration of the Ab used (10 μg/ml) achieved less than 40% of the maximal activation obtained with standard OKT3. No differences in the expression of these markers were observed between $CD4^+$ and $CD8^+$ cells (data not shown).

Example 10

IFN-γ, GM-CSF and TNF-α Production Induced by "Humanized" OKT3 mAbs

The acute toxicity observed in transplant recipients after the first administration of OKT3 has been attributed to the systematic release of lymphokines triggered by the mAb. Therefore, the in vitro production of GM-CSF, TNF-α and IFN-γ induced by the "humanized" anti-CD3 mAbs was measured. For studies involving lymphokine production, $2 \times 10^6$ PBMC were cultured in 24-well plates for either 24 hours (TNF-α) or 72 hours (GM-CSF and IFN-γ). Tissue culture supernatants were collected at the completion of the respective incubation periods and stored at −20° C. Lymphokine levels were measured via sandwich ELISA techniques using commercially available kits.

Figure 9:
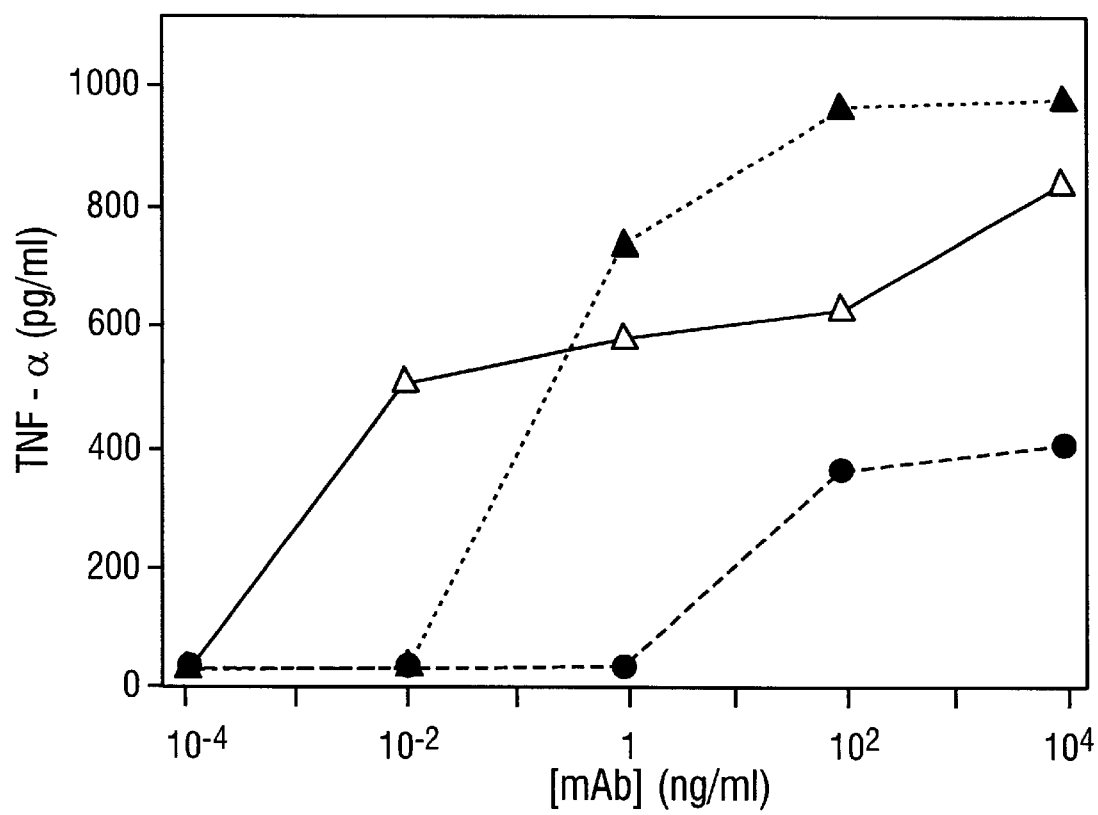
FIG. 9. Release of TNF induced by murine and "humanized" OKT3 mAbs. PBMC were cultured with serial dilutions of the different Abs for 24 hours. The concentration of TNF-α was determined by ELISA, using a commercial kit. Values are expressed as the mean of triplicates (SEM<10%). The symbols correspond to the following Abs: open triangles, OKT3; closed triangles, gOKT3–5 mAb; closed circles, Glu-235 mAb.

Similar amounts of cytokines were produced after culture of PBMC with OKT3 and gOKT3–5 mAb. In contrast, the highest concentration of the Glu-235 mAb induced small quantities of TNF-α (FIG. 9) and GM-CSF (data not shown), and no IFN-γ (data not shown).

Example 11

Induction of Modulation and Coating of the TCR Complex by Molecularly Engineered OKT3 mAbs The immunosuppressive properties of the different mAbs was compared in vitro. First, the mAbs were examined for their capacity to modulate and/or coat the TCR complex. Human peripheral blood mononuclear cells (PBMC) were incubated at $1 \times 10^6$ cells/mL for 12 hours in 24 well plates with known concentrations of anti-CD3 mAb. PBMC from each group were harvested and stained with either OKT3-FITC or OKT3D-FITC. The fluorescein-stained cells were counterstained with anti-CD5-PE to identify T lymphocytes and analyzed by flow cytofluorimetry (FCM). OKT3D-FITC was selected because of its binding to an epitope distinct from the one binding OKT3 mAb. Thus, this Ab provided a direct measurement of unmodulated surface CD3.

% CD3 Mod. =

$$\frac{\text{Control Cells MC}_{OKT3D-FITC} - \text{Ab-treated cells MC}_{OKT3D-FITC}}{\text{Control Cells}_{MCOKT3D-FITC}} \times 100$$

$$\% \text{ CD3 Coated} = \frac{\text{Ab-treated Cells MK}_{OKT3D-FITC}}{\text{Control Cells}_{MCOKT3D-FITC}} -$$

$$\frac{\text{Ab-treated Cells MC}_{OKT3-FITC}}{\text{Control Cells}_{MCOKT3-FITC}} \times 100$$

% CD3 Uncoated + Unmodulated =

100(% CD3 Coated + % CD3 Modulation)

Where MC represents the mean channel along the x-axis.

Figure 10A:
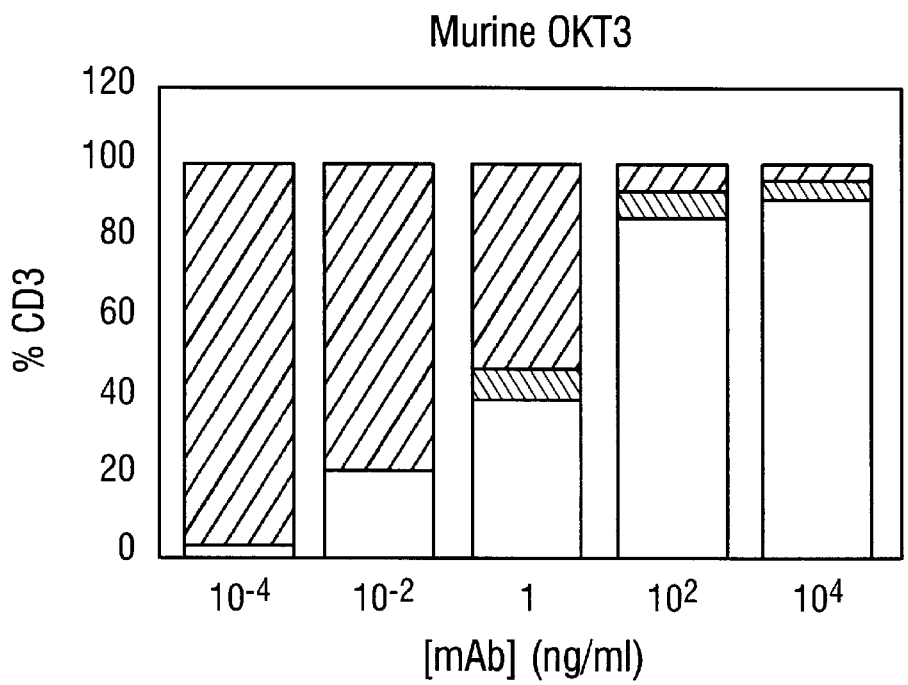
FIG. 10A, FIG. 10B and FIG. 10C. Modulation and coating of the TCR achieved by the anti-CD3 mAbs. PBMC were incubated for 12 hours with various amounts of the anti-CD3 mAbs. Coating and modulation of the TCR complex was quantitated by FCM as explained in materials and methods. T cells were counterstained with PE-coupled anti-CD5 Ab. The bottom black boxes correspond to the total percentage of CD3 complexes that are modulated, the middle grey boxes to the percentage of CD3 complexes coated by the anti-CD3 mAbs and the upper white dotted boxes to the percentage of CD3 complexes uncoated on the surface of T lymphocytes.
Figure 10B:
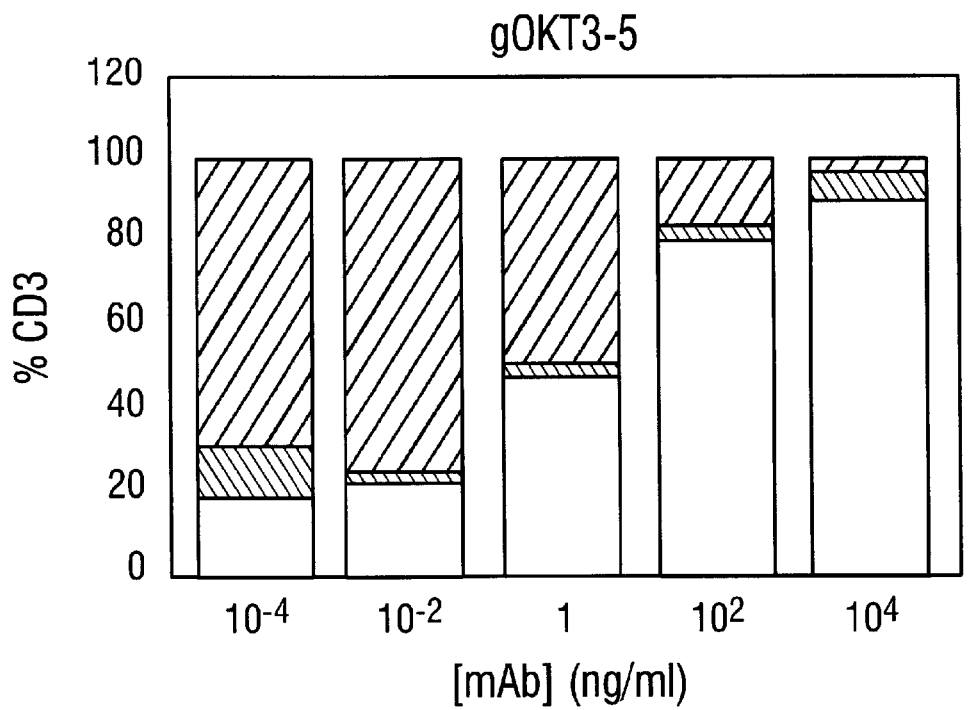
Figure 10C:
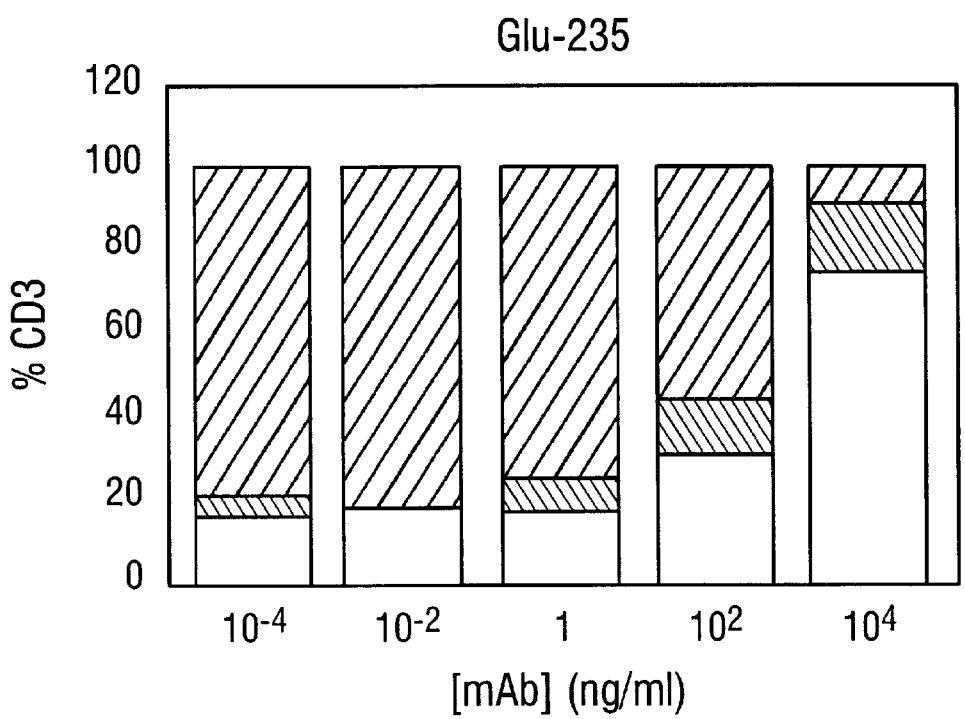

As shown in FIG. 10A, FIG. 10B and FIG. 10C, the combined modulation and coating of the TCR complex achieved by the gOKT3–5 and murine OKT3 were very similar, with half-maximal TCR blocking achieved at approximately 1 ng/ml. However, the half-maximum modulation plus coating observed with the Glu-235 mAb required a 100-fold greater concentrations of mAb (1 μg/ml) than of murine OKT3. The major difference between the Glu-235 mAb and the other Abs was due to a change in kinetics since, by 48 hours, the mAb coated and modulated the TCR complex similarly to OKT3 (data not shown). Thus, the achievement by Glu-235 mAb of internalization of the TCR, which may depend on multivalent cross-linking, was delayed as compared with the other anti-CD3 mAbs.

Example 12

Inhibition of CTL Activity by CDR-grafted Mutant mAbs

The ability of the Abs to suppress cytoxicity of alloreactive T cells was compared. HLA-A2-specific CTL were generated from a normal HLA-AI donor. Cytolytic activity was assessed on FcR negative-EBV-transformed HLA-A2 target cells. CTL were generated by a bulk allogeneic MLC technique. Normal human donors were phenotyped for HLA-A expression. Responder and stimulator combinations were selected specifically to generate HLA-A2-specific CTL effectors. Responder and stimulator PBMC were prepared by Ficoll-hypaque density gradient centrifugation as described above and resuspended in RPMI 1640 with 2 mM L-glutamine, 100 U/ml penicillin-streptomycin, 25 μM HEPES and 15%. decomplemented normal human serum. Stimulator PBMC ($1 \times 10^7$/ml) were irradiated (3000 rad) and cultured with responder PBMC ($1 \times 10^7$/10 ml) in upright 25 cm tissue culture flasks. After 7 days of culture, freshly irradiated stimulator PBMC ($4 \times 10^6$/10 ml) were added to $4 \times 10^6$/10 ml of the initial cultured cells and incubated for an additional five days. Cells were then harvested and assayed for CTL activity by $^{51}$Cr release.

HLA-A2-specific CTL effectors were generated as described above, harvested and aliquotted to a 96 well U-bottom tissue culture plate at four different effector/target ratios. Effectors were pre-incubated with serial dilutions of each anti-CD3 mAb for 30 min. Following incubation with mAbs, $^{51}$Cr-labeled Fc receptor negative-target cells [HLA-A2 expressing LCL line (Z2B) or HLA-A1 expressing LCL line (G12B) used as a non-specific target] were added. Spontaneous lysis was measured by incubation of targets alone in media and maximal lysis was achieved by addition of 0.05 N HCl. Effectors and targets were co-cultured; supernatant aliquots were harvested and radioactivity was measured in a gamma-counter.

Figure 11:
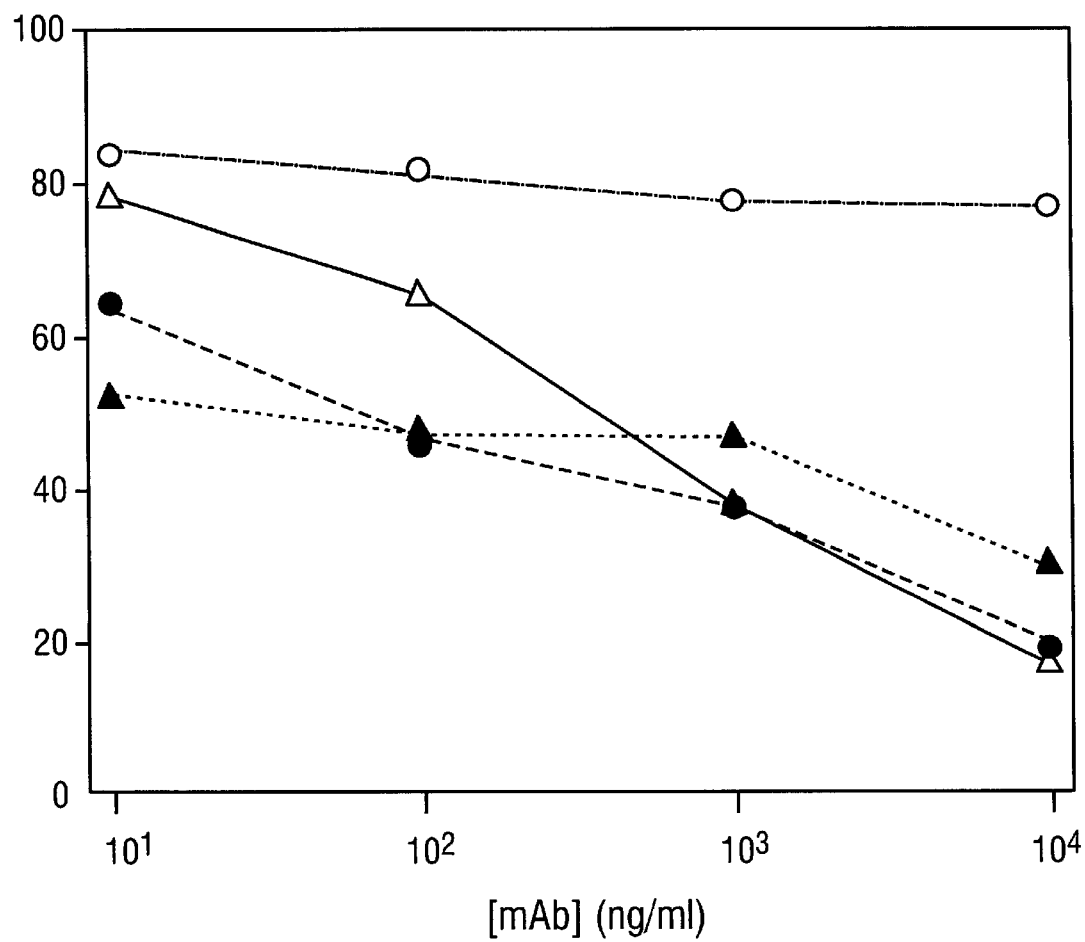
FIG. 11. Inhibition of T cell cytotoxic activity by "humanized" OKT3 mAbs. HLA A2-specific effector CTLs were generated by secondary mixed lymphocyte culture. Lysis of an A2-expressing LCL target was quantitated by a $^{51}Cr$-release assay. Values are expressed as percent of maximum specific lysis. (Maximum specific lysis was determined to be 60% of the maximum lysis observed with 0.1 M HCl). Results represent the mean of triplicates (SEM<10%). The symbols correspond to the following Abs: open circles, gOKT3–6 mAb; open triangles; OKT3; closed triangles, gOKT3–5 mAb; closed circles, Glu-235 mAb.

T cell cytotoxicity was specific as demonstrated by the absence of lysis of a syngeneic HLA-A1 EBV-transformed cell-line (data not shown). Inhibition of lysis by anti-CD3 mAbs previously has been attributed to the inability of the T cells to recognize their targets, due to TCR blockade by the mAb. In the present study, murine OKT3, gOKT3–5 mAb and Glu-235 exhibited a comparable inhibitory effect on the cytolytic activity of the alloreactive T cells. These results suggest that the ability of the different mAbs to coat the TCR within the 30 min incubation time was similar (FIG. 11). In contrast, the gOKT3–6 mAb, a "humanized" OKT3 that has a significantly reduced binding activity for the CD3 antigen, did not inhibit CTL activity. These results suggest that modified affinities for FcRs do not alter the immunosuppressive property of the anti-CD3 mAbs, in vitro.

Example 13

CD4 Modulation Studies

PBMCs isolated from Ficoll-Hypaque density gradient centrifugation were incubated at $1 \times 10^6$ cell/ml with known concentrations of OKT3 antibodies at 37° C. for 24 hours. The cells were harvested and stained with FITC-OKT4. The cells were counterstained with PE-labelled anti-CD5 (PE-Leu1, Becton Dickinson Immunocytometry Systems, San Jose, Calif.) to distinguish T lymphocytes from other PBMCs, and analyzed by FACScan. Data from the resulting studies are reported in FIG. 1A and FIG. 1B (Transy, 1989).

Results were calculated using the following formulae:

$$\% \text{ Specific lysis} = \frac{\text{Experimental CPM} - \text{Spontaneous CPM}}{\text{Maximal CPM} - \text{Spontaneous CPM}}$$

$$\% \text{ Maximal specific lysis} = \frac{\% \text{ Specific lysis}_{[mAb]}}{\% \text{ Specific lysis}_{Control}}$$

Where % Specific lysis$_{[mAb]}$ represents the CPM obtained at a given mAb concentration for a E:T ratio of 25:1 and %

Specific lysis$_{Control}$ represents the CPM obtained in the absence of mAb at the same E:T ratio. Results were expressed as the mean of triplicates.

% CD4 modulation was calculated as follows:

$$\frac{\text{Control MCN}_{FITC-OKT4} - \text{Ab-treated MCN}_{FITC-OKT4}}{\text{Control MCN}_{FITC-OKT4}} \times 100$$

Figure 12A:
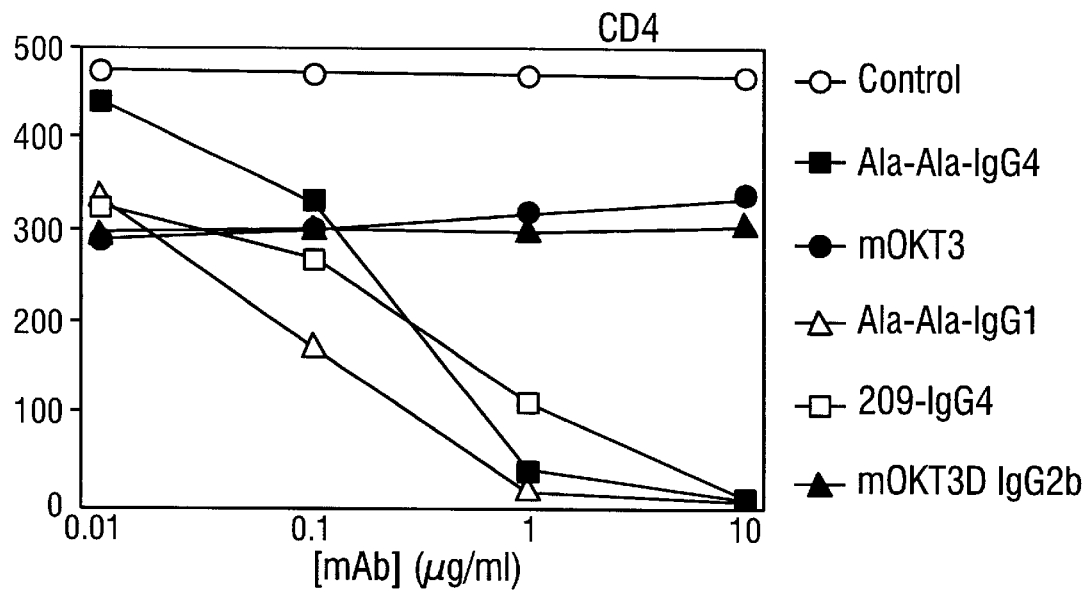
FIG. 12A and FIG. 12B. Variations of mean fluorescence of CD4 and CD8 surface markers induced by anti-CD3 mAbs.
Figure 12B:
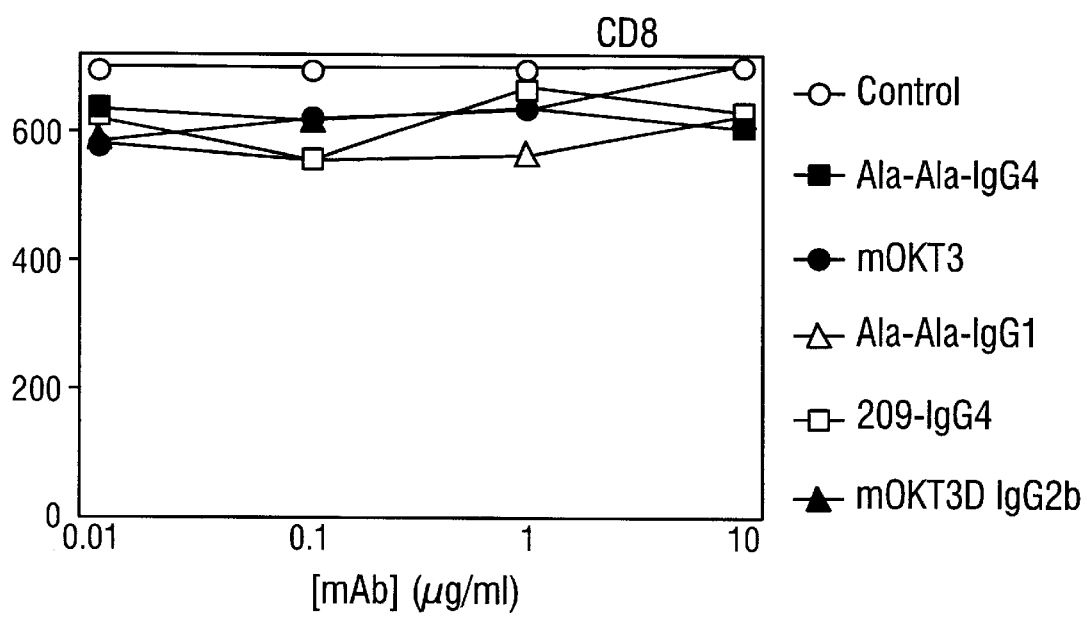

The data in the left plot of FIG. 12A and FIG. 12B reveal that the humanized antibodies studied induce the modulation of CD4 in a dose-dependent manner. In contrast is the data for mOKT3 (solid circles), the antibody from which the humanized and mutated antibodies were constructed, had no effect on CD4, as indicated by a straight line plot between antibody concentrations of from 0.01 to 0.10 μg/ml. The same can be said for the mOKT3D IgG2b antibody (solid triangles) which has also been neither humanized nor mutated. The right plot indicates that, as expected, there is no modulation of CD8 for any of the antibodies studied.

Example 14

ELISA and RES-KW3 Studies of CD4 Binding

RES-KW3 cells were washed with PBS+0.2%BSA+0.1% sodium azide (staining buffer), and first incubated with various concentrations of OKT3 antibodies for 1 hour on ice. The cells were washed three times with cold staining buffer, and FITC-labelled goat anti-human or goat anti-mouse antibodies were added (Caltac Lab. So. San Francisco, Calif.). The cells were incubated on ice for another hour before being washed and subject to FCM.

FCM was performed using a FACScan (Becton-Dickinson Immunocytometry Systems, Mountain View, Calif.) flow cytometer interfaced to a Hewlett-Packard 340 computer, data analyzed using Iysis II software (Becton Dickinson). Fluorescence data were collected using logarithmic amplification on 10,000 viable cells as determined by forward and right angle light scatter intensity. One-color fluorescence data were displayed in histogram mode with fluorescence intensity on the x axis and relative cell number on the y axis.

HIVgp 120/CD4 receptor EIA coated microplates from DuPont were used in the CD4 binding assay. 100 μL/well of CDR-grafted OKT4AIgG1 at various concentrations (1:2 dilution at starting concentration of 50 ng/ml) was added into the wells duplicate for the construction of standard curve. 100 μL/well of OKT3 antibody samples at various dilutions wee then added. The diluent is PBS+10% calf serum+0.05% Tween-20. The plates were incubated at room temperature for 2 hours.

The plates were washed with PBS+0.05% Tween-20 six times before 100 μL/well of 1:15000 diluted HRPO-conjugated goat anti-human x(f+B) antibodies in diluent was added. The plates were incubated at room temperature for another 2 hours. The plates were washed six times again, and 100 μL/well of the OPD/hydrogen peroxide solution (five 2-mg OPD tablets were added in 13 mL of Mili-Q water; after they were dissolved, 5 μL of 30% hydrogen peroxide were then added) was added into each well. The plates were incubated at room temperature in the dark for 30 min., and 50 μL/well of 2.5 N HCl was added to stop the reaction. The plates were then read at 490 nm.

Figure 13:
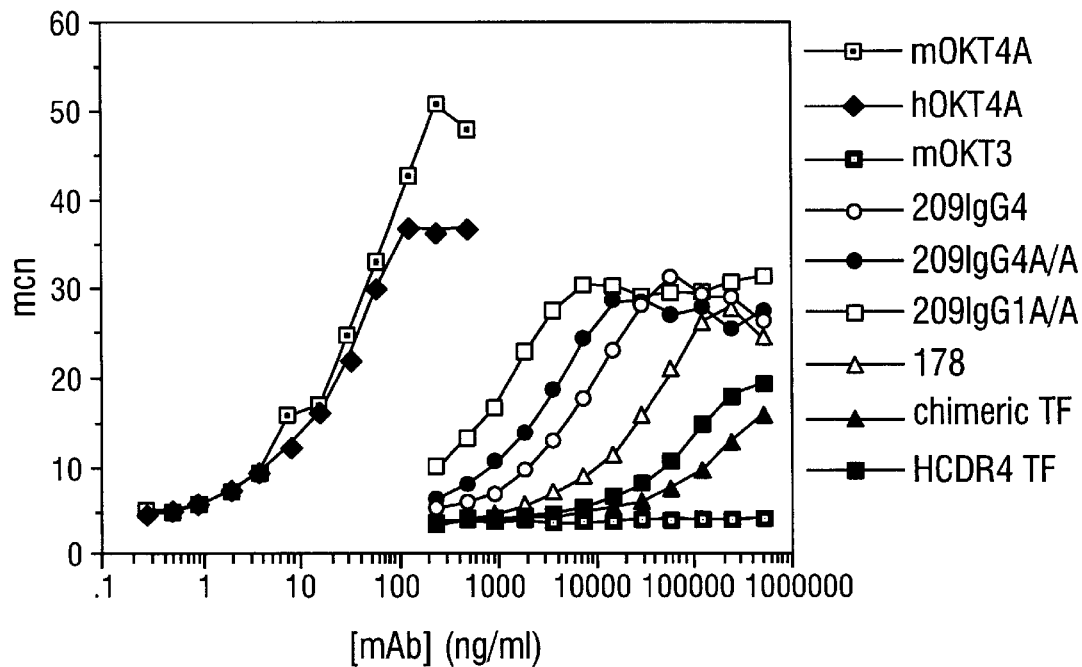
FIG. 13. CD4 binding to RES-KW3 cells.
Figure 14:
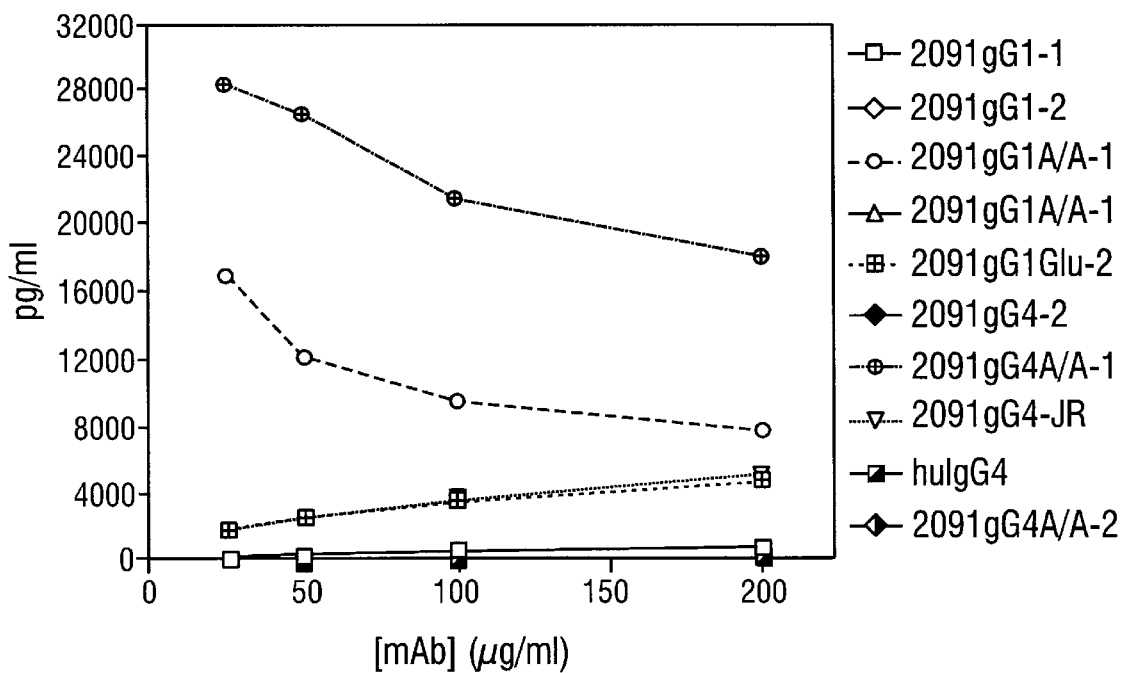
FIG. 14. CD4 binding on ELISA plates.

The resulting data are reported in FIGS. 13 and 14. These data indicate that the humanized OKT3 binds to CD4, either immobilized to ELISA plates or bound to the surface of RES-KW3 cells. It will be appreciated by one skilled in the art that data such as that indicated in FIG. 3A and FIG. 3B for 209IgG1A/A-1 (open circles) are unexpected, and suggest that divalent binding (binding to both CD3 and CD4, for example), is needed for stable attachment of this antibody to the plate.

Example 15

Generation of a Non-Activating Anti-CD3 mAb Based on gOKT3-7

To generate an anti-human CD3 mAb with an improved therapeutic index, the inventors have developed a panel of "humanized" anti-CD3 mAbs derived from OKT3, by molecularly transferring the complementary determining regions (CDRs) of OKT3 onto human IgG1 and IgG4 molecules (Woodle et al., 1992; Adair et al., submitted for publication). In addition, the inventors examined whether immunosuppression can be achieved by anti-CD3 mAbs in the absence of the initial step of cellular activation. The "humanized" mAb, formally named gOKT3-7($\tau_1$), abbreviated 209-IgG1, that has a high affinity for human FcτRs was shown, in vitro, to have similar activating properties to OKT3 (Alegre, 1992; Xu et al., manuscript in preparation) and would therefore be expected to induce in patients the acute toxicity associated with lymphokine release by activated T cells and RcτR-bearing cells. A second mAb, formally named gOKT3-7($\tau_4$-a/a); abbreviated Ala-Ala-IgG4, was developed with 2 amino acid substitutions in the $CH_2$ portion (from a phenylalanine-leucine to an alanine-alanine at positions 234–235) of the "humanized" gOKT3-7 ($\tau$4) (209-IgG4) mAb. These mutations significantly reduced binding of the mAb to human and murine FcτRI and II and led to markedly reduced activating characteristics in vitro (Alegre, 1992; Xu et al., manuscript in preparation). Importantly, this variant mAb retained the capacity to induce TCR modulation and to prevent cytolysis in vitro (Xu et al., manuscript in preparation), and thus represents a potential new immunosuppressive therapeutic agent.

Severe combined immunodeficient (SCID) mice carry an autosomal recessive, spontaneously arising mutation that results in the inability to successfully rearrange immunoglobulin and TCRs. These animals are therefore devoid of T and B lymphocytes (McCune, *Annu. Rev. Immun.,* 1991; McCune, *Curr. Opin. Immun.,* 1991; Bosma, 1983; Bosma, 1991). The inventors have recently developed a model in which lightly irradiated SCID mice are injected with human splenocytes from cadaveric organ donors (Alegre et al., manuscript submitted). These hu-SPL-SCID mice maintain functional human T cells capable of responding to mitogens and alloantigens in vitro, and of acutely rejecting human foreskin allografts in vivo. In the present study, the inventors have utilized hu-SPL-SCID mice to assess the immunosuppressive properties of the non-activating "humanized" anti-CD3 mAbs in vivo.

Materials and Methods

| Abbreviations. | |
|---|---|
| Ala-Ala-IgG4 | gOKT3-7($\tau_4$a/a) |
| FCM | flow cytometry |
| GVHD | graft-versus-host disease |
| IP | intraperitoneal |
| PE | Phycoarythrin |

-continued

| Abbreviations. | |
|---|---|
| 209IgG1 | gOKT3-7(τ1) |
| 209IgG4 | gOKT3-7(τ4)) |
| SCID | severe combined immunodeficient |

Mice. Homozygous C.B-17 scid/scid (SCID) H-$2^d$ founder mice were obtained from Dr. M. Bosma (Fox Chase, Phila, Pa.) and were subsequently bred in the specific pathogen-free animal barrier facility at the University of Chicago.

Antibodies. 145-2C11, a hamster anti-mouse CD3 mAb, was purified from hybridoma supernatant using a protein A column (Sigma, Saint Louis, Mo.), as previously described (Leo, 1987). OKT3, 209-IgG1 and Ala-Ala-IgG4 were generated as described below. Phycoerythrin (PE)-coupled anti-human CD4 and CD8, as markers of T cells, were obtained from Coulter Immunology (Hialeah, Fla.). The fluorescein isothiocyanate (FITC)-coupled anti-CD69, an early marker of T cell activation, was purchased from Becton Dickinson (San Jose, Calif.). All anti-human Abs were tested to exclude cross-reactivity on murine cells.

Generation and function of "humanized" anti-CD3 mAbs. Permanent myeloma transfectants of the murine and human-OKT3 mAbs genes were developed as previously described (Xu et al., manuscript in preparation). Mutation of the phenylalanine-leucine sequence at position 234–235 into alanine-alanine to decrease the affinity of the mAb for human and murine FcτRI and II were performed as previously described (Alegre, 1992; Xu et al., manuscript in preparation). ELISAs using a combination of goat anti-human Fc and kappa Abs were performed to determine the yield of assembled "humanized" antibody in COS cell supernatants or permanently transfected myeloma cell-lines (Woodle, 1992).

For T cell proliferation assays, PBMCs, in complete medium (RPMI-1640 plus 10% FCS), were incubated at $1 \times 10^6$ cells/ml (final volume=200 μl) with serial log dilutions of each antibody in 96-well flat-bottom microtiter plates (Costar, Cambridge, Mass.) for three days at 37° C. All mAbs samples were airfuged at >30 psi for 20 min. prior to the assay to remove preformed aggregates (Beckman, Carlsbad, Calif.). $^3$H-Thymidine (NEN-DuPont, Wilmington, Del.) was added at 1 μCi/well and the plates were incubated for additional 4 hours before harvesting. The cells were harvested in an automatic 96-well cell harvester (Tomtec, Orange, Conn.) and 3H-thymidine incorporation was measured with a Betaplate Liquid Scintillation Counter (Pharmacia).

Construction and treatment of hu-SPL-SCID mice. Fresh human spleens were obtained from cadaveric organ donors, under a protocol approved by the University of Chicago Institutional Review Board. A single cell suspension was prepared as previously described (Alegre et al., manuscript submitted). Briefly, 4 to 6 week-old SCID mice were γ-irradiated (200 rad), prior to the intraperitoneal (ip) injection of $10^8$ cells/mouse. The percentage of human cells in the peripheral blood was determined by flow cytometry (FCM). First, the peripheral blood mononuclear cells (PBMCs) were incubated (15 min.) with unlabelled murine IgG antibodies to block subsequent FcτR binding. Next, the cells were stained with PE-coupled anti-murine class I (PharMingen, San Diego, Calif.) and counterstained with FITC-coupled anti-human CD45 mAb (Coulter Immunology, Hialeah, Fla.) to identify the population of human cells. The proportion of human cells is expressed as a percentage of the total number of cells. The animals bearing between 5 and 20% human cells in the PBMCs were selected for further experiments. Mice, matched for their level of engraftment of human cells in the peripheral blood, received either PBS (1 ml), 145-2C11, OKT3, 209-IgG1 or Ala-Ala-IgG4 (100 μg resuspended in 1 ml of PBS, unless stated otherwise in the text), intraperitoneally (ip) 11 days to 3 weeks after the injection of the human splenocytes.

Detection of circulating anti-CD3 mAbs. SCID and hu-SPL-SCID mice were bled by retroorbital venous puncture 24 h, 48 h and 1 week after the injection of the mAbs (100 μg ip). The serum titers of the anti-CD3 mAbs were determined by FCM analysis using human PBMNs obtained from EDTA-anticoagulated whole blood of normal volunteers and isolated by Ficoll-Hypaque (Lymphoprep, Nycomed, Oslo, Norway) density gradient centrifugation. Six concentrations of purified OKT3, 209-IgG1 and Ala-Ala-IgG4 in 3-fold dilutions were used to generate standard curves. Human PBMCs were incubated with 3 serial dilutions of each serum (1:10, 1:30 and 1:90), and then stained with FITC-coupled goat anti-mouse Ig (Boehringer-Mannheim, Indianapolis, Ind.) for detection of OKT3, and with goat anti-human Ig (Caltag Laboratories, San Francisco, Calif.) for detection of the humanized antibodies. Serum levels were extrapolated from the mean fluorescence of anti-CD3 stained cells, as compared with a corresponding concentration of the purified anti-CD3 mAbs on the standard curves.

Detection of circulating IL-2. Sera obtained from SCID and hu-SPL-SCID mice 2 h after anti-CD3 or control treatment were analyzed for the presence of IL-2 was analyzed using a colorimetric assay that utilized the IL-2/IL-4-dependent cell line, CTLL-4, as previously described (Mosmann, 1983). CTLL-4 cells proliferated similarly to recombinant murine and human IL-2, and responded to murine but not human IL-4. To exclude participation of murine cytokines in the proliferation observed, an anti-murine IL-4 mAb, [11B11 (Ohara, 1985)], and an anti-murine IL-2 mAb, [S4B6, (Cherwinski, 1987)], were added to selected wells at concentrations found to block proliferation of CTLL-4 cells to murine IL-4 and IL-2, respectively, but not to human IL-2.

Skin grafting. Neonatal human foreskin was grafted on SCID and hu-SPL-SCID mice 11 days after the inoculation of human splenocytes. Mice were anesthetized with 60 μg/ml of chlorohydrate (120 μl delivered ip) (Sigma, St. Louis, Mo.) and intermittent inhalation of hydroxyflurane (Metophane, Pitman-Moore, Mundelein, Ill.). Skin grafts were positioned on the dorsal thorax of the mice. Each foreskin was used to graft 4 animals, each from a different group (SCID, PBS-treated, 145-2C11-treated and anti-CD3-treated hu-SPL-SCID mice). Mice received OKT3, 209-IgG1, Ala-Ala-IgG4 or 145-2C11 (50 μg/day for 5 days, followed by 10 μg/day for 10 days) diluted in 1 ml of PBS, or 1 ml of PBS alone. The grafts were unwrapped at 7 days and the status of the graft was scored blindly and independently by 2 investigators daily for the first 30 days, and once a week afterwards. The scores ranged from 0 to 4: grade 0 represented skin grafts intact and soft; grade 1, skin grafts with a modified pigmentation in a small area; grade 2, soft skin grafts with larger areas of depigmentation; grade 3, those hardened or slightly scabbed; grade 4, shrinking or scabbing skin grafts. Rejection was recorded when scores were grade 3 or greater.

Results

Figure 15:
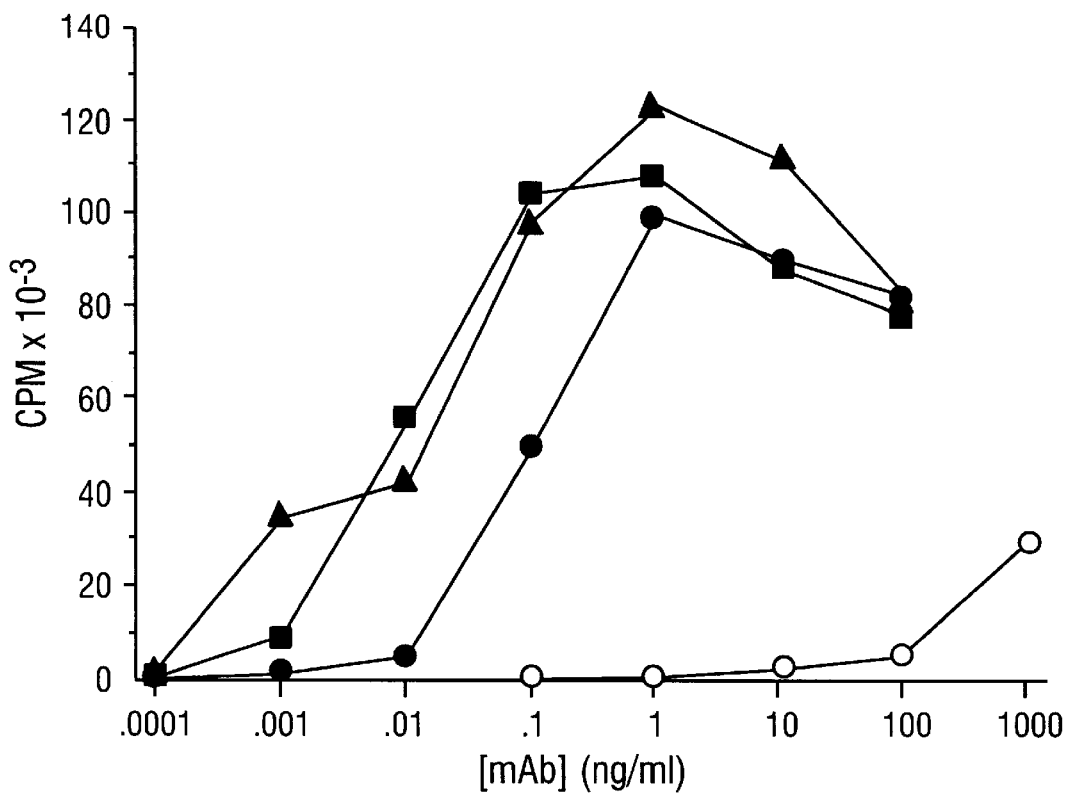
FIG. 15. T cell proliferation to "humanized" mAbs. $^3H$-thymidine incorporation by PBMC induced by soluble anti-CD3 mAbs was examined. Human PBMCs were incubated with serial log dilutions of soluble OKT3 (closed circles), 209-IgG4 (closed squares), 209-IgG1 (closed triangles) or Ala-Ala-IgG4 (closed circles) mAbs for 72 hours, pulsed with $^3H$-thymidine for an additional 4 hours, and quantified by using scintillation counting. All data is expressed as mean counts per minute of triplicate samples.

Characteristics of the "humanized" mAbs. OKT3 and the "humanized" mAbs were shown in companion studies to have similar avidities for the human CD3 complex, as determined by flow cytometry (FCM) in a competitive binding assay using FITC-coupled OKT3 (Alegre, 1992). In a competitive inhibition assay for FcR binding using $^{125}$I-human IgG and the human monocytic cell-line U937, OKT3, 209-IgG4 and 209-IgG1 were found to have similar affinities for human FcτRs, whereas the binding of the Ala-Ala-IgG4 and Ala-Ala-IgG1 mAbs to human FcτRI or FcτRII were greatly reduced (Xu et al., manuscript in preparation). Finally, the "humanized" mAbs were tested for their ability to induce T cell proliferation. Stimulation of PBMCs with the 209-IgG4 or 209-IgG1 mAbs resulted in cell proliferation comparable to that observed with PBMCs stimulated with murine OKT3 (FIG. 15). In contrast, no significant proliferation was induced by the Ala-Ala-IgG4 mAb at concentrations up to 100 ng/ml. In fact, the proliferation observed at the highest concentrations may be due to aggregation of the mAb. These results suggest that the alteration of the FcτR-binding region of this mAb had impaired its mitogenic properties.

Figure 16:
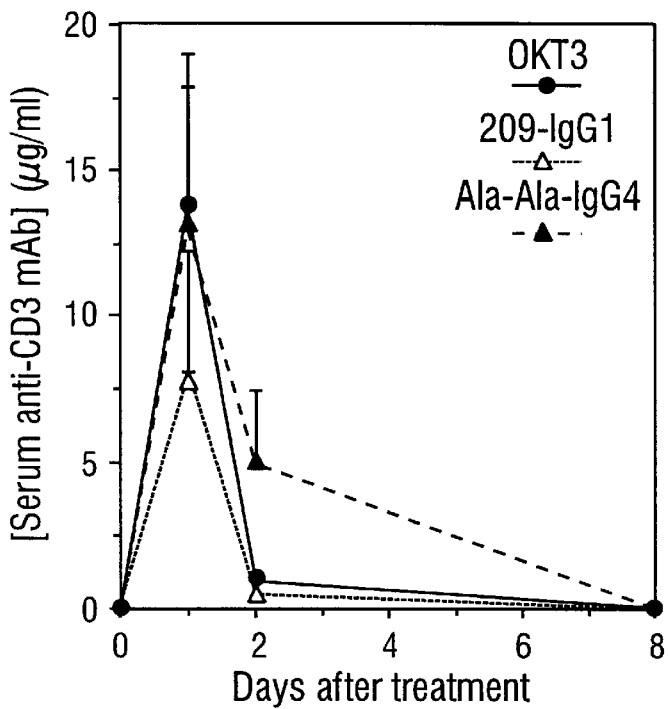
FIG. 16. Serum levels of anti-CD3 mAbs. Hu-SPL-SCID mice received OKT3, 209-IgG1 or Ala-Ala-IgG4 (100 µg in 1 ml PBS ip). The animals were bled 1, 2 and 8 days after the injection. Serum levels of anti-CD3 were measured by FCM as described in materials and methods. Results are expressed as Mean±SEM of 5 animals per group.

Determination of the circulating levels of anti-CD3 mAbs. Ten days to three weeks after injection of $10^8$ human splenic cells in the peritoneal cavity, SCID mice were tested for the percentage of human cells engrafting their peripheral blood. As previously described, graft versus host disease (GVHD) was apparent in mice bearing more than 25 to 30% human cells (Alegre et al., manuscript submitted). Therefore, in order to minimize the level of human T cell activation prior to anti-CD3 treatment, animals with 5% to 20% circulating human CD45$^+$ cells were selected for subsequent experiments. Mice matched for their level of engraftment with human cells were assigned to different groups for treatment with OKT3, 209-IgG1, Ala-Ala-IgG4 or PBS. As shown in FIG. 16, significant serum levels of all of the anti-CD3 mAbs (between 8 and 13 μg/ml) were measured 24 h after the injections. No anti-CD3 mAb was detected in SCID or hu-SPL-SCID mice treated with PBS (data not shown). The persistence of the mAbs was relatively short, inasmuch as levels decreased dramatically by 48 h. These data are consistent with results reported previously of a short half-life of immunoglobulins in other hu-SPL-SCID experimental models (Duchosal, 1992). They also are reminiscent of the time course for clearance of circulating OKT3 following its injection into humans (Thistlethwaite, 1988).

Depletion of T cells following administration of anti-CD3 mAbs. The injection of OKT3 and 209-IgG1 into hu-SPL-SCID mice induced a rapid and substantial depletion of circulating human CD45$^+$ cells, that was almost maximal when first measured, 3 h after the injection (data not shown). These data are consistent with the clearance of T cells from the peripheral blood seen in humans following the injection of OKT3. Interestingly, the depletion observed in the peripheral blood after administration of Ala-Ala-IgG4 in hu-SPL-SCID mice was consistently less striking than after the injection of the activating anti-CD3 mAbs, suggesting that binding of the anti-CD3 mAbs to FcτRs might play a role in the reduction of the number of circulating T cells. The clearance of human cells from the spleen and peritoneal cavity was not complete after a single injection of any of the anti-CD3 mAbs, activating or non-activating. In addition, the kinetics of depletion in the spleen were slower than in the peripheral blood, with maximal loss of 60% of the human cells not achieved until 48 h (data not shown). In contrast, a protocol analogous to that employed clinically in human transplant recipients, consisting of 14 consecutive days of i.p. administration of the anti-CD3 mAbs (10 μg), resulted in a complete depletion of CD3+T cells in the peripheral blood, the spleen and the peritoneal cavity even after Ala-Ala-IgG4 (data not shown). This absence of CD3$^+$ cells was not due to modulation and/or coating of the TCR complex by mAbs, inasmuch as staining with PE-coupled anti-CD4 or anti-CD8 mAbs did not reveal any remaining human T cells. Furthermore, hu-SPL-SCID splenocytes harvested 3 days after the completion of this protocol were unable to proliferate to immobilized OKT3, in vitro (data not shown). It is interesting to note that the ability of OKT3 to deplete T cells from human lymphoid compartments such as spleen or lymph nodes is unknown. However, studies using the anti-mouse CD3 mAb, 145-2C11, have shown that T cells are also depleted from the peripheral lymphoid organs of the immunocompetent mice.

Figure 17:
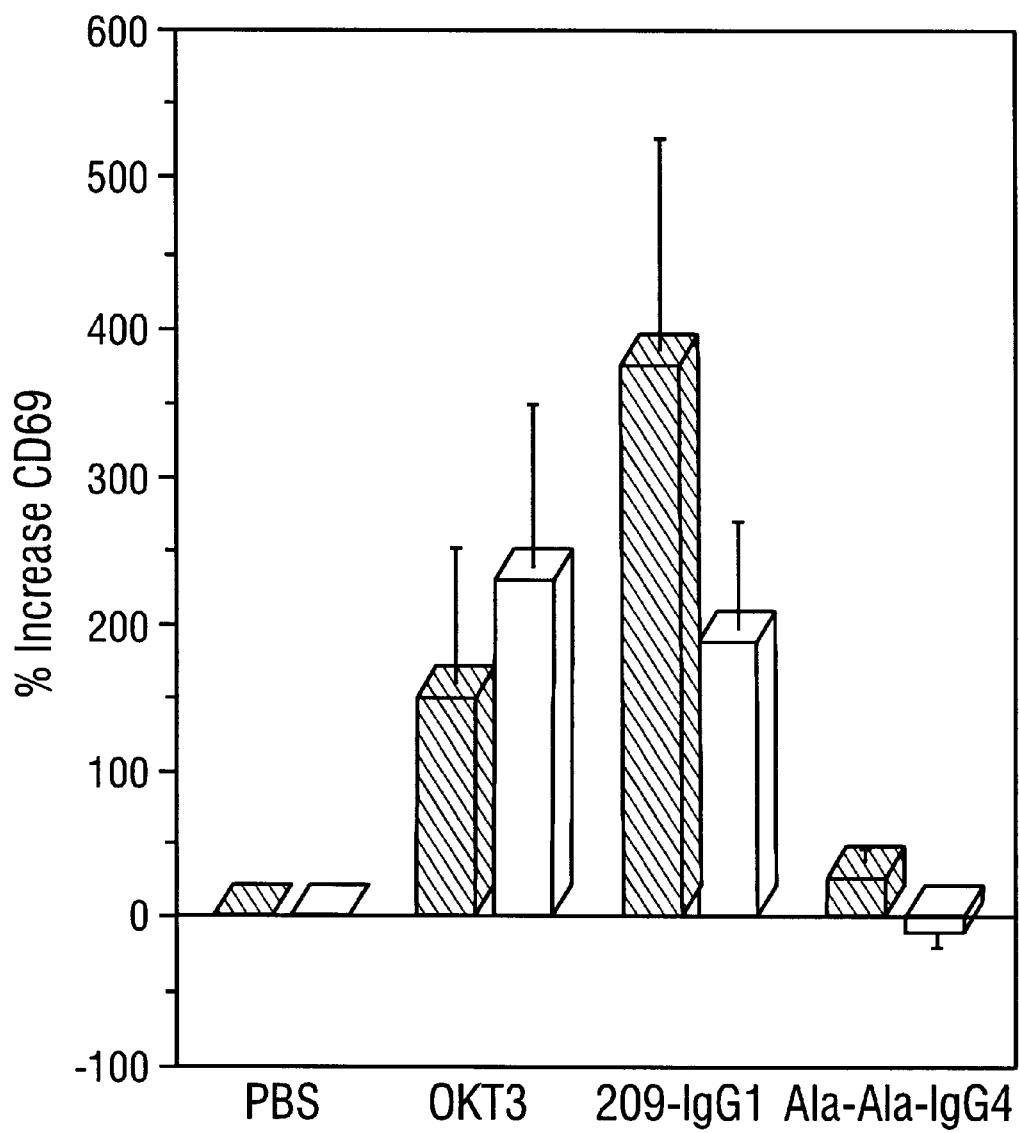
FIG. 17. Ala-Ala-IgG4 does not induce upregulation of CD69. Hu-SPL-SCID mice were treated with PBS (1 ml) or OKT3, 209-IgG1 or Ala-Ala-IgG4 (100 µg in 1 ml PBS ip). Spleens were harvested 24 h after the injection, prepared into single cell suspensions and analyzed by FCM. The mean fluorescence obtained with anti-human CD69 on $CD4^+$ and $CD8^+$ human T cells of PBS-treated mice was used as baseline. Results are expressed as the percent increase from that baseline (Mean±SEM of 5 animals per group) and are representative of 4 independent experiments.

Induction of surface markers of activation on T cells after administration of anti-CD3 mAbs. An early event following injection of OKT3 into transplant recipients is the activation of CD3$^+$ T cells due to the cross-linking of the TCR by FcτR$^+$ cells (Abramowicz, 1989; Chatenoud, 1989; Ceuppens, 1985). T cell activation in patients results in increased surface expression of markers such as CD69, CD25 and HLA-DR. As previously described, a significant percentage of hu-SPL-SCID T cells express CD25 and HLA-DR, as a result of GVHD (Alegre et al., manuscript submitted). In contrast, levels of CD69, which is an earlier and more transient marker of activation, are comparable to those found on T cells from humans. A significant increase in the expression of CD69$^+$ on both CD4$^+$ and CD8$^+$ splenocytes was observed 24 h after the injection of OKT3 and 209-IgG1 into hu-SPL-SCID mice, but not after the administration of Ala-Ala-IgG4 or PBS (FIG. 17), suggesting that the Ala-Ala-IgG4 mAb induced less T cell activation than the FcτR-binding anti-CD3 mAbs.

Figure 18:
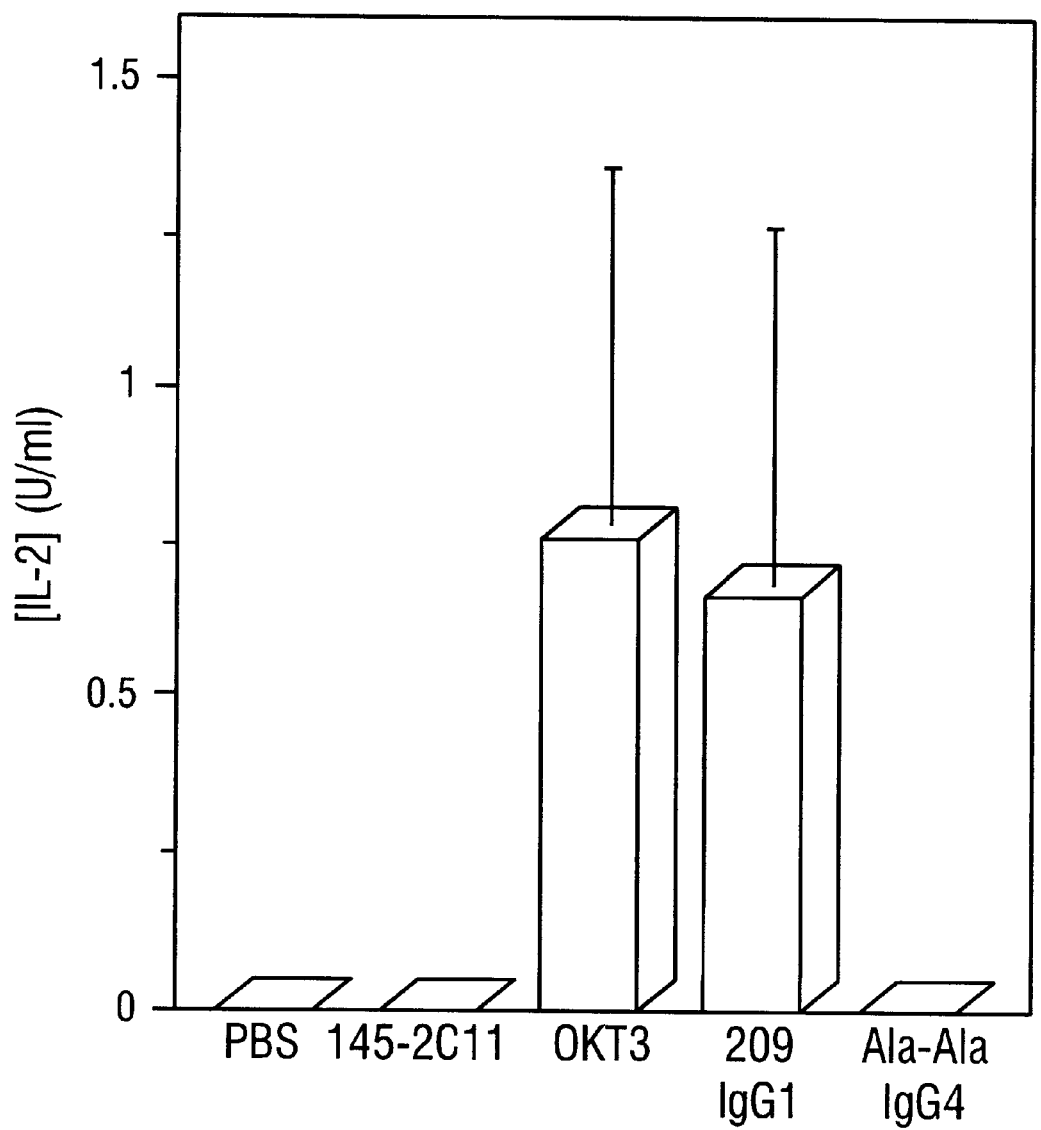
FIG. 18. Production of human IL-2 after injection of anti-CD3 mAbs. Hu-SPL-SCID mice received PBS (1 ml) or 145-2C11, OKT3, 209-IgG1 or Ala-Ala-IgG4 (100 µg in 1 ml PBS ip). Mice were bled 2 h after the injection, and sera were analyzed for human IL-2 levels, using a bioassay, as described in materials and methods. Results are displayed as the Mean±SEM of 4 mice/group, and are representative of 2 independent experiments.

Production of IL-2 after anti-CD3 therapy. The administration of OKT3 to patients has been shown to induce the rapid systemic release of cytokines such as TNF-α, IL-2, IL-6 and IFN-τ, peaking 2 to 6 h after the injection (Abramowicz, 1989; Chatenoud, 1989). This cytokine production results in the acute toxicity associated with anti-CD3 therapy in transplant recipients. In the present study, a bioassay was used to measure the serum level of human IL-2 2 h after treatment of hu-SPL-SCID mice with PBS, OKT3, 209-IgG1, Ala-Ala-IgG4 or 145-2C11, a hamster anti-murine CD3 mAb. As shown in FIG. 18, only the injection of OKT3 and 209-IgG1 induced the release of detectable human IL-2 in hu-SPL-SCID mice. The levels detected were low because of the relatively small percentage of engrafted human cells, but readily detectable in the experiments performed. The lymphokine production from individual animals varied as a consequence of the different percentage of human cells engrafting each animal. No human or murine IL-2 was detected after injection of 145-2C11, confirming the absence of endogenous murine T cells in these mice. The administration of Ala-Ala-IgG4 did not induce IL-2 production, consistent with the reduced ability of this mAb to fully activate human T cells. To verify the human origin of the cytokines detected, polymerase chain reaction assays were performed on spleens of SCID and hu-SPL-SCID mice 6 h after treatment, using primers that did not cross-react with murine cytokines. In addition to IL-2, IFN-τ mRNA was found to be up-regulated after injection of the OKT3 and 209-IgG1 mAbs, but not the Ala-Ala-IgG4 mAb (data not shown). Together, these results demonstrate that the Ala-Ala-IgG4 mAb has reduced activating properties as compared with OKT3 and 209-IgG1.

Figure 19:
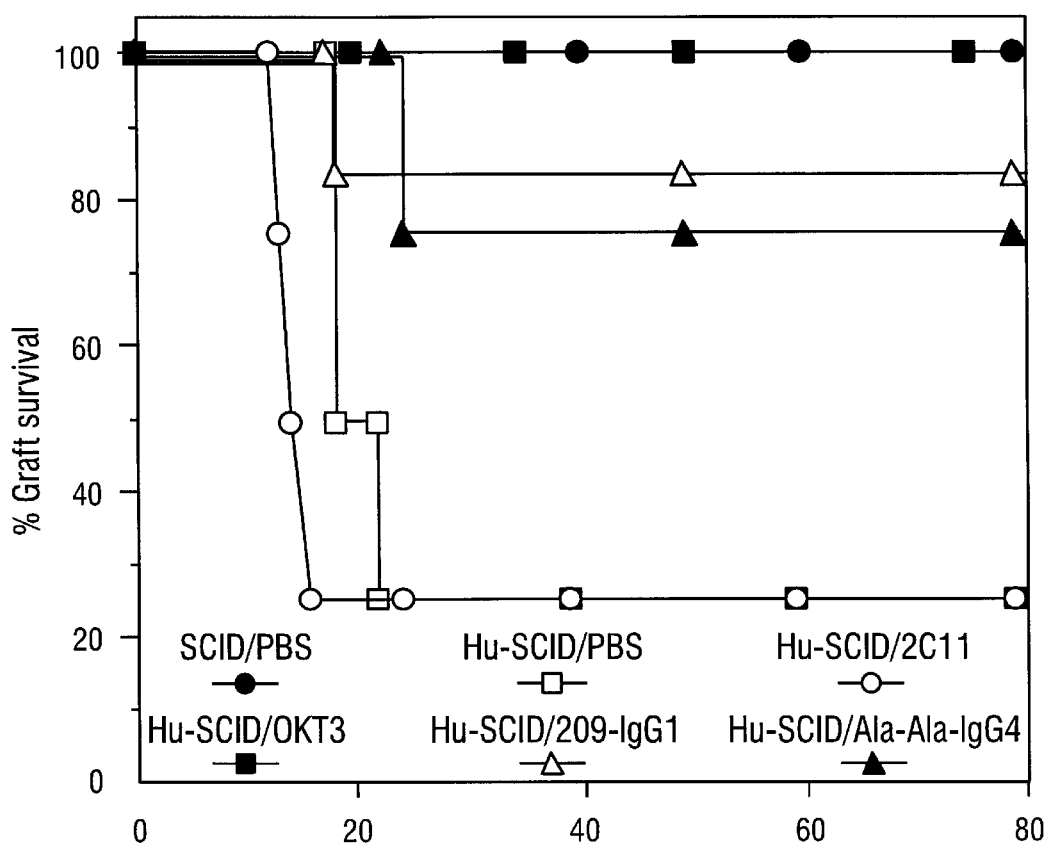
FIG. 19. Prolongation of human allograft survival by anti-CD3 mAbs. SCID (4 mice) and hu-SPL- SCID mice (29 mice) were grafted with allogeneic human foreskin. Hu-SPL-SCID mice were treated with PBS (1 ml/d for 14 days, 4 mice), 145-2C11 (4 mice), OKT3 (8 mice), 209-IgG1 (6 mice) or Ala-Ala-IgG4 (5 mice). mAbs were administered ip at 50 µg/day for 5 days followed by 10 µg/day for 10 days. Results are representative of 3 independent experiments. A two-tailed FISHER EXACT test was used to compare the various groups in the 3 skin graft experiments performed. No difference in efficacy was found between the different Abs as the best results were achieved by different Abs in each experiment (OKT3 vs. 209-IgG: p=0.12; OKT3 vs Ala-Ala-IgG: p=1.0; 209-IgG vs. Ala-Ala-IgG: p=0.23).

Prolongation of skin graft survival by the administration of anti-CD3 mAbs. The immunosuppressive properties of the different mAbs was next examined. Previous studies have shown that the 209-IgG1 and the Ala-Ala-IgG4 mAbs were both effective at modulating TCR and suppressing cytotoxic T cell responses in vitro (Alegre, 1992; Xu et al., manuscript in preparation). Initial studies in vivo suggested a similar rapid immunosuppressive effect induced by both "humanized" mAbs, as TCR was significantly modulated from the cell surface 24 h following injection of either mAb (data not shown). However, in order to directly explore the immunosuppressive efficacy of these mAbs, the inventors performed skin graft experiments. Previous studies from the inventors' laboratory have shown that hu-SPL-SCID mice are capable of rejecting human foreskin allografts and that human T cells participate in this process (Alegre et al., manuscript submitted). SCID and hu-SPL-SCID mice were grafted with human foreskin obtained from circumcisions and assumed to be allogeneic with respect to the human cells used for the adoptive transfer. Hu-SPL-SCID mice matched for their level of human CD45 expression in the peripheral blood received either PBS or daily doses of OKT3, 209-IgG1, Ala-Ala-IgG4, or 145-2C11 for 15 consecutive days, beginning on the day of the skin graft. As shown in FIG. 19, animals that received PBS or 145-2C11 rejected their grafts with a 50% mean survival time of 13 days, consistent with the inventors previous results. In contrast, all of the OKT3-treated animals and all but 1 of the 209-IgG1- and Ala-Ala-IgG4-treated mice maintained their skin grafts for greater than 80 days. Mice were sacrificed at 80 days, and 2 animals per group were analyzed for the percent of human cells in the different cellular compartments. None of the anti-human CD3-treated mice reexpressed human $CD3^+$ cells in the peripheral blood, the spleen or the peritoneal cavity, as determined by FCM. In contrast, the PBS-treated animals retained a significant percentage of human $CD45^+$ and $CD3^+$ cells in the different compartments although the absolute numbers were reduced over time, as compared with the initial engraftment (data not shown). Three additional skin graft experiments have been performed with 5–7 animals per group. In these experiments, 66–80% of the animals treated with OKT3, 209-IgG1 and Ala-Ala-IgG4 maintained their grafts for as long as the animals were examined. In two of the three experiments, a higher percentage of mice treated with the Ala-Ala-IgG4 maintained their skin grafts permanently. No statistical difference was found between these 3 groups.

Discussion

These studies suggest that a "humanized" mAb derived from OKT3 and bearing mutations of 2 amino acids in the Fc portion to impede its binding to FcτRs does not induce human T cell activation in vivo in a preclinical model, but retains the immunosuppressive properties of the native mAb.

OKT3 has been shown to mediate T cell activation by cross-linking T lymphocytes and $FcτR^+$ cells (Palacios, 1985; Ceuppens, 1985; Kan, 1985). Because hu-SPL-SCID mice are chimeric animals comprising both murine and human $FcR^+$ cells, it was important to use mAbs that would have similar avidities for human and murine RcτRs. Thus, OKT3, a murine IgG2a, and the human 209-IgG1 mAb have a high affinity for FcτRs of both species (Xu et al., manuscript in preparation). In contrast, the human Ala-Ala-IgG4 bears mutations dramatically reducing its binding to murine and human FcτRs. The efficacy of engraftment of the different cellular compartments with human B cells, monocytes/macrophages and NK cells, as providers of human FcτR, is relatively low in this hu-SPL-SCID model [10% in the peritoneal cavity and the peripheral blood and 20% in the spleen (Alegre et al., manuscript submitted)], when compared to the proportion of human T lymphocytes observed. On the other hand, murine monocytes/macrophages and NK cells are functionally normal in SCID mice and express normal levels of murine RcτR (Bosma, 1991; Kumar, 1989). The type of accessory cell responsible for the cross-linking mediated by OKT3 and 209-IgG1 in this chimeric system, whether murine or human, was adequate to trigger cellular activation analogous to that observed in patients after the injection of OKT3. Indeed, OKT3 and 209-IgG1 -triggered activation of the human T lymphocytes was evident in the treated mice, as determined by the production of human IL-2 and the accumulation of human IFN-τ mRNA, as well as by the increased expression of the surface marker of activation, CD69, on T cells. In contrast, the inability of Ala-Ala-IgG4 to interact with FcτRs rendered this mAb incapable of fully triggering T cell activation.

The activation of T lymphocytes and $RcτR^+$ cells in patients treated with OKT3 is associated with adverse reactions such as fever, chills, headaches, acute tubular necrosis, diarrhea, acute respiratory distress syndrome etc. (Abramowicz, 1989; Chatenoud, 1989; Toussaint, 1989; Thistlethwaite, 1988; Goldman, 1990). Similarly, immunocompetent mice injected with 145-2C11 develop hypothermia, hypoglycemia, lethargy, liver steatosis and acute tubular necrosis (Alegre, *Eur. J. Immun.*, 1990; Alegre, *Transplantation*, 1991; Feran, 1990). Hu-SPL-SCID mice did not exhibit detectable symptoms after OKT3 or 209-IgG1 therapy if the percentage of human cell engraftment was moderate. However, when animals with more than 30% human cells in their PBMCs were injected with OKT3 or 209-IgG1, they became extremely lethargic and an increased percentage of animal deaths was observed. As shown previously, animals engrafted with a high percentage of human T cells often undergo a GVHD-like syndrome, that results in a number of pathological symptoms including pancreatitis, diffuse hemorrhagic necrosis and in many instances animal death. Interestingly, the administration of Ala-Ala-IgG4 to highly engrafted animals seemed to reduce the symptoms of GVHD and perhaps even prevent some deaths. The number of animals examined was, however, too small to generate statistical differences.

The administration of all 3 anti-CD3 mAbs to hu-SPL-SCID mice, whether activating or not, resulted in modulation of the CD3 molecules from the surface of T lymphocytes and subsequent T cell depletion (data not shown). Similarly, in transplanted patients treated with OKT3, rapid modulation of the TCR complex and T cell depletion from the peripheral circulation are presumably responsible for the immunosuppressive properties of the drug (Chatenoud, 1982). Importantly, in this study, the administration of the Ala-Ala-IgG4 mAb resulted in dramatic prolongation of allograft survival similarly to the activating OKT3 and 209-IgG1 mAbs. These findings indicate that complete T cell activation due to T lymphocyte/$FcR^+$ cell cross-linking may not be necessary for the achievement of a potent anti-CD3-mediated immunosuppression.

In summary, the Ala-Ala-IgG4, a mAb bearing 2 amino acid mutations in the Fc portion of a "humanized" OKT3, may prove useful in clinical transplantation to induce immunosuppression while being less immunogenic and induce less adverse reactions than OKT3. In addition, the use of a "humanized" mAb may lessen the generation of anti-xenotypic Abs that often arise after repeated administrations of OKT3 (Thistlethwaite, 1988). Finally, the non-activating Ala-Ala-IgG4 mAb might also widen the applications of anti-CD3 mAbs to patients suffering from autoimmune diseases, in whom treatment with OKT3 was never realized because of the potential adverse reactions and the strong humoral responses induced by the mAb.

Example 16

In Vitro Uses of Antibodies

In addition to the above-described uses, the claimed antibodies will have a variety of in vitro uses. Some of these are described below, others will be understood by those of skill in the art.

1. Immunoassays

The antibodies of the invention will find utility in immunoassays for the detection of CD3. Turning first to immunoassays, in their most simple and direct sense, preferred immunoassays of the invention include the various types of enzyme linked immunosorbent assays (ELISAs) known to the art. However, it will be readily appreciated that the utility of antibodies is not limited to such assays, and that other useful embodiments include RIAs and other non-enzyme linked antibody binding assays or procedures.

In the preferred ELISA assay, samples to be tested for CD3 are immobilized onto a selected surface, preferably a surface exhibiting a protein affinity such as the wells of a polystyrene microtiter plate. After washing to remove incompletely adsorbed material, one will desire to bind or coat a nonspecific protein such as bovine serum albumin (BSA), casein or solutions of milk powder onto the well that is known to be antigenically neutral with regard to the anti-CD3 antibody. This allows for blocking of nonspecific adsorption sites on the immobilizing surface and thus reduces the background caused by nonspecific binding of the antibody onto the surface.

After binding of antigenic material to the well, coating with a non-reactive material to reduce background, and washing to remove unbound material, the immobilizing surface is contacted with the anti-CD3 antibody in a manner conducive to immune complex (antigen/antibody) formation. Such conditions preferably include diluting with diluents such as BSA, bovine gamma globulin (BGG) and phosphate buffered saline (PBS)/Tween®. These added agents also tend to assist in the reduction of nonspecific background. The layered antibody is then allowed to incubate for from 2 to 4 hours, at temperatures preferably on the order of 25° to 27° C. Following incubation, the antibody-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the anti-CD3 antibody. Of course, in that the anti-CD3 will typically have a human IgG region, the second antibody will preferably be an antibody having specificity in general for human IgG. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 hours at room temperature in a PBS-containing solution such as PBS-Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline-6-sulfonic acid [ABTS] and $H_2O_2$, in the case of peroxidase as the enzyme label. Quantification is then achieved by measuring the degree of color generation, e.g., using a visible spectra spectrophotometer.

2. Fluorescence Activated Cell Sorting (FACS)

Fluorescent activated cell sorting, flow cytometry or flow microfluorometry provides the means of scanning individual cells for the presence of an antigen. The method employs instrumentation that is capable of activating, and detecting the exitation emissions of labeled cells in a liquid medium.

FACS is unique in its ability to provide a rapid, reliable, quantiative, and multiparameter analysis on either living or fixed cells. The "humanized" anti-CD3 antibodies provide a useful tool for the analysis and quantitation of antigenic, biophysical, and biochemical characteristics of individual cells. When used with electrostatic deflection technology, the antibodies of the present invention can be used for the specific isolation of subpopulations of cells.

3. Immunohistochemistry

The antibodies of the present invention may also be used in conjunction with both fresh-frozen and formalin-fixed, paraffin-embedded tissue blocks prepared from study by immunohistochemisty (IHC). For example, each tissue block consists of 50 mg of residual "pulverized" tumor. The method of preparing tissue blocks from these particulate specimens was developed and has been successfully used in previous IHC studies of various prognostic factors, and is well known to those of skill in the art (Brown et al. (1990); Abbondanzo et al. (1990); Allred et al. (1990)).

Briefly, frozen-sections may be prepared by (A) rehydrating 50 ng of frozen "pulverized" breast tumor at room temperature in PBS in small plastic capsules, (B) pelleting the particles by centrifugation, (C) resuspending them in a viscous embedding medium (OCT), (D) inverting the capsule and pelleting again by centrifugation, (E) snap-freezing in −70° C. isopentane, (F) cutting the plastic capsule and removing the frozen cylinder of tissue, (G) securing the tissue cylinder on a cryostat microtome chuck, and (H) cutting 25–50 serial sections containing an average of about 500 remarkably intact tumor cells.

Permanent-sections may be prepared by a similar method involving (A) rehydration of the 50 mg sample in a plastic microfuge tube, (B) pelleting, (C) resuspending in 10% formalin for 4 hours fixation, (D) washing/pelleting, (E) resuspending in warm 2.5% agar, (F) pelleting, (G) cooling in ice water to harden the agar, (H) removing the tissue/agar block from the tube, (I) infiltrating and embedding the block in paraffin, and (F) cutting up to 50 serial permanent sections.

4. Immunoprecipitation

The antibodies of the present invention are particularly useful for the isolation of CD3 by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All claimed matter can be made without undue experimentation.

REFERENCES

The following references, to the extent that they provide exemplary procedural or other details supplementary to those set forth herein, are specifically incorporated herein by reference.

Abbondanzo S. L. et al. (1990) *Breast Cancer Res. Treat.* 16:182.
Abramowicz D et al. (1989) *Transplantation* 47:606.
Adair J R (1992) *Immunological Reviews* 130:1.
Alegre M et al. (1990) *Eur. J Immunol.* 20:707.
Alegre M et al. (1990) *Transplant. Proc.* 22:1920.
Alegre M et al. (1991) *Transplantation* 52:674.
Alegre M et al. (1991) *J. Immunol.* 146:1184.
Alegre M et al. (1992) *J. Immunol.* 148:3461.
Allred D. C. et al. (1990) *Breast Cancer Res. Treat.* 16:182.
Anderson C. L., R. J. Looney (1986) *Today.* 7:264.
Bentin J et al. (1991) *Cell. Immunol.* 132:339.
Berzofsky J A, Berekower I J (1984) *Fundamental Immunology, Paul W E, ed.,* 595.
Boot J H et al. (1989)*J. Immunol.* 142:1217.
Bosma G C et al. (1983) *Nature* 301:527.
Bosma M J et al. (1991) *Ann. Rev. Immunol.* 9:323.
Brown R. W. et al. (1990) *Breast Cancer Res. Treat.* 16:192.
Burton D R (1985) *Mol. Immunol.* 22:161.
Ceuppens J L et al. (1985) *J. Immunol.* 135:3882.
Chatenoud L et al. (1982) *Eur. J. Immunol.* 12:979.
Chatenoud L (1989) *Curr. Opin. in Immunol.* 2:246.
Chatenoud L et al. (1989) *N. Engl. J. Med.* 320:1420.
Chatenoud L et al. (1990) *Transplantation* 49:697.
Cherwinski H M et al. (1987) *J. Exp. Med.* 166:1229.
Chesselet M. F. (1990) *In situ hybridization histochemistry.* CRC Press.
Chothia C et al. (1989) *Nature* 342:877.
Chothia C, Lesk A M (i987) *J. Mol. Biol.* 196:901.
Cosimi A B et al. (1985) *Transplantation* 32:535.
Debets J M et al. (1989) *J. Immunol.* 144:1304.
Duchosal M A et al (1992) *Cell Immunol.* 139:468.
Duncan A R et al. (1988) *Nature* 332:563.
Ellenhorn J D I et al. (1992) *Transplantation* In press.
Ferran C et al. (1990) *Eur. J. Immunol.* 20:509.
Ferran C et al. (1990) *Transplantation* 50:642.
Frenken L. A. et al. (1991) *Transplantation.* 51:881.
Gergely J. and G. Sarmay (1990) *FASEB J.* 4:3275.
Goldman M et al. (1990) *Transplantation* 50:148.
Grantham R, Perrin P (1986) *Immunology Today* 7:160.
Hale G et al. (1988) *Lancet* ii:1394.
Hird V et al. (1991) *Br. J. Cancer* 64:911.
Hirsch R et al. (1990) *Transplantation.* 49:1117.
Hirsch R et al. (1991) *J. Immunol.* 147:2088.
Hirsch R et al. (1991) *Transplant Proc.* 23:270.
Ho S N et al. (1989) *Gene* 77:51.
Isaacs J D et al. (1992) *Lancet* 340:748.
Jefferies R et al. (1990) *Mol. Immunol.* 27:1237.
Kabat E A et al. (1987) *Washington DC: United States Department of Health and Human Services* 4th Edition.
Kan E A et al. (1986) *Cell Immun.* 98:181.
Kozak M (1987) *J. Mol. Biol.* 196:947.
Kramer W et al. (1984) *Nucl. Acids Res.* 9441.
Kreis H et al. (1989) *Transplant Proc.* 21:1741.
Krutmann J. et al. (1990) *J. Immunol.* 145:1337.
Kumar V et al. (1989) *Curr. Topics Microbiol. Immun.* 152:47.
Laing T J and A. Weiss (1988) *J. Immunol.* 140:1056.
Landegren U et al. (1982) *J. Exp. Med.* 155:1579.
Lanert P et al. (1991) *Intern. Rev. Immunol.* 17:529.
Ledbetter J A et al. (1990) *Sem. Immunol.* 2:99.
Leo O et al. (1987) *Proc. Natl. Acad. Sci., USA* 84:1374.
Li Y W et al. (1990) *Mol. Immunol.* 27:303.
LoBuglio A F et al. (1989) *Proc. Natl. Acad. Sci. USA.* 86:4220.
Looney R J et al. (1986) *J. Immunol.,* 136:1641.
Lucas B A et al. (1993) *Transplant Proc.* 25:543.
Lund J et al. (1991) *J. Immunol.* 147:2657.
Lynch R. G. et al. (1990) *Mol. Immunol.* 27:1167.
Mathieson P W et al. (1990) *New Engl. J. Med.* 323:250.
McCune J et al. (1991) *Ann. Rev. Immunol.* 9:399.
McCune J et al. (1991) *Curr. Opin. Immunol.* 3:224.
Morikawa S et al. (1988) *Int. J. Cancer.* 21:166.
Morrison S L et al (1984) *Proc. Natl. Acad. Sci. USA* 81:6351.
Mosmann T (1983) *J. Immunol. Methods* 65:55.
Newell K M et al. (1990) *Nature* 347:286.
Ollo R. and F. Rougeon (1983) *Cell.* 32:515.
Ohara J and Paul W E (1985) *Nature* 315:333.
Ortho MultiCenter Transplant Study Group (1985) *N. Engl. J. Med.* 313:337.
Palacios R (1985) *Eur. J. Immunol.* 15:645.
Parleviet K J et al. (1990) *Transplantation.* 50:889.
Partridge L J et al. (1986) *Mol. Immunol.* 23:1365.
Perussia B et al (1983) *J. Exp. Med.* 158:1092.
Petroni K C et al. (1988) *J. Immunol.* 140:3467.
Poljak R (1991) *Mol. Immunol.* 28:1341.
Rao P E et al. (1991) *Transplantation* 52:691.
Rao P E et al. (1992) *Human Immunol.* In press.
Riechmann L et al. (1988) *Nature* 332:323.
Routledge E G et al. (1991) *Eur. J. Immunol.* 21:2717.
Sahagan B. G. et al. (1986)*J. Immunol.* 137:1066.
Sambrook J et al. (1989) *Cold Spring Harbor Laboratory Press* 2nd Edition.
Salmeron A et al. (1991) *J. Immunol.* 147:3047.
Shearman C W et al. (1991) *J. Immunol.* 146:928.
Shen L et al. (1987) *J. Immunol.* 139:534.
Sikder S K et al. (1985) *J. Immunol.* 135:4215.
Slarneron A et al. (I991) *J. Immunol.* 147:3047.
Steplewski Z et al. (1988) *Proc. Natl. Acad. Sci. USA.* 85:4852.
Thistlewaite J R et al. (1988) *Am. J. Kidney Dis.* 11:112.
Thistlewaite J R Jr et al. (1984) *Transplantation* 38:695.
Thistlewaite J R Jr et al. (1987) *Transplantation* 43:176.
Toussaint C et al. (1989) *Transplantation* 48:524.
Tramontano A et al. (1990)*J. Mol. Biol.* 215:175.
Transy C et al. (1989) *Eur. J. Immunol.* 19:947.
van Lier R A et al. (1987) *Eur. J. Immunol.* 17:1599.
van Seventer G A et al. (1987) *J. Immunol.* 139:2545.
van Lier R A et al. (1987) *J. Immunol.* 139:2873.
van Lier R A et al. (1989) *Immunology.* 68:45.

Van Wauve J P et al. (1984) *J. Immunol.* 133:129.
Van Wauwe J P et al. (1980) *J. Immunol.* 124:2708.
Waid T H et al. (1991) *Transplant Proc.* 23:1062.
Waid T H et al. (1992) *Transplantation* 53:80.
Wawrzynczak E J et al. (1992) *Mol. Immunol.* 29:221.
Weiss A et al. (1986) *Ann. Rev. Immunol.* 4:593.
Whittle N et al. (1987) *Prot. Eng.* 1:499.

Woodle S E et al. (1991) *I. Immunol.*, in press.
Woodle E S et al. (1991) *Transplantation* 51:271.
Woodle et al. (1991) *Transplantation* 52:354.
Woodle E S et al. (1983) *Transplantation.* 52:361.
Woodle E S et al. (1992) *J. Immunol.* 143:2756.
Woof J M et al. (1984) *G. Mol. Immunol.* 21:523.
Woof J M et al. (1986) *G. Mol. Immunolo.* 23:319.

---

What is claimed is:

1. A humanized anti-CD3 monoclonal antibody comprising an antigen binding region of murine OKT3 monoclonal antibody and a point-mutated human IgG1 Fc region comprising an alanine at position 234 of the CH2 portion and an alanine at position 235 of the CH2 portion, wherein the antibody has reduced T cell mitogenic properties relative to murine OKT3 monoclonal antibody and does not bind C1q.

2. A humanized anti-CD3 monoclonal antibody comprising the complementary determining regions of murine OKT3 and a point-mutated human IgG1 Fc region comprising an alanine at position 234 of the $CH_2$ portion and an alanine at position 235 of the $CH_2$ portion, wherein the antibody has reduced T cell mitogenic properties relative to murine OKT3 and does not bind C1q.

3. A pharmaceutical composition comprising a humanized anti-CD3 monoclonal antibody comprising an antigen binding region of murine OKT3 monoclonal antibody and a point-mutated human IgG1 Fc region comprising an alanine at position 234 of the CH2 portion and an alanine at position 235 of the CH2 portion, wherein the antibody has reduced T cell mitogenic properties relative to murine OKT3 monoclonal antibody and does not bind C1q, and a physiologically acceptable carrier.

4. A method of using a humanized anti-CD3 monoclonal antibody comprising an antigen binding region of murine OKT3 monoclonal antibody and a point-mutated human IgG1 Fc region comprising an alanine at position 234 of the CH2 portion and an alanine at position 235 of the CH2 portion, wherein the antibody has reduced T cell mitogenic properties relative to murine OKT3 monoclonal antibody and does not bind C1q for the manufacture of a medicament for the suppression of an immune response-triggered rejection of transplanted organ tissue, said medicament being administered to an organ transplant patient, either before, during or after transplantation, in a physiologically acceptable carrier.

5. A method of suppressing immune response-triggered rejection of transplanted organ tissue, comprising the step of administering to an organ transplant patient either before, during or after transplantation, a humanized anti-CD3 monoclonal antibody comprising an antigen binding region of murine OKT3 monoclonal antibody and a point-mutated human IgG1 Fc region comprising an alanine at position 234 of the CH2 portion and an alanine at position 235 of the CH2 portion, wherein the antibody has reduced T cell mitogenic properties relative to murine OKT3 monoclonal antibody and does not bind C1q, in a physiologically acceptable carrier.

* * * * *

UNITED STATES PATENT AND TRADEMARK OFFICE
CERTIFICATE OF CORRECTION

PATENT NO. : 6,491,916 B1
DATED : December 10, 2002
INVENTOR(S) : Bluestone et al.

It is certified that error appears in the above-identified patent and that said Letters Patent is hereby corrected as shown below:

<u>Title page, Item [54] and Column 1, line 3,</u>
Please delete "IMMUNOSUPPRESSIVE" and insert -- IMMUNOSUPPRESSIVE -- therefor.
Item [63], please delete "1994" and insert -- 1993 -- therefor.

Signed and Sealed this

Twenty-ninth Day of April, 2003

JAMES E. ROGAN
*Director of the United States Patent and Trademark Office*